(12) United States Patent
Spitz et al.

(10) Patent No.: US 8,940,909 B2
(45) Date of Patent: Jan. 27, 2015

(54) INDICATOR PLATFORM

(75) Inventors: Urs Spitz, Herrliberg (CH); Lukas Wick, Winterthur (CH); Alexander Bayer, Goldach (CH); Christophe Weymuth, Zürich (CH); Günter Schabert, Goldach (CH)

(73) Assignee: Biosynth AG, Thal (CH)

( * ) Notice: Subject to any disclaimer, the term of this patent is extended or adjusted under 35 U.S.C. 154(b) by 538 days.

(21) Appl. No.: 13/266,707

(22) PCT Filed: May 6, 2010

(86) PCT No.: PCT/EP2010/056212
§ 371 (c)(1),
(2), (4) Date: Nov. 23, 2011

(87) PCT Pub. No.: WO2010/128120
PCT Pub. Date: Nov. 11, 2010

(65) Prior Publication Data
US 2012/0058503 A1    Mar. 8, 2012

(30) Foreign Application Priority Data
May 7, 2009 (EP) ..................... 09159639

(51) Int. Cl.
*C07D 209/70* (2006.01)
*C07D 209/36* (2006.01)
*C07D 487/04* (2006.01)

(52) U.S. Cl.
CPC ............ *C07D 209/36* (2013.01); *C07D 487/04* (2013.01)

USPC .......................................................... 548/420

(58) Field of Classification Search
None
See application file for complete search history.

(56) References Cited

FOREIGN PATENT DOCUMENTS

EP    1790734    5/2007

OTHER PUBLICATIONS

Rogness et al., Rapid synthesis of the indole-indole scaffold via [3+2] annulation of arynes by methyl indole-2-carboxylates, *Tetrahedron Letters*, vol. 50, No. 28 (2009) XP026158712.
Goddard et al., Recent advances in enzyme assays, *Trends in Biotechnology*, vol. 22, No. 7 (2004) XP004520509.
Crawford et al., Isoindolo[2,1-a]indol-6-one a new pyrolitic synthesis and some unexpected chemical properties, *Organic & Biomolecular Chemistry*, vol. 6, 2008, XP002549268.
European Search Report dated Mar. 28, 2010.
International Search Report dated Sep. 11, 2010.

*Primary Examiner* — Michael Barker
(74) *Attorney, Agent, or Firm* — Cozen O'Connor

(57) ABSTRACT

A novel indicator platform comprises a plurality of 1H-lndol-3-yl indicator compounds that are capable of converting to a signalophore compound in response to an external stimulus. In one class of indicator compounds, the resulting signalophores are 2-benzylideneindoline compounds that are formed by an intermolecular Aldol-type process; in a further class of indicator compounds, the resulting signalophores are 10H-indolo[1,2-a]indole compounds that are formed by an intramolecular Aldol-type process. The indicators can be used in a wide array of applications relating, for example, to biological systems or optical data storage.

15 Claims, 4 Drawing Sheets

INDICATOR PLATFORM

PRIORITY CLAIM

Figure 1:
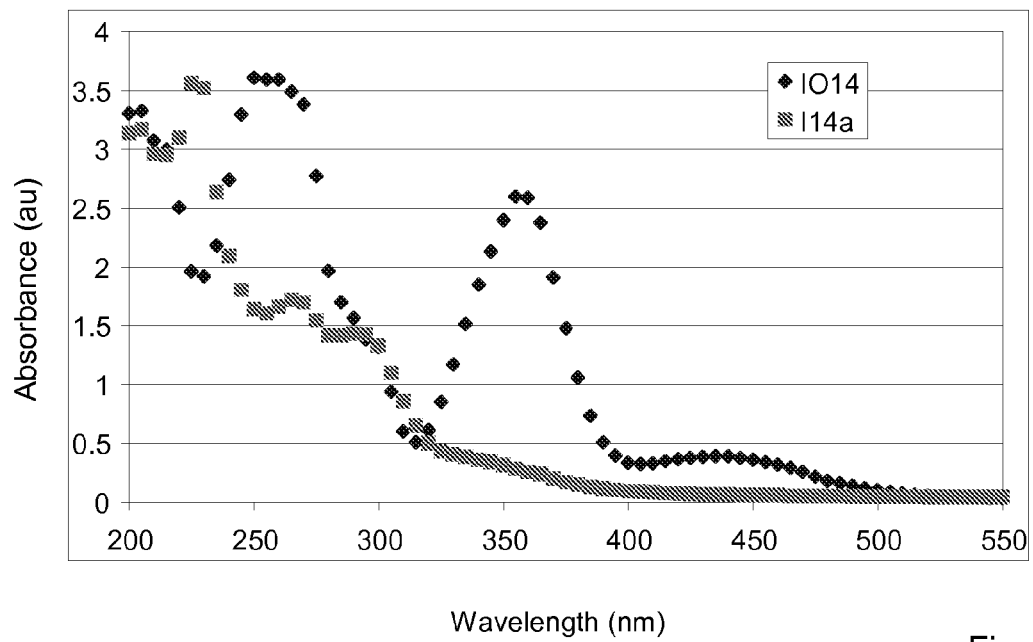
Figure 1:
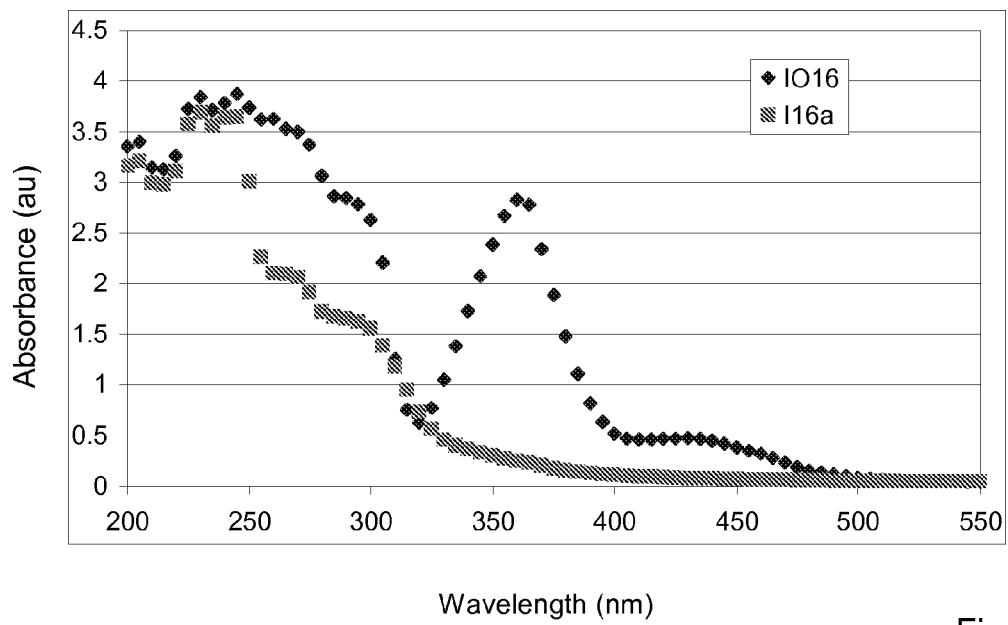
Figure 1:
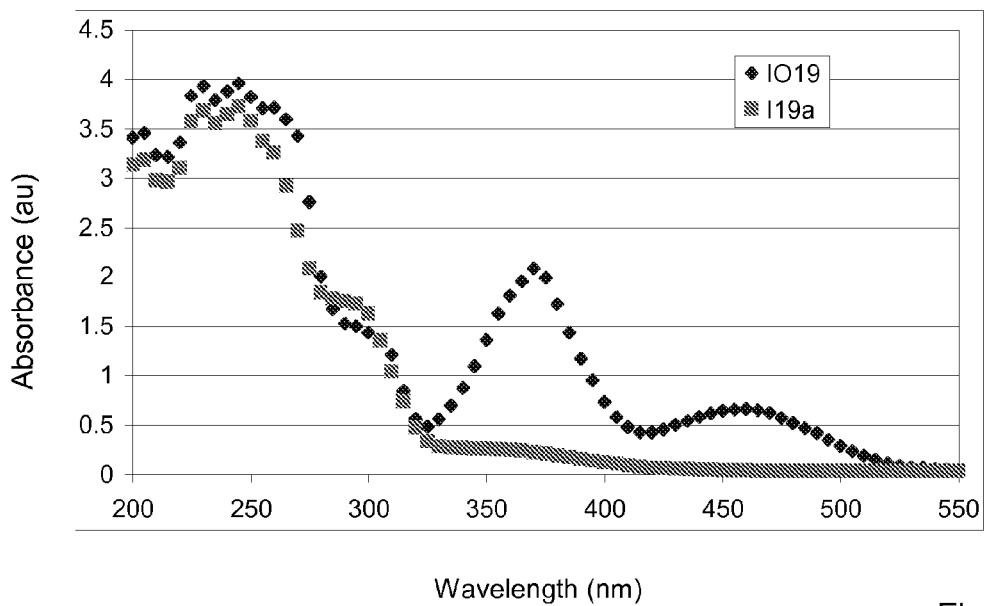
Figure 1:
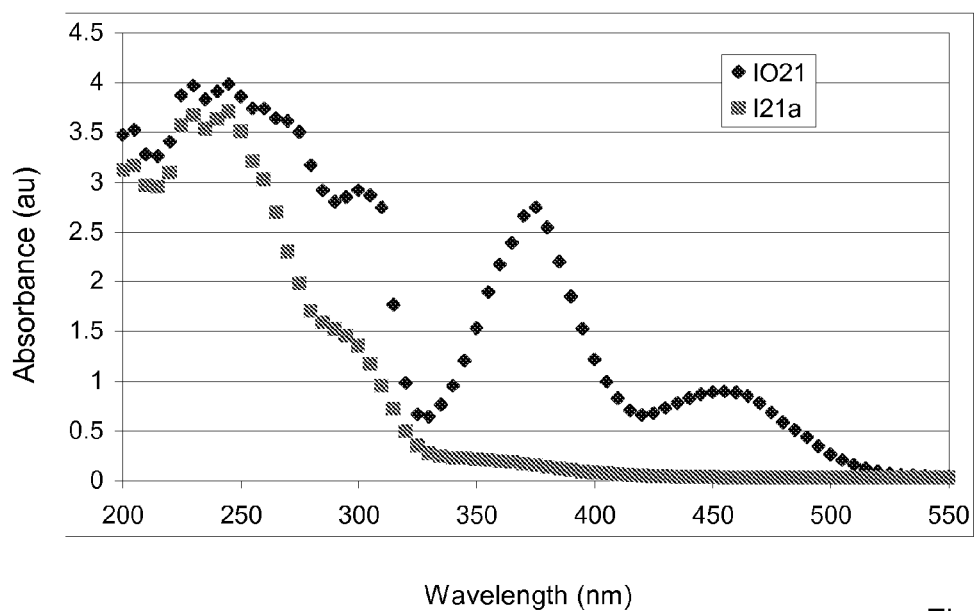
Figure 1:
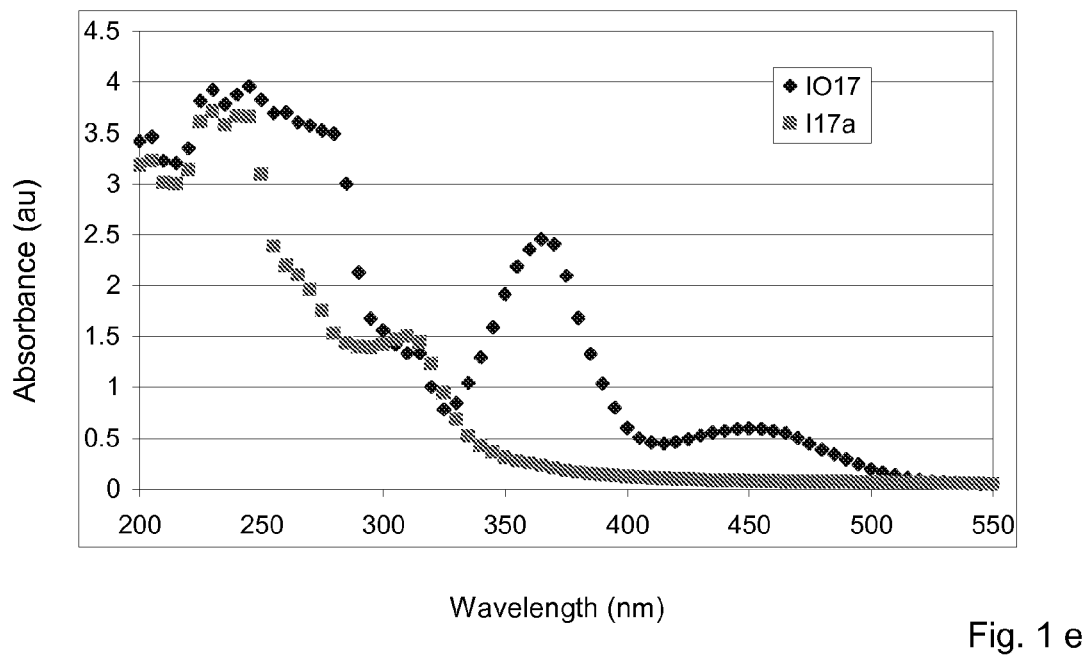
Figure 1:
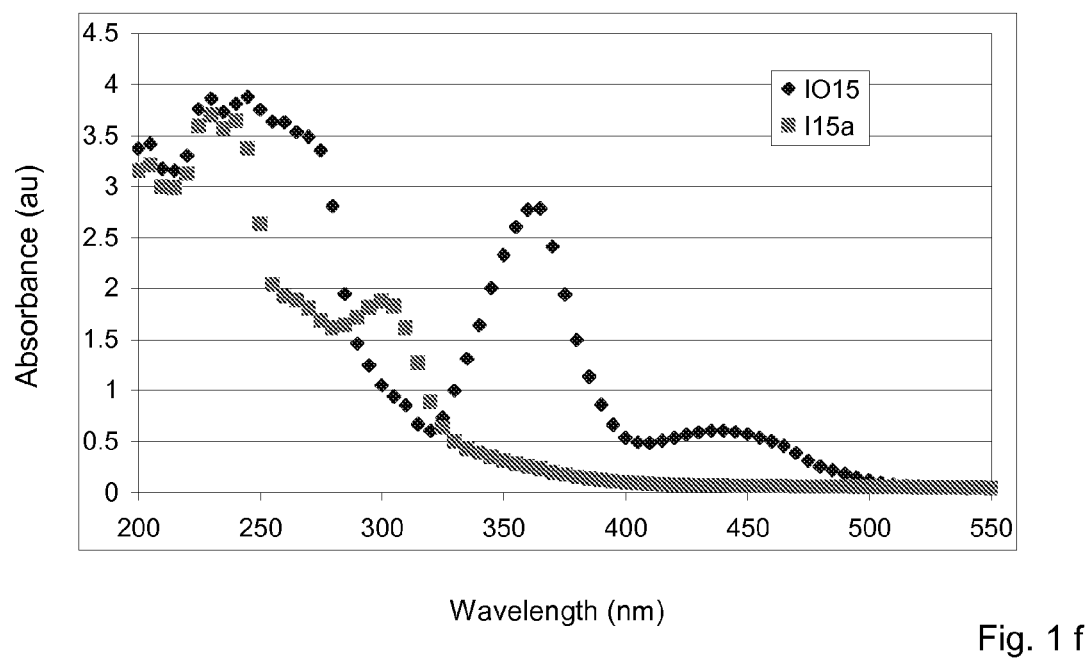

This is a U.S. national stage of application No. PCT/EP2010/056212, filed on May 6, 2010. Priority is claimed on the following application: EP, Application No.: 09159639.5, Filed: May 7, 2009, the content of which is incorporated here by reference.

FIELD OF THE INVENTION

The invention discloses of a new class of chromogenic and fluorogenic indicators responding to external stimuli such as biochemical environment, temperature or photo irradiation. The novel indicators offer broad potential in a wide array of applications relating, for example, to biological systems or optical data storage.

BACKGROUND OF THE INVENTION

Indicators are materials that produce a detectable signal (also denoted "dS") in response to an external stimulus (also denoted "eS"). Such stimuli typically include temperature, light (photo-labile or photochromic indicators), electric field (electrochromic indicators), pressure (piezoelectric indicators), ion concentration (e.g. pH indicators) and biochemical reactivity (e.g. enzyme indicators).

The mechanism of translation of stimulus into detectable signal is illustrated in Scheme I and typically involves the chemical removal or modification of a labile group (also denoted "LG") of the indicator in a process mediated by the experience of said stimulus.

Scheme I: Generic Concept and Terminology of Indicator Systems

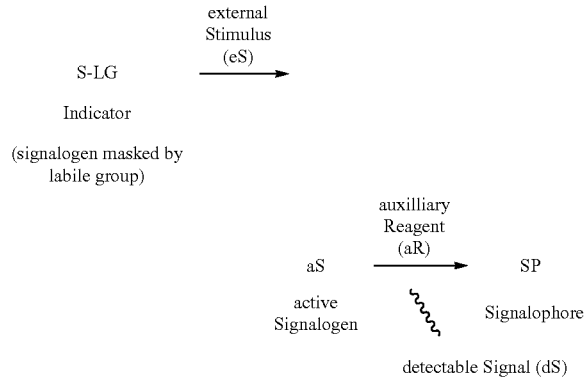

Removal or modification of the labile group most often yields an activated signalogen (also denoted "aS") which typically undergoes further transformation which often involves interaction with auxiliary reagents (also denoted "aR") to yield a signalophore (also denoted "SP"), the formation of which usually coincides with the occurrence of said detectable signal. Therefore, an indicator represents an activated signalogen that is masked, i.e. inactivated by a labile group. An indicator system (also denoted "IS") comprises the elements of activated signalogen, labile group, auxiliary reagent (optional), detectable signal and suitable means for interrogation of detectable signal. The appearance of a detectable signal is a consequence of experiencing an external stimulus and hence allows ready detection and/or quantification of the external stimulus by interrogation with suitable instrumentation or the human eye.

Examples of detectable signal include change in optical density, absorption or emission (e.g. chromogenic, fluorogenic and luminogenic indicators) or change in electric current or potential (electrogenic indicators).

A detectable signal may be transient or persistent in nature: For example a fluorogenic enzyme indicator may release a fluorescent entity upon experience of certain enzymatic activity. In this case the detectable signal is persistent in nature. In contrast a bioluminogenic indicator may emit light in response to the presence of ATP. The emission of light representing the detectable signal is transient in nature.

A detectable signal may be associated with transient or persistent external stimuli: For example, pH indicators continuously change color in response to changing proton concentrations, which represents a persistent external stimulus. In this case the corresponding indicators undergo reversible change and are termed reversible indicator systems. In contrast a photo-labile indicator may undergo lasting color change in response to a short laser pulse. In this case the corresponding indicators undergo irreversible change upon a single experience of external stimulus and are termed irreversible indicator systems.

There exist a large number of important technical applications including biology, diagnostics, chemistry and optical data storage that relate to irreversible indicators.

Indicators used in biology often respond to enzymatic activity. Enzyme indicators are used in many formats of assay. Such assays may be performed in solution phase which requires a soluble indicator system.

Other assays require the physical location of enzymatic activity. Here, a suitable indicator will stain the specific site associated with enzyme activity. For this purpose the indicator must form an insoluble precipitate in response to localized enzymatic stimuli. These types of indicators are termed insoluble or precipitating indicator systems. Precipitating indicator systems by nature are irreversible.

Detection of enzyme activity is important in diagnostic and testing applications as well as in biochemistry, molecular biology and histology research. In diagnostics, enzyme activity relates to the presence of microbial pathogens, as well as to metabolic ill functions or to genetic disorders.

Immunological methods are based on the interaction of antibodies with antigens. In order to detect such interaction, antibodies must be carrying a label. Enzymes are commonly used to label secondary antibodies. Hence, the detection of enzyme activity is fundamental to immunological assays. Immunological assays are widely used in clinical diagnostics, food and environmental testing, as well as in biochemical protocols such as Western blotting.

In molecular biology the detection of enzyme activity is needed in reporter gene protocols. Genetic expression of a reporter gene gives rise to enzyme activity that can be detected. This way, the researcher obtains information on genetic transformations.

1H-Indox-3-yl Indicator Systems

1H-Indox-3-yl (also denoted "Indox") indicators are well known chromogenic indicators widely used to visualize enzymatic activity in microbiology, immunology, biochemistry and genetics.

Indox indicator systems are derived from the 1H-indol-3-ol (3-hydroxyindol, respectively its tautomeric form indolin-3-one or 3-oxoindoline, denoted Indoxol) structure where the hydrogen atom of the 3-hydroxyl group is replaced by a labile group. Loss of the labile group yields Indoxol as an activated signalogen which interacts with atmospheric oxygen (a common auxiliary reagent) in a complex radical chain reaction to yield colloidal indigo stains as signalophor. A dramatic change in optical transmission of a sample associated with indigo dye formation represents a detectable signal of the indicator system.

Despite their widespread use and commercial significance, applications of Indox indicator systems suffer from some major limitations:

For instance, Indox indicator systems depend on molecular oxygen or other oxidizing auxiliary reagents to develop desired indigo signalophores. Due to said requirement indoxyl substrates are of limited or no use under anaerobic conditions. Considering the portion of enzyme assays that are performed in the absence of oxygen, this limitation is significant.

Therefore, indicators with properties similar to indoxyl indicators without the undesirable dependence on molecular oxygen or other oxidizers would constitute a major improvement over the state of the art.

Most popular Indox indicators yield stains ranging from violet to green because red indigos are less effective for the purpose of staining.

However, it would be desirable to have available a choice of colors when using chromogenic or fluorogenic indicator systems. This is of particular importance in dual or multiple enzyme assays requiring parallel detection or in applications that require optical contrast against off white background.

Therefore, novel chromogenic enzyme indicators that expand the current color selection into the range of yellow to red would represent a further valuable addition to the art.

Moreover, common enzyme indicators are either chromogenic or fluorogenic in nature: For example, common commercial enzyme indicators based on fluorophores such as 7-hydroxycoumarines (soluble fluorogenic indicators) or quinazolines (precipitating fluorogenic indicators—see for instance: EP 0 641 351 A1) lack significant absorption in the visible electromagnetic band and thus escape detection by the human eye without the application of optical instrumentation for interrogation. In contrast, common chromogenic indicators such those derived from 3-indoxyls lack fluorescence. This is true in particular for precipitating indicators since fluorescence in the solid state is a rare phenomenon (due to the well known effect of self-quenching of excited molecules arranged in a tight lattice).

It would be advantageous over the current state of the art if enzyme indicators were made available that have both chromogenic and fluorogenic properties.

Diazonium Staining

In histology, another type of indicator is well known and often used to localize enzyme activity. This important method was pioneered by Seligman et al. (*J. Histochem. Cytochem.* 1954, 2, 209-229), Burstone et al. (*J. Histochem. Cytochem.* 1956, 4, 217-226) and Rutenburg et al. (*J. Histochem. Cytochem.* 1958, 6, 122-129). It is based on the reaction of stabilized diazonium salts with electron rich aromatic amines and phenols to form azo dyes. Many azo dyes are of intense color and some are fluorescent.

This diazonium coupling reaction will proceed with aromatic amines and phenols much faster than with their corresponding esters and amides. Therefore, hydrolytic enzyme activity can be detected by exposing a sample to a suitable phenolic ester or anilide followed by staining with diazonium salts. Depending on the substrate and the diazonium salts, good localization can be achieved.

In practice, different types of chromogens such as naphtylamines or naphthol derivatives are employed. There exists considerable variety of commercially available substrates of this type along with suitable diazonium staining salts.

Pearson et al. (*Proc. Soc. Exptl. Biol. Med.* 1961, 108, 619-613; *Lab. Invest.* 1963, 12, 712-720), Yarborough et al. (*J. Reticuloendothelial Soc.* 1967, 4, 390-408), Gossrau et al. (*Histochemistry,* 1987, 397-404) and others developed staining methods that are based on the reaction of Indox indicators with diazonium electrophiles for use in histology.

Mohler and Blau (*Proc. Natl. Acad. Sci. USA* 1996, 12423-12427) have evaluated many indicator systems for beta-D-galactosidase combining Indox indicators and various commercial diazonium salts.

It should be noted, however, that due to the carcinogenicity and high toxicity towards humans and cell cultures and the otherwise hazardous nature of diazonium salts this method poses significant danger to the user and is not compatible with either in vivo or non-destructive type of assaying in general.

In view of all the above, a superior type of indicator releasing activated signalogen which spontaneously yield signalophores in a process that is entirely independent of external factors such as molecular oxygen or any reagent or chemical species present in the surrounding environment would be desirable.

Metal Chelates

Another class of precipitating substrates are based on metal chelating molecules that form insoluble complexes with metal ions. Chelating molecules contain two or more functional groups that coordinate to a metal ion. These functional groups can be masked by labile groups to prevent the formation of a metal complex which represents a relatively common design of indicator.

Enzyme indicators based on metal chelates do have some practical relevance. For example, substrates derived from 8-hydroxyquinolines such as 8-hydroxyquinoline-beta-D-glucuronide or the naturally occurring esculetin (esculin-beta-D-glucopyranoside) can be used to detect the corresponding enzymes in the presence of iron(III) salts.

However, these indicators suffer from other drawbacks: Many of these chelating molecules display biocidal effects on culture. Such toxicity is intrinsic to any metal chelating agents since they generally interfere with the functioning of metallo-enzymes. Further, one must maintain a certain concentration of metal ions present in the assay, which may cause undesirable interference. In addition, most stains produced from metal chelation are brown and hence will not provide good contrast from background.

For example, 8-hydroxyquinoline is an excellent ligand that forms stable complexes with many transition metals. Masking the hydroxyl group with a suitable labile group produces potentially useful indicators. The assay will release 8-hydroxyquinoline as the activated signalogen which rapidly binds iron(II or III) thereby forming a precipitating metal complex that is dark colored. Moreover, 8-hydroxyquinoline possesses significant anti-microbial activity which may inhibit the growth of some prominent organisms within the format of a microbial assay. Accordingly, enzyme indicators preferably should not involve chelating agents or unnatural metal ion concentrations which by nature interfere with the course of the assay.

SUMMARY OF THE INVENTION

The present invention aims at overcoming severe limitations of current indicators including:

- The requirement of auxiliary staining reagents such as oxygen, oxidizers, metal ions, drastic pH conditions or toxic diazonium salts.
- The presence of toxic reagents, intermediates or products that potentially impact the assay.
- The limitation of indicator color of precipitating chromogenic indicators to the green-blue-violet range (lacking yellow to red).
- The lack of choice in precipitating enzyme indicators that exhibit fluorogenic properties.
- The lack of precipitating enzyme indicators that integrate chromogenic and fluorogenic properties.

The present invention is based on the discovery that 1H-Indox-3-yl compounds and derivatives thereof efficiently undergo inter- and intramolecular aldol type reactions yielding novel types of dyes suitable for the purpose of indicating events or environmental changes.

The term "aldol condensation" is customarily used for a two step chemical reaction between an aldol donor group $C_1$—(C=O)—$C_2$ or its tautomer $C_1$—C(OH)=$C_2$ (i.e. the enol form) and an aldol acceptor $C_3$—(C=O)—Y. The reaction involves (1) the formal addition of the former to the carbonyl group of the latter, thereby forming a carbon-carbon bond between $C_2$ of the donor and the carbonyl carbon atom of the acceptor, and (2) the subsequent elimination of either water ($H_2Z$, Z=O) or of HY, depending on the nature of the rest Y. Equivalent reactions wherein either one of the two carbonylic oxygens is replaced by a heteroatom containing species Z such as NH or S are termed hetero-aldol condensations. In the following, the term "aldol" processes will be intended to also include hetero-aldol processes unless specifically noted otherwise. The general principle of aldol condensations is depicted in Scheme II.

Scheme II: General Illustration of Aldol and Hetero-Aldol Condensations

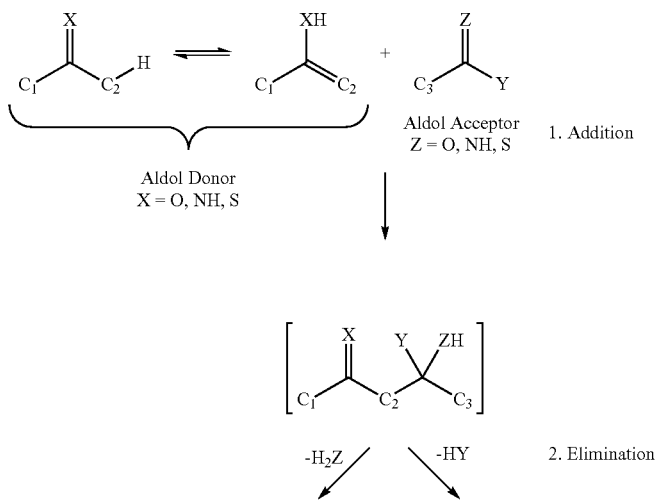

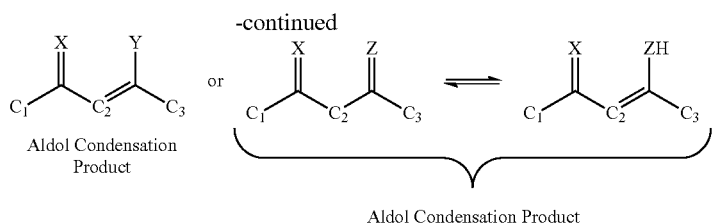

Aldol Condensation Product

Aldol Condensation Product

In the above, if Y represents an effective leaving group (more likely to depart than ZH) such as halogen, cyano, thiocyano, and optionally substituted ammonium, hydroxyl, mercapto, and sulfonyl, the formation of the condensation product involves the elimination of HY (Scheme II, bottom-right structure). Otherwise, the loss of $H_2Z$ (typically water) leads to the alternative condensation product (Scheme II, bottom-left structure).

An introductory overview of intermolecular and intramolecular aldol condensation routes according to the present invention including a comparison with prior art is presented in Scheme III.

Scheme III: Overview and Summary of Invention

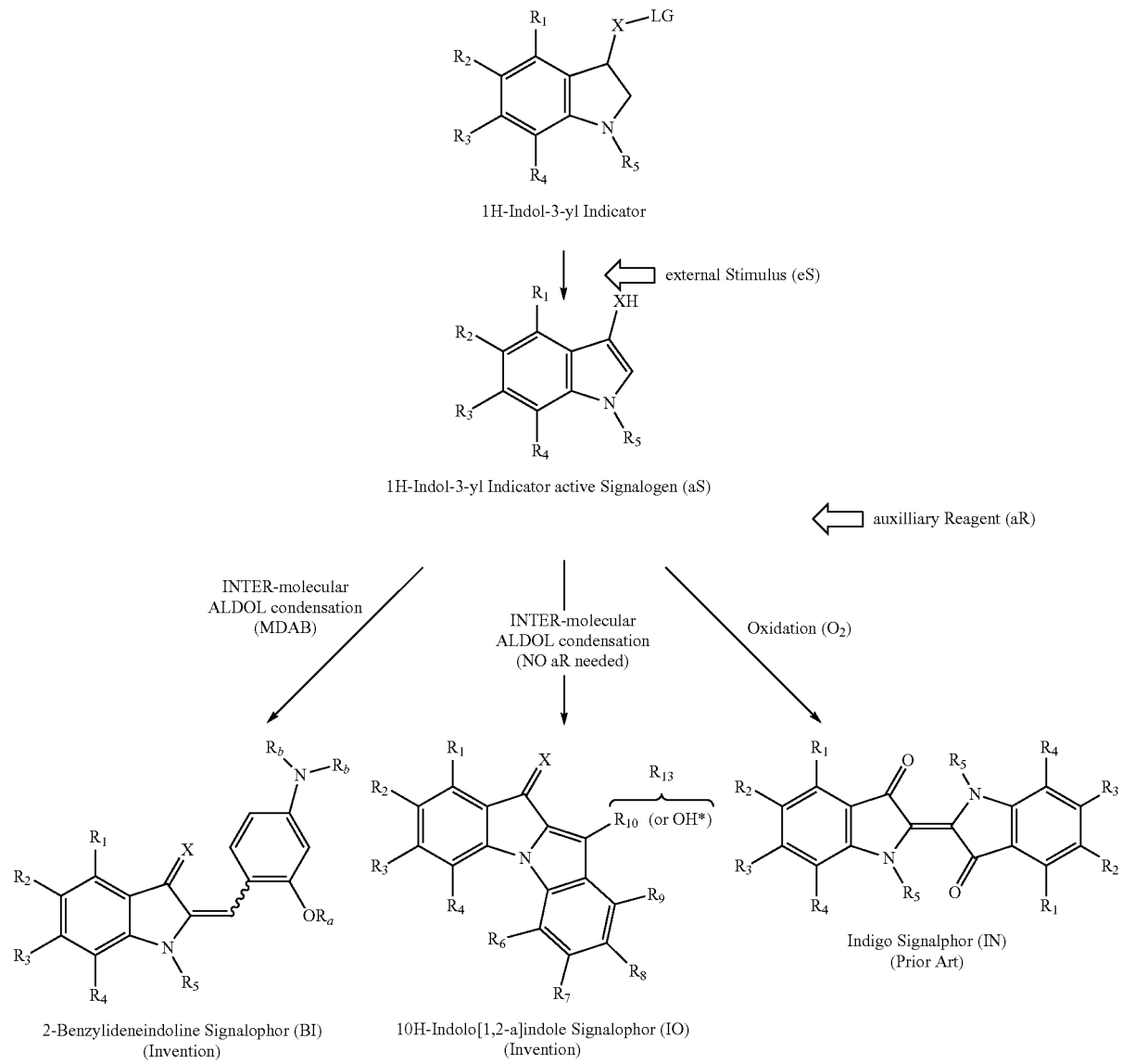

* If $R_{10}$ is a leaving group

In the above $R_a$ and $R_b$ represent hydrogen or C1-4 alkyl, $R_1$, $R_2$, $R_3$, $R_4$, $R_6$, $R_7$, $R_8$, $R_9$ and $R_{10}$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl;

$R_5$ represents either hydrogen, $R_{11}$ or $R_{12}$, wherein $R_{11}$ is

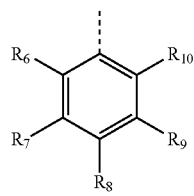

and $R_{12}$ is

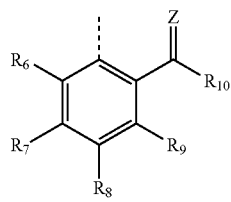

X is selected from O, NH and S, and

MDAB denotes 2-methoxy-4-(N,N-dimethylamino)benzaldehyde.

Hereinabove and in the following, the term "optionally substituted" stands for substitution with a general inert moiety, wherein the term "generally inert" refers herein to any moieties that do not generally interfere with the procedural practices of this invention. Representative examples of generally inert groups or moieties may generally include hydrogen and such organic groups as, for instance, aromatics to include phenyl, alkyl- and/or halogen-substituted phenyl, naphthyl, phenyl-, alkyl- and/or halogen-substituted naphthyl; saturated organic residues to include linear and branched alkyl, for example, methyl, ethyl, propyl to include cyclopropyl, butyl to include cyclobutyl and methyl-substituted cyclopropyl, pentyl to include, e.g., cyclopentyl and methyl-substituted cyclobutyl, hexyl to include, e.g., cyclohexyl, methyl-substituted cyclopentyl and dimethyl or ethyl-substituted cyclobutyl, heptyl to include cycloheptyl, etc., octyl to include cyclooctyl, etc.; halogen-substituted alkyl to include halogen-substituted cycloalkyl, e.g., fluoroalkyl, perfluoroalkyl, e.g., trifluoromethyl, and chloralkyl; alkoxy, e.g., methoxy, aromatic-oxy, e.g., phenoxy; alkylthioxy, e.g., methylthioxy; aromatic-thioxy, e.g., phenylthioxy; acyl, e.g., benzoyl and acetyl, and so forth and the like.

According to one aspect of the invention, an indicator system for detecting an external stimulus, comprises an indicator compound of the general formula

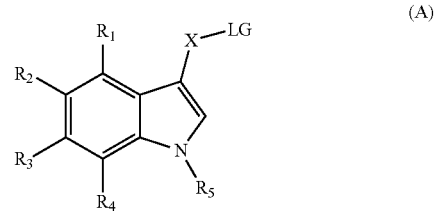

wherein:

X is O, NH or S;

LG is a labile group with the X-LG moiety being susceptible to conversion by action of said external stimulus;

$R_1$, $R_2$, $R_3$ and $R_4$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl;

$R_5$ is either hydrogen or $R_{12}$, wherein $R_{12}$ is

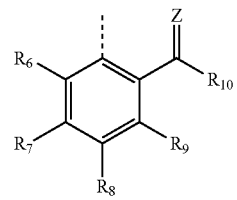

wherein:

Z is O, NH or S;

$R_6$, $R_7$, $R_8$, $R_9$ and $R_{10}$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl;

and wherein, if $R_5$ is hydrogen, the indicator system further comprises an acceptor compound of the general formula

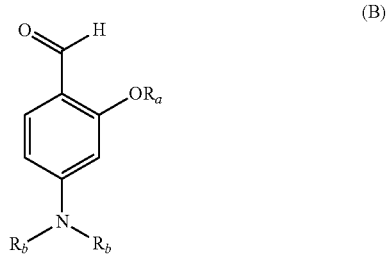

wherein $R_a$ and $R_b$ are independently selected from hydrogen and C1-4 alkyl.

According to one embodiment of the indicator system based on an intermolecular aldol reaction, $R_5$ is hydrogen and the acceptor compound (B) is 2-methoxy-4-(N,N-dimethylamino)benzaldehyde, which has been determined preferable for the intended purpose.

Depending on the application of the indicator system, LG will be chosen from a large variety of possible labile groups, many of which are known in the art. In particular, LG is selected from the group consisting of beta-D-galactopyranoside, tert-butyldimethylsilyloxy (TBDMS), acetate, choline phosphate, alpha-D-glucopyranoside, beta-D-glucuronide sodium salt, N-acetyl-beta-D-galactopyranoside and beta-D-glucopyranoside.

According to one embodiment of the indicator system based on an intramolecular aldol reaction, $R_{10}$ is selected from the group consisting of hydrogen, methyl, methoxy, phenyl, DMP or heteroaryl including, CFur, Fur, NPyr, wherein:

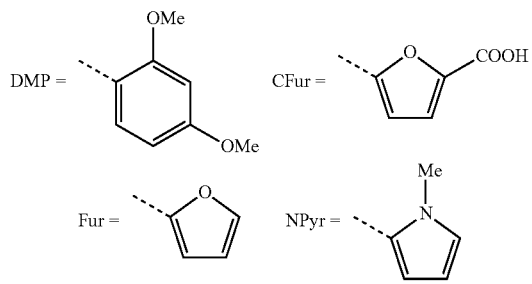

According to a further aspect of the invention, a method of detecting an external stimulus in a region of interest comprises the steps of:

providing the region of interest with an indicator system as defined above; and monitoring for a signal from a signalophore species formed as a consequence of said external stimulus;

The indicator system comprises an indicator compound having a labile group LG bound to a heteroatom X, wherein X is O, NH or S, the X-LG moiety being susceptible to conversion by action of said external stimulus, said conversion leading to formation of an active signalogen species (aS) comprising a moiety wherein X is bound to a carbon atom that is bound to a further carbon atom by a double bond; and said active signalogenic species possessing aldol donor properties thereby promoting events of aldol condensations. Therefore, said active signalogen species (aS) yield signalophore species in the presence of suitable aldol acceptor molecules, said acceptor molecules containing reactive substructures selected from the group of carbonyl, imino and thiocarbonyl.

In a preferred embodiment based on an intermolecular aldol condensation, the acceptor moiety is a carbonyl moiety and is provided by employment of an acceptor compound of the general formula

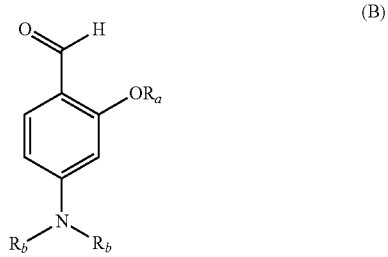

wherein $R_a$, and $R_b$ are independently selected from hydrogen and C1-4 alkyl, thereby providing an indicator system wherein the signalophore species is derived from the general structure of 2-benzylideneindoline (C) as shown below.

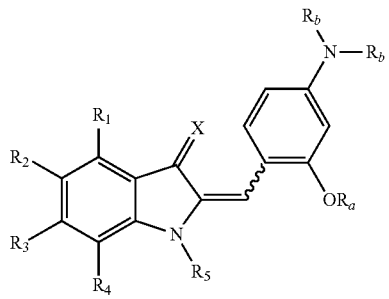

In this embodiment, the acceptor compound (B) is preferably chosen as 2-methoxy-4-(N,N-dimethylamino)benzaldehyde.

In a particularly preferred embodiment based on an intramolecular aldol reaction, the acceptor moiety is a part of said indicator molecule and, if $R_5$ is $R_{12}$, the signalophore species is a 10H-indolo[1,2-a]indole with the structural formula

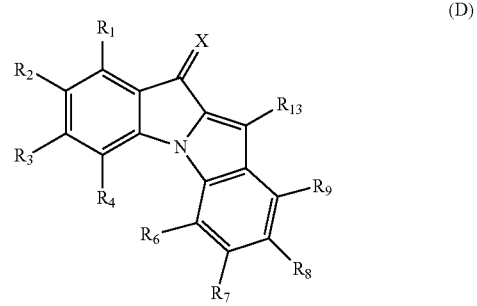

wherein $R_{13}$ is either OH or $R_{10}$.

Note: The numbering of $R_x$ is maintained from indicator to signalophore, but nomenclature changes. Therefore, chemical names of structures (D) are derived of the following numbering Scheme:

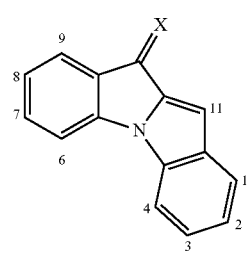

In one embodiment, the method defined hereinabove is carried out under substantially oxygen-depleted conditions.

According to yet another aspect of the invention, there is provided a method of preparing an indicator compound of the general formula (A')

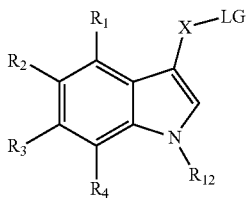

(A')

wherein:

X is O, NH or S;

LG is a labile group with the X-LG moiety being susceptible to conversion by action of said external stimulus;

$R_1$, $R_2$, $R_3$ and $R_4$ are independently selected from the group consisting of hydrogen, C1-4 alkyl; fused or linearly connected aryl; fused or linearly connected heteroaryl; halogen; cyano; nitro; formyl; and optionally substituted amino, carboxy, carbonyl, hydroxy and sulfonyl; and $R_{12}$ is

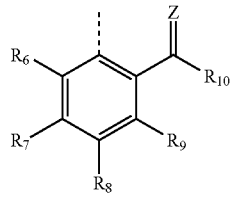

wherein: Z is O, NH or S;

and wherein $R_6$, $R_7$, $R_8$, $R_9$ and $R_{10}$ are independently selected from the group consisting of hydrogen, C1-4 alkyl; fused or linearly connected aryl; fused or linearly connected heteroaryl; halogen; cyano; nitro; formyl; and optionally substituted amino, carboxy, carbonyl, hydroxy and sulfonyl. The method comprises the step of N-arylation of an indoxyl compound of the general formula

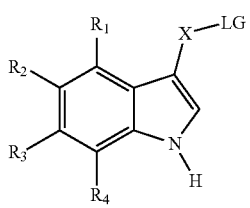

(E)

with a benzene derivative of the general formula

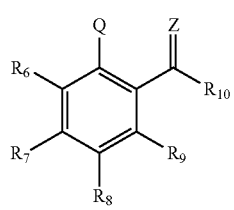

(F)

wherein Q is a leaving group selected from iodo, bromo, triflate and tosylate, preferably iodo or bromo.

According to a further aspect of the invention, there is provided a compound of structural formula (G)

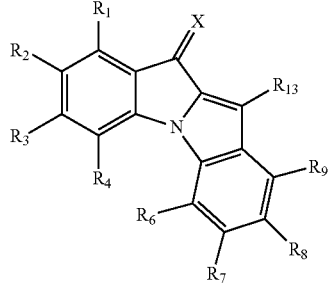

(G)

wherein

X is O, NH or S $R_1$, $R_2$, $R_3$, $R_4$, $R_6$, $R_7$, $R_8$, $R_9$ and $R_{13}$ are independently selected from the group consisting of hydrogen, C1-4 alkyl; fused or linearly connected aryl; fused or linearly connected heteroaryl; halogen; cyano; nitro; formyl; and optionally substituted amino, carboxy, carbonyl, hydroxy and sulfonyl. These compounds (G) are generally classified as indolo[1,2-a]indoles (henceforth also denoted as "IO").

A number of compounds of formula (G) have been mentioned in Rogness and Larock (*Tetrahedron Letters* 2009, 50, 4003-4008), which purportedly was made available on 14 Apr. 2009. Accordingly, a preferred embodiment encompasses the above defined compounds of structural formula (G) with the exception of the compounds listed in Tables 2 and 3 of Rogness and Larock (see claim 14).

According to a further aspect of the invention, a compound of structural formula (G) is used in an indicator system for detecting an external stimulus. Such external stimuli include but are not limited to: Heating or temperature variations; electromagnetic irradiation; applied electric potentials; particular chemical environments such as acidic, alkaline, oxidizing or reducing; presence of particular chemical species such as ions, enzymes, oxygen or oxidizing agents, hydrogen or reducing agents; presence of particular biological species such as viruses, bacteria, fungi, antibodies, cells and cellular organelles, cellular tissue; and even plants, animals and humans as well as organs, bodily fluids, waste or decay thereof.

The indicators or indication systems according to the invention are particularly useful for the purpose of staining cells, microbial colonies or cell tissue.

According to one embodiment, staining or indication with the IO indicators of this invention is used in combination with classic Indox staining or indication.

The manifold uses of IO indicators include but are not limited to staining of bacterial colonies growing in blood cultures, staining of fungal cultures, staining for labelling of individual cells, microbial colonies or cell tissue, staining for the purpose of inducing fluorescence within cellular tissue, colonies of cells, cells, cellular structures or organelles.

Moreover, IO staining is useful for the purpose of imaging static conditions such as size, location, enumeration and spread of benign or malignant cellular tissue, cells, cellular structures, cell walls, membranes, compartments, organelles, antibodies, chromosomes, genomes, genes, plasmids, vectors, nucleic acid strands, proteins or enzymes.

Furthermore, IO staining is useful for the purpose of visualizing dynamic events such as diffusion, growth or decay of benign or malignant cellular tissue, individual cells, cellular structures, organelles, antibodies, chromosomes, genomes, genes, plasmids, vectors, nucleic acid strands, proteins or enzymes, and processes of phagocytosis and pathogenesis.

Still further, IO staining is useful for the purpose of recording, retrieving, storing or archiving digital information.

DETAILED DESCRIPTION OF THE INVENTION

Figure 2:
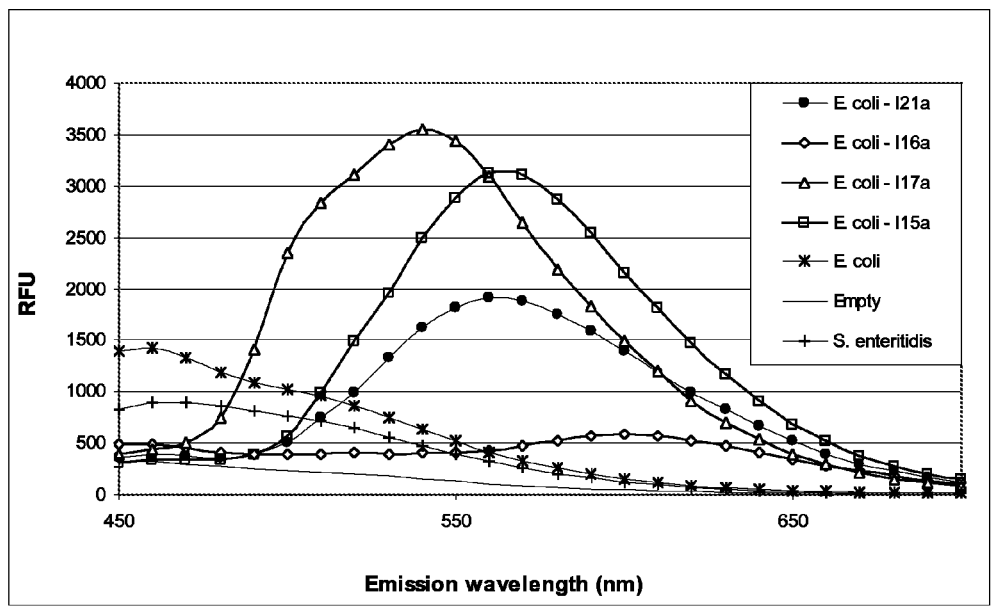
Figure 3:
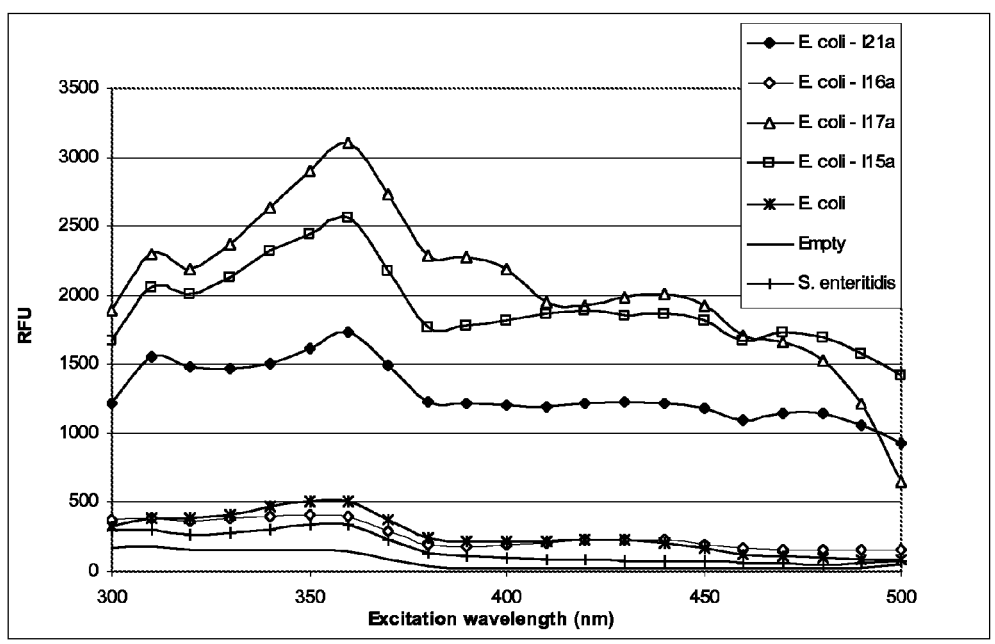

The above mentioned and other features and objects of this invention and the manner of achieving them will become more apparent and this invention itself will be better understood by reference to the following description of various embodiments of this invention taken in conjunction with the accompanying drawings, wherein:

FIG. 1 shows UV/visible absorption spectra (in arbitrary absorbance units "AU") of various 10H-indolo[1,2-a]indole stains (labelled "IOx") and of the corresponding beta-D-galactosidase indicators (labelled "Ixa") (see Tables Ia and Ic for symbol definitions): a) x=14; b) x=16; c) x=19; d) x=21; e) x=17; f) x=15;

FIG. 2 shows fluorescence emission spectra in relative fluorescence units (RFU) for excitation at 360 nm of bacterial colonies stained with various 10H-indolo[1,2-a]indoles (see Table Ia for symbol definitions); and FIG. 3 shows fluorescence excitation spectra in relative fluorescence units (RFU) for emission at 550 nm of bacterial colonies stained with various 10H-indolo[1,2-a]indoles (see Table Ia for symbol definitions).

INTERMOLECULAR ALDOL INDICATORS: MDAB STAINING AND BI INDICATOR SYSTEMS

In this first section a novel method termed MDAB aldol staining is disclosed. The method is based on the discovery that certain 1H-Indox-3-yl activated signalogens and 2-methoxy-4-(N,N-dimethylamino)benzaldehyde (MDAB) auxiliary reagent efficiently undergo an intermolecular aldol condensation to yield dark red to brown colored precipitates suitable for the purpose of indication, thereby providing a novel indicator system significantly expanding upon the current art.

The basis of the MDAB staining technique disclosed here is the discovery that Indox activated signalogens possess significant aldol donor properties and that such properties are highly specific towards certain aldol acceptors, in particular MDAB.

Specifically, it was discovered that widely used commercial Indox Indicators releasing Indoxol activated signalogen 5-bromo-4-chloro-1H-indol-3-ol (Table Ib, aS4) and 5-bromo-6-chloro-1H-indol-3-ol (Table Ib, aS5) produce dark violet stains derived of the 2-benzylideneindolin-2-one parent structure (Table Ic, entries 11-22).

Further, it was recognized that said aldol donor properties of Indox activated signalogens can be moderated or eliminated by masking the X—H moiety in position 3 by replacing the hydrogen with a labile group.

In principle, Indox indicators currently used in indicator systems including oxygen or other oxidizers as auxiliary reagents can be used with MDAB as the auxiliary reagent instead.

However, in practice, not all Indox activated signalogens (or the indicators derived thereof) form efficient aldol donor/acceptor pairs with MDAB: For instance the commonly used 5-bromo-4-chloro-1H-indol-3-ol (Table Ib, aS4) and 5-bromo-6-chloro-1H-indol-3-ol (Table Ib, aS5) activated signalogens proved far more effective than 6-chloro-1H-indol-3-ol (Table Ib, aS3).

For example, O-silylated 5-bromo-4-chloro-1H-indol-3-ol (Table Ia, I4b) was used as a simple indicator for fluoride ions (external stimulus): The silyl group is labile towards fluoride ions in the presence of which the 5-bromo-4-chloro-1H-indol-3-ol (aS4) is set free to react with MDAB to yield mentioned insoluble pink precipitate (Table Ic, BI4).

In a second example, a blend of the commercial reagent 5-bromo-4-chloro-1H-indol-3-yl-beta-D-galactopyranoside (Table Ia, I4a) and MDAB yielded said pink dye upon incubation with beta-D-galactosidase in the absence of oxygen while it is well known in the art that I4a by itself depends on the presence of oxygen or an oxidizer for functioning as an indicator.

Further, Indox activated signalogens 3-aminoindole or 3-mercaptoindole (Table Ib, aS6 and aS7) were tested for their aldol donor properties. While 3-aminoindole failed to yield any aldol product with MDAB (Table Ic, BI6), 3-mercaptoindole and MDAB did produce the characteristic pink dye (BI7) under strongly acidic conditions (Tables IIa-c, entries 14 and 15).

Indox indicator systems tested are listed in Tables IIa (aerobic, no MDAB), IIb (aerobic, MDAB) and IIc (anaerobic, MDAB).

Further elaboration revealed that Indox/MDAB indication can be used to stain microbial colonies by using characteristic biomarker enzymes as external stimulus. Importantly, MDAB showed no toxic effect on microbial cell growth in these studies. Results are summarized in Table III.

For example, microbial plating media containing the I4a/MDAB indicator system were incubated in the presence and absence of atmospheric oxygen: While at atmospheric concentration of oxygen the formation of turquoise indigo (Table Ic, IN4) dominated, stained colonies appeared pink due to the formation of BI4 (Table Ic) under micro-anaerobic or anaerobic conditions due to the effect of MDAB staining (Table III, entry 10).

In general, commercially available Indox indicators derived of aS4 or aS5 in combination with 2 to 4 equivalents of MDAB were found to be the preferable indicator systems for staining of microbial cultures under anaerobic conditions. Indicators I9a, I10a, I11a, and I12a in combination with MDAB represent indicator systems that are effective under aerobic conditions (Table III, entries 26-37): It appears that the formation of indigo from N-arylated Indox activated signalogens is inefficient and that the intramolecular aldol condensation dominates instead.

INTRAMOLECULAR ALDOL INDICATORS: IO INDICATOR SYSTEMS

The MDAB staining disclosed above is based on the unique match of an aldol donor and a MDAB aldol acceptor pair. In the following, it is disclosed that a similar effect can be achieved by chemically linking aldol donor and acceptor.

It is well known in the art that intramolecular ring-closure reactions including intramolecular aldol reactions proceed at high rates especially if 5- or 6-membered rings are formed in the process. Therefore, the concept was developed to connect aldol donor and acceptor such that the spatial arrangement of donor and acceptor moieties would favor the event of an intramolecular aldol condensation.

In analogy to the above described MDAB staining, untimely occurrence of the aldol condensation can be prevented by the masking effect of a labile group conjugated to the aldol donor. A spontaneous aldol condensation takes place after departure or modification (e.g. chemical reduction) of the labile group in response to an external stimulus.

The design of an intramolecular aldol indicator requires the aldol acceptor to be attached to the donor by means of a chemical structure linking the $C_3$ atom of the aldol acceptor (Scheme II). Traditional IN Indox indicators provide a perfect anchor site for the linker: The indole nitrogen. Said linking may include one or two sequentially arranged atoms $C_1$ and $C_2$ as shown in Scheme IV. In the former case a formal intramolecular aldol condensation would yield a 5-membered ring whereas in the latter case it would yield a 6-membered ring in the signalophore structure.

Scheme IV: Optional Design of Intramolecular Indox Aldol Indicators

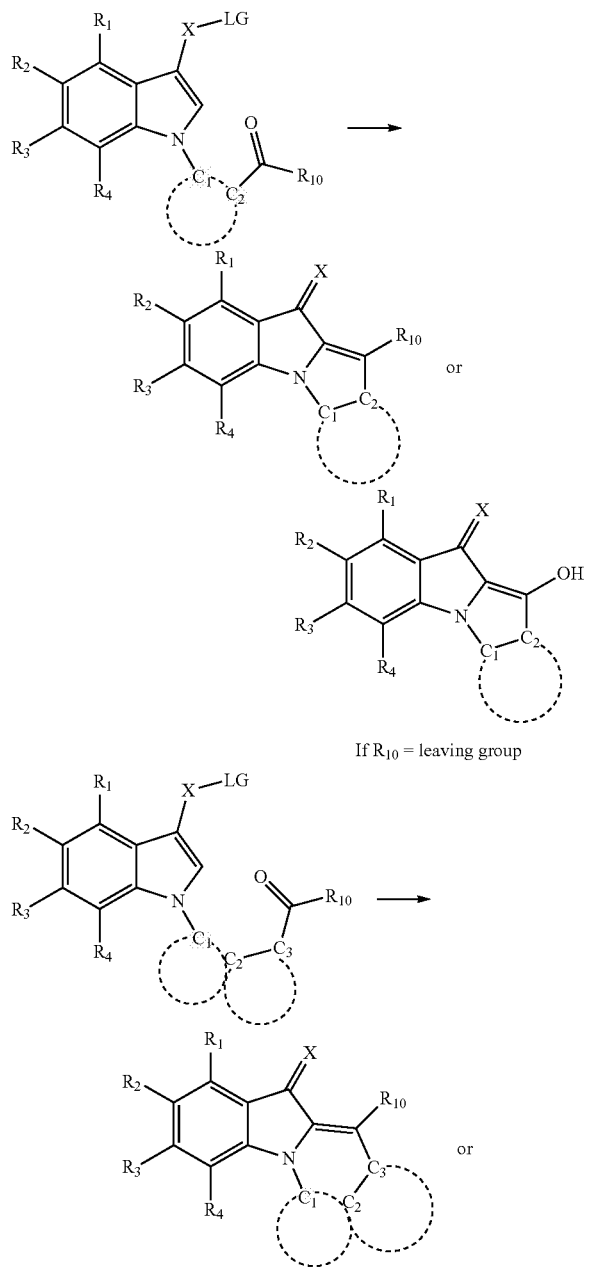

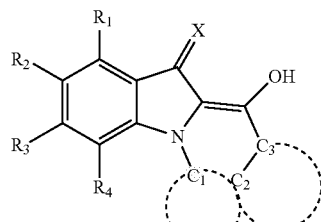

If $R_{10}$ = leaving group $C_1$, $C_2$, $C_3$ represent carbon atoms optionally substituted by hydrogen; C1-4 alkyl; fused or linearly connected aryl; fused or linearly connected heteroaryl; halogen; cyano; thio-cyano; nitro; nitroso; formyl; and optionally substituted amino, carboxy, carbonyl, hydroxyl, mercapto and sulfonyl $R_1$, $R_2$, $R_3$, $R_4$ are selected from the group consisting of hydrogen, C1-4 alkyl; fused or linearly connected aryl; fused or linearly connected heteroaryl; halogen; cyano; thiocyano; nitro; nitroso; formyl; and optionally substituted amino, carboxy, carbonyl, hydroxyl, mercapto and sulfonyl X is selected from O, NH and S.

The aldol acceptor is preferably chosen as an aromatic carbonyl compound, (hence $C_1$ and $C_2$ represent members of an aromatic ring) such that an intramolecular aldol condensation would result in the formation of an extended conjugated system thereby providing the signalophore with desirable optical properties.

Due to the kinetic advantage of an intramolecular aldol reaction donor and acceptor molecules do not need to form a matching donor/acceptor pair such as Indox/MDAB.

Of the many synthetic routes explored to achieve the desired linking between donor and acceptor structures, N-arylation was discovered to be the preferred method.

N-arylation is a well established synthetic method. For example it is well known in the art that indoles readily react with iodobenzene to produce N-phenylindoles in high yields.

For instance 3-indolyl-beta-D-galactoside (I1a) was reacted with derivatives of Iodobenzene in DMF in the presence of a copper catalyst to yield the corresponding 1-phenyl-3-indolyl-beta-D-galactopyranoside (I8a). This is remarkable since the labile group was chosen to be a carbohydrate and said carbohydrate was used without chemical protection.

In analogy, novel aldol type indicators were obtained in one simple step and in high yields by N-arylation of the corresponding commercially 1H-indox-3-yl indicators under a variety of conditions including traditional Ullmann type copper catalysis or newer variants thereof such as recently published by Taillefer et al. (Efficient Iron/Copper Co-Catalyzed Arylation of Nitrogen Nucleophiles. *Angew. Chem., Int. Ed.* 2007, 46, 934-936).

Scheme V: Preparation of Intramolecular Indox Aldol Indicators

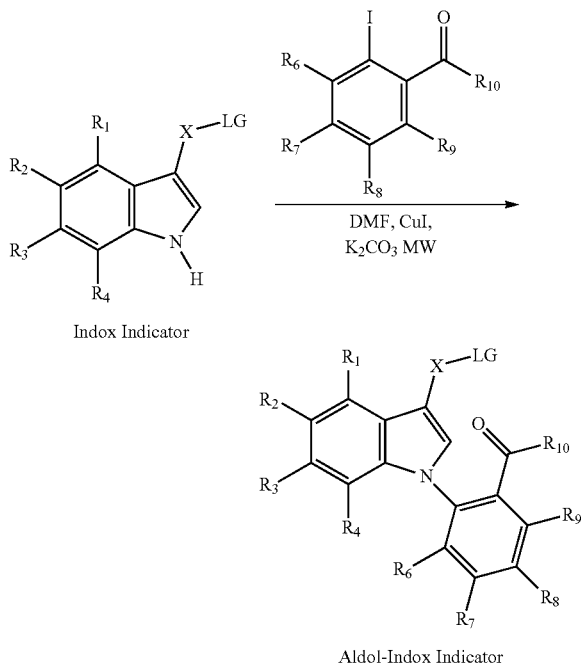

Indox Indicator

Aldol-Indox Indicator $R_1$, $R_2$, $R_3$, $R_4$, $R_6$, $R_7$, $R_8$, $R_9$ and $R_{10}$ are selected from the group consisting of hydrogen, C1-4 alkyl; fused or linearly connected aryl; fused or linearly connected heteroaryl; halogen; cyano; nitro; formyl and optionally substituted amino, carboxy, carbonyl, hydroxy and sulfonyl X is selected from O, NH and S.

The concept was demonstrated to be of general validity: A significant number of commercial Indox indicators were successfully conjugated to a range of aromatic aldol acceptors by means of the above mentioned N-arylation techniques thereby providing simple, efficient and generic entry into a novel family of indicators (Table Ia, entries 15-46).

Novel indicators generally did respond to suitable external stimuli as anticipated (Tables IVa-c). Removal of the labile masking group triggered the postulated aldol condensation.

Ketones, (acting as internal acceptors), generally yielded brightly colored insoluble dyes with colors ranging from yellow, orange, red to brown. Occasionally, intense green fluorescence of transient nature was observed which is characteristic of 3-indoxyl species such as are represented by the aS species, which in the postulated process of aldol condensation would be of transient nature as well.

Esters (acting as internal acceptors), in contrast, produced persistently green fluorescent dyes (Table Ic: IO10, IO11, IO12) freely soluble in water above pH 5.

Upon further acidification said dyes formed orange colored non-fluorescent precipitates from aqueous solutions. This process was found to be completely reversed by the addition of base. Evidently, said dyes are highly acidic in nature and highly fluorescent in deprotonated form.

Generally, all of these dyes are derived of a parent indolo [1,2-a]indole (Table Ic, entries 23-46). The indolo[1,2-a]indole structure formally consists of two indoles sharing the nitrogen and the adjacent pyrrole carbon. Despite the appeal and simplicity of this structure, indolo[1,2-a]indoles (henceforth denoted "IO") appear to be novel.

In FIG. 1 absorption spectra of various IO stains are overlaid with the ones of the corresponding indicators. The graphs illustrate that IO absorption between 300 and 400 nm and 400 and 500 nm are both lacking in the corresponding indicators and therefore provides useful detectable signal.

For example incubation of the N-benzophenone conjugate of 6-chloroindoxyl-beta-D-galactoside (I21a) with beta-D-galactosidase for 24 h produced a bright yellow precipitate which was collected, washed with water, dried and characterized as 7-chloro-11-phenyl-10H-indolo[1,2-a]indol-10-one (Table Ic, IO21), which corresponds to the expected aldol condensation product.

IO staining was tested on plating media inoculated with various bacterial beta-D-galactosidase positive strains. Colonies of beta-D-galactosidase positive strains of E. coli appeared yellow to red depending on the indicator used while beta-galactosidase negative Salmonella colonies appeared no different in the presence or absence of tested galactosidase indicators (Tables IVa and IVb).

Further, IO staining was tested on different bacteria producing a variety of different biomarker enzymes (Table IVc).

It should be noted that IO staining and classical indigo (IN) staining can be usefully combined, thereby extending the color scheme (Table IVd): For instance indicator I4h was used in combination with I21a in a dual plating media assay staining beta-D-glucosidase and beta-D-galactosidase bacterial species concurrently. While the strains positive for the former biomarker stained blue and strains positive for the latter stained yellow, strains positive for both enzymes stained green (mixture of blue and yellow).

It is well known that colonial growth of facultative anaerobic microbial species is relatively slow under anaerobic conditions. Due to the prolonged time of incubation, indicator systems used for the purpose to stain anaerobically cultured colonies must provide excellent localization (or minimal diffusion). From the experimental data shown in Table IVe it can be concluded that some IO indicator systems are excellently suited for said purpose. At the same time the data illustrate the failure of classic IN staining (I4a) and demonstrate that accumulation of corresponding activated signalogen caused by the absence of matching auxiliary reagent (e.g. oxygen) partially inhibits microbial growth.

Blood cultures represent a common and essential tool in clinical microbiology. Staining of microbial colonies on agar plates is obscured by the dark color and lack of translucency of Blood Agar plates. Therefore, IO indicator systems have been evaluated for use on Blood Agars (Table IVf). The experiments produced very favorable results: IO signalophores provided excellent optical contrast and localization.

Staining of fungal cultures is another important area of application for biological indicator systems. For this purpose, an IO indicator system has been devised which is labile towards the action of D-galactosamidase, a biomarker enzyme for the notorious pathogen Candida albicans. Although colonial growth under the culturing conditions chosen was modest, in the presence of I21g fungal colonies producing a matching external stimulus turned bright yellow and became readily distinguishable by the human eye (Table IVg).

All of the plating media listed in Tables IVa-f were inspected under illumination at 366 nm before, during and after incubation. Thereby it was discovered that 10H-indolo [1,2-a]indol-10-ones are fluorescent in the solid state and that the effect of fluorescence was maintained by IO stained colonies: Generally, at 366 nm plating media (except for Blood Agar plates) containing IO indicator systems provide a bluish background on which unstained colonies appear as faint shadows, whereas IO stained colonies stand out in bright colors ranging from yellow-green to red-brown providing excellent visual contrast and high sensitivity.

The blood ingredients of Blood Agar plates effectively quench fluorescence. Therefore, plates appear black under 366 nm UV light. Interestingly, fluorescence of IO stains dispersed in colonies growing on Blood Agar plates remains undisturbed and provides spectacular illumination of colonies against the black background (Table IVf).

In the following, the discovery that IO stains induced persistent fluorescence within microbial colonies was further elaborated: Fluorescence could be quantified in colonies harvested from plating media by using a standard plate reader. Intensity and wavelength of the emission was strongly dependent on the type of indicator system used. Data collected in various emission scans are presented in FIG. 2.

The corresponding samples were also subjected to excitation scans recording emission at 550 nm (FIG. 3). Interestingly, IO stains were found to be excitable between 300 and 500 nm, which is an unusually broad range. Clearly, the bright shining colors of many IO stains are due to the effect of excitation (optical brightening) by ambient light.

In an extension of the above, it was also recognized that standard liquid culturing of E. coli in the presence of IO indicator systems yielding fluorescent signalophores provides a novel method for fluorescence labeling of individual cells: In samples taken from said culture, individual cells of E. coli became clearly visible under a standard fluorescence microscope.

IO staining, therefore, may provide a simple and economic method for live cell labeling, which commonly relies on the elaborate application of fluorescent antibodies or genetic vectors that encode fluorescent proteins.

Finally, the scope of the invention was further explored by evaluation of structural variations of IO indicator systems which are derived of the nitrogen and sulfur analogues of 1-aryl-1H-indol-3-ol activated signalogen.

Scheme VI: Hetero Atom Linked Labile Groups

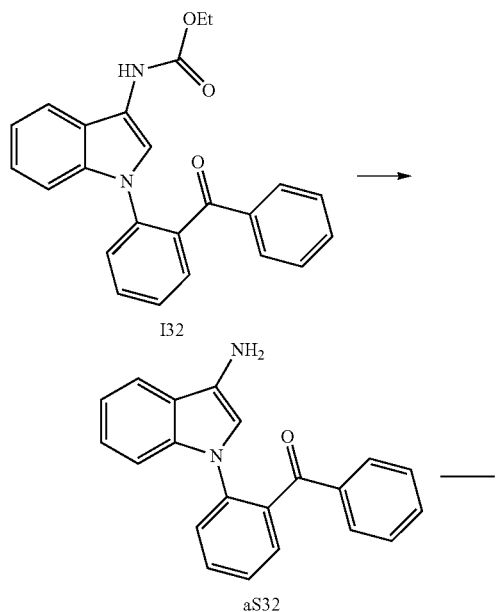

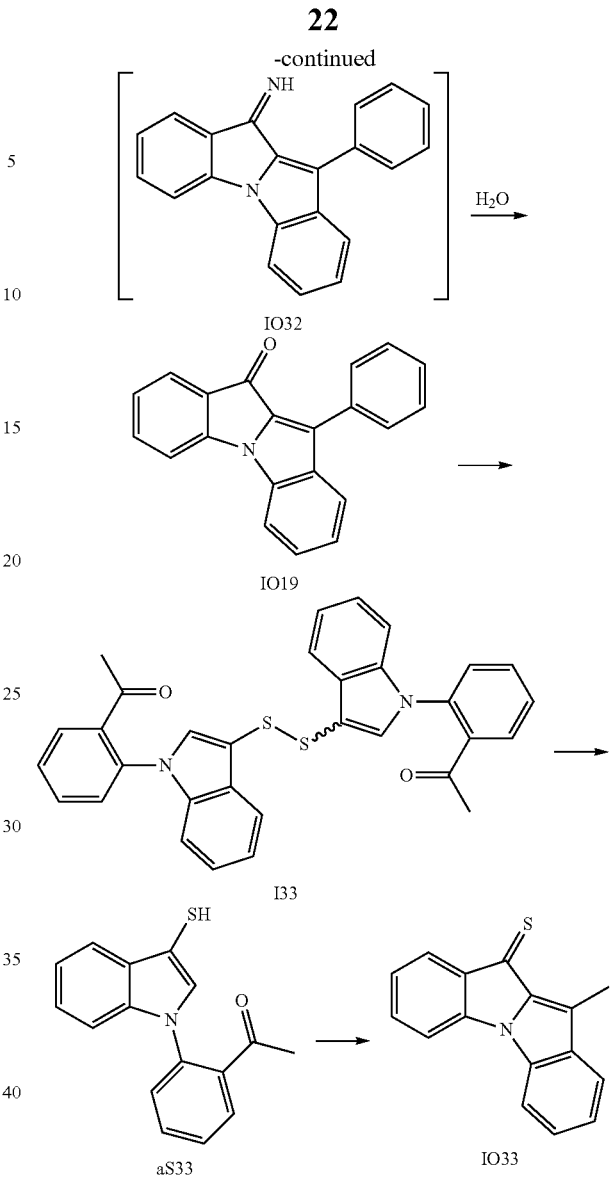

For said purpose, 1-(2-benzoylphenyl)-1H-indol-3-yl ethyl carbamate (I32) was subjected to alkaline and pig liver esterase catalyzed hydrolysis. A yellow precipitate was isolated, which, by means of comparison with a reference sample, was identified as 11-phenyl-10H-indolo[1,2-a]indol-10-one (IO19) rather than the expected 11-phenyl-10H-indolo[1,2-a]indol-10-imine (IO32). A plausible explanation is provided by the possible hydrolysis of the imino group under the conditions of assay which would transform IO32 to the observed IO19. Independent of the mechanism of action and its practical relevance, the experiment demonstrates that in principle the concept can be extended to include indicator systems where the labile group is attached to a nitrogen atom. The relevance of this finding lies in a manifold of important biological applications which base on the detection of aminopeptidase activity and the fact that no useful precipitating indicator systems are available in the current state of the art.

In a second example, the oxidized form of 1-(2-acetylphenyl)-1H-indol-3-thiole (aS33), bis[1-(2-acetylphenyl)-1H-indol-3-yl]-disulfane (I33) was subjected to reduction of the S—S bridge by TCEP, a standard reagent used in protein biochemistry, thereby releasing aS33. While no detectable signal was observed at neutral conditions, the assay solution turned to yellow, thereby clearly indicating the event of disulfide reduction, when alkaline conditions where used. This example underlines the fact that IO indicator systems represent a generic and highly versatile concept. It also serves to emphasize that the IO indicator systems are by no means limited to detect external stimuli associated with enzymatic activity. The many examples presented herein below are not to be taken as a limitation of this invention but merely reflect the practical field the inventors are engaged in.

EXAMPLES

Example 1

Preparation of Indicators I8 to I31 by N-arylation of I1 to I4 (Table Ia)

Note: Aromatic iodo compounds were either commercially available or prepared by standard Friedel-Crafts acylation with ortho-iodobenzoic acid. 2-(2-Iodobenzoyl)-N-methylpyrrole was prepared in analogy to Carson et al. (WO2000048584), 2-(2-iodobenzoyl)furan and 2-(2-iodobenzoyl)-5-carboxyfuran in analogy to Garland et al. (DE2557956) and 4-chloro-2-iodobenzophenone according to Gabbutt et al. (*Tetrahedron* 2006, 62, 737-745). 1-Acetyl-2-iodo-4-methoxybenzene and 1-benzoyl-2-iodo-4-methoxybenzene were obtained by Friedel-Crafts reaction of 3-iodoanisol in the presence of aluminium chloride.

Experiments were carried out in a Synthos 3000 multimode microwave reactor from Anton Paar GmbH. The following parameters were adjusted: P(max)=1400 W; T(IR-max)=200° C.; Drive: rotation; Stirrer: 3; p-rate=2.0 bar/s. Ramp-time=2 min (130° C.) and hold-time=180 min (130° C.). A PTFE-liner (100 ml) fitted with a Teflon-coated stirring bar was used as the reaction vessel. In a typical procedure a mixture of 5 mMol of 1H-Indol-3-yl indicator, 10 mMol of the corresponding aryl iodide, 5 mMol potassium carbonate, 0.5 mMol copper(I) iodide in 20 ml of DMF was subjected to MW irradiation. The product mixture was filtered and the solids washed with 10 ml ethanol. The filtrate was evaporated to dryness and the crude product purified by flash chromatography [e.g. silica gel, toluene/ethanol (5:1)].

IR spectra were recorded as neat solids on a Perkin-Elmer FT-IR spectrophotometer, model Spectrum ONE (v [cm$^{-1}$]). $^1$H- and $^{13}$C-NMR spectra were recorded at 298 K on Brucker AVANCE-400 [400.13 MHz ($^1$H), 100.61 MHz ($^{13}$C)] spectrometer (δ [ppm], J [Hz]).

1-Phenyl-1H-indol-3-yl-beta-D-galactopyranoside (I8a)

Yield: 628 mg (34%); TLC [toluene/ethanol (5:3)]: R$_f$ 0.47.
$^1$H-NMR [DMSO-d$_6$]: 7.73-7.71 (m, 1H); 7.56-7.54 (m, 5H); 7.42 (s, 1H); 7.37-7.32 (m, 1H); 7.23-7.19 (m, 1H); 7.14-7.10 (m, 1H); 5.30-5.28 (d, 1H); 4.89-4.87 (d, 1H); 4.74-4.72 (d, 1H, J=7.8 Hz); 4.71-4.69 (d, 1H); 4.54-4.53 (d, 1H); 3.72-3.66 (m, 2H); 3.61-3.56 (m, 3H); 3.48-3.41 (m, 2H).
$^{13}$C-NMR [DMSO-d$_6$]: 139.18, 139.01, 132.28, 129.73, 125.73, 123.33, 122.99, 121.42, 119.60, 118.19, 113.35, 110.17, 104.22, 75.71, 73.33, 70.39, 68.23, 60.54.

6-Chloro-1-phenyl-1H-indol-3-yl-beta-D-galactopyranoside (I9a)

Yield: 560 mg (28%); TLC [toluene/ethanol (5:3)]: R$_f$ 0.43.
$^1$H-NMR [DMSO-d$_6$]: 7.72-7.70 (m, 1H); 7.58-7.56 (m, 4H); 7.52-7.51 (m, 1H); 7.45 (s, 1H); 7.41-7.37 (m, 1H); 7.16-7.13 (m, 1H); 5.30-5.29 (d, 1H); 4.89-4.87 (d, 1H); 4.72-4.71 (d, J=7.8 Hz, 1H); 4.69-4.67 (m, 1H); 4.54-4.53 (d, 1H); 3.71-3.63 (m, 2H); 3.59-3.55 (m, 3H); 3.43-3.39 (m, 1H).
$^{13}$C-NMR [DMSO-d$_6$]: 138.75, 138.55, 132.48, 129.85, 127.82, 126.29, 123.56, 120.11, 119.99, 119.65, 114.43, 109.81, 104.18, 75.73, 73.23, 70.30, 68.18, 60.50.

1-[2-(Methoxycarbonyl)phenyl]-1H-indol-3-yl-beta-D-galactopyranoside (I10a)

Yield: 496 mg (23%); TLC [toluene/ethanol (5:3)]: R$_f$ 0.41.
$^1$H-NMR [DMSO-d$_6$]: 7.89-7.87 (m, 1H); 7.77-7.69 (m, 2H); 7.56-7.52 (m, 2H); 7.25-7.02 (m, 4H); 5.27-5.26 (br. d, 1H); 4.87 (br. s, 1H); 4.67-4.65 (d, J=7.8 Hz, 1H); 4.65-4.64 (br. d, 1H); 4.53-4.52 (br. d, 1H); 3.71-3.63 (m, 2H); 3.58-3.49 (m, 3H); 3.44-3.39 (m, 1H).
$^{13}$C-NMR [DMSO-d$_6$]: 166.38, 138.94, 137.68, 133.77, 133.16, 130.73, 128.21, 128.04, 127.41, 122.79, 120.96, 119.41, 118.16, 114.62, 109.39, 104.54, 75.65, 73.34, 70.50, 68.16, 60.43, 52.24.

6-Chloro-1-[2-(methoxycarbonyl)phenyl]-1H-indol-3-yl-beta-D-galactopyranoside (I11a)

Yield: 526 mg (23%); TLC [toluene/ethanol (5:3)]: R$_f$ 0.41.
$^1$H-NMR [DMSO-d$_6$]: 7.91-7.89 (m, 1H); 7.78-7.74 (m, 1H); 7.70-7.68 (m, 1H); 7.60-7.55 (m, 2H); 7.19 (s, 1H); 7.10-7.08 (m, 1H); 6.98 (d, 1H); 4.65-4.63 (d, J=7.8 Hz, 1H); 3.66-3.61 (m, 2H); 3.56-3.51 (m, 3H); 3.48 (s, 3H); 3.42-3.39 (m, 1H).
$^{13}$C-NMR [DMSO-d$_6$]: 165.94, 138.58, 136.99, 134.01, 133.29, 130.77, 128.25, 128.14, 127.94, 127.52, 119.68, 119.62, 119.58, 115.73, 109.12, 104.46, 75.64, 73.19, 70.35, 68.05, 60.34, 52.23.

5-Bromo-4-chloro-1-[2-(methoxycarbonyl)phenyl]-1H-indol-3-yl-beta-D-galactopyranoside (I12a)

Yield: 572 mg (21%); TLC [toluene/ethanol (5:3)]: R$_f$ 0.41.
$^1$H-NMR [DMSO-d$_6$]: 7.93-7.91 (m, 1H); 7.81-7.74 (m, 1H); 7.62-7.58 (m, 1H); 7.54-7.52 (m, 1H); 7.37-7.34 (m, 1H); 7.27 (s, 1H); 6.87-6.84 (m, 1H); 4.70-4.68 (d, J=7.8 Hz, 1H); 3.70-3.63 (m, 2H); 3.54-3.52 (m, 3H); 3.49 (s, 3H); 3.43-3.39 (m, 1H).
$^{13}$C-NMR [DMSO-d$_6$]: 165.56, 139.53, 137.85, 136.76, 133.66, 133.40, 130.88, 128.63, 128.38, 128.20, 126.60, 123.67, 116.21, 112.73, 110.12, 103.91, 75.59, 73.46, 70.31, 68.05, 60.30, 52.33.

1-(2-Formylphenyl)-1H-indol-3-yl-beta-D-galactopyranoside (I13a)

Yield: 443 mg (22%); TLC [toluene/ethanol (5:3)]: R$_f$ 0.42.
$^1$H-NMR [DMSO-d$_6$]: 9.64 (s, CHO); 8.01-7.99 (m, 1H); 7.89-7.85 (m, 1H); 7.75-7.73 (m, 1H); 7.66-7.59 (m, 2H); 7.45 (s, 1H); 7.26-7.09 (m, 3H); 5.29-5.27 (br. d, 1H); 4.89-4.88 (br. d, 1H); 4.75-4.73 (d, J=7.8 Hz, 1H); 4.63-4.61 (br. d, 1H); 4.54-4.53 (br. d, 1H); 3.71-3.65 (m, 2H); 3.54 (br. s, 3H); 3.43-3.36 (m, 1H).

¹³C-NMR [DMSO-d₆]: 189.40, 141.07, 139.27, 135.46, 135.02, 131.03, 128.37, 127.99, 127.91, 123.37, 120.92, 119.88, 118.24, 115.60, 109.66, 104.13, 75.61, 73.26, 70.36, 68.09, 60.35.

1-(2-Acetylphenyl)-1H-indol-3-yl-beta-D-galactopyranoside (I14a)

Yield: 1.20 g (60%); TLC [toluene/ethanol (5:3)]: $R_f$ 0.38.
¹H-NMR [DMSO-d₆]: 7.75-7.70 (m, 3H); 7.59-7.54 (m, 2H); 7.21 (s, 1H); 7.18-7.09 (m, 2H); 7.05-7.03 (m, 1H); 5.29-5.27 (br. d, 1H); 4.87-4.85 (br. d, 1H); 4.69-4.67 (d, J=7.8 Hz, 1H); 4.63-4.61 (br. s, 1H); 4.52-4.51 (br. d, 1H); 3.71-3.62 (m, 2H); 3.58-3.50 (m, 3H); 3.46-3.39 (m, 1H); 1.82 (s, 3H).
¹³C-NMR [DMSO-d₆]: 200.12, 139.13, 137.09, 136.59, 133.75, 132.61, 129.14, 127.86, 127.69, 123.10, 120.72, 119.64, 118.16, 114.58, 109.56, 104.24, 75.56, 73.23, 70.38, 68.05, 60.28, 28.28.

1-(2-Acetylphenyl)-4-chloro-1H-indol-3-yl-beta-D-galactopyranoside (I15a)

Yield: 1.09 g (49%); TLC [toluene/ethanol (5:3)]: $R_f$ 0.41.
¹H-NMR [DMSO-d₆]: 7.79-7.72 (m, 2H); 7.62-7.58 (m, 1H); 7.54-7.53 (m, 1H); 7.29 (s, 1H); 7.12-7.07 (m, 2H); 6.97-6.92 (m, 1H); 5.02-5.01 (br. d, 1H); 4.86-4.85 (br. d, 1H); 4.77-4.75 (d, J=7.8 Hz, 1H); 4.63 (br. s, 1H); 4.55-4.54 (br. d, 1H); 3.72-3.65 (m, 2H); 3.55 (br. s, 3H); 3.46-3.40 (m, 1H); 1.92 (s, 3H).
¹³C-NMR [DMSO-d₆]: 199.75, 138.48, 137.14, 136.00, 135.01, 132.72, 129.27, 128.24, 128.07, 124.21, 123.63, 120.41, 117.24, 114.95, 108.65, 103.51, 75.53, 73.54, 70.39, 68.07, 60.27, 28.40.

1-(2-Acetylphenyl)-6-chloro-1H-indol-3-yl-beta-D-galactopyranoside (I16a)

Yield: 0.96 g (44%); TLC [toluene/ethanol (5:3)]: $R_f$ 0.46.
¹H-NMR [DMSO-d₆]: 7.78-7.70 (m, 3H); 7.62-7.57 (m, 2H); 7.25 (s, 1H); 7.17-7.12 (m, 1H); 7.05-7.04 (m, 1H); 5.30-5.29 (br. d, 1H); 4.88-4.86 (br. d, 1H); 4.68-4.66 (d, J=7.7 Hz, 1H); 4.63-4.61 (br. s, 1H); 4.52-4.51 (br. d, 1H); 3.70-3.62 (m, 2H); 3.56-3.50 (m, 3H); 3.42-3.39 (m, 1H); 1.91 (s, 3H).
¹³C-NMR [DMSO-d₆]: 199.95, 138.83, 137.06, 135.83, 133.97, 132.71, 129.29, 128.18, 127.85, 125.23, 120.04, 119.70, 119.49, 115.73, 109.38, 104.25, 75.62, 73.17, 70.33, 68.04, 60.29, 28.45.

1-(2-Acetylphenyl)-5-bromo-4-chloro-1H-indol-3-yl-beta-D-galactopyranoside (I17a)

Yield: 0.61 g (23%); TLC [toluene/ethanol (5:3)]: $R_f$ 0.42.
¹H-NMR [DMSO-d₆]: 7.83-7.80 (m, 1H); 7.77-7.73 (m, 1H); 7.64-7.60 (m, 1H); 7.56-7.53 (m, 1H); 7.41-7.39 (m, 1H); 7.35 (s, 1H); 6.92-6.90 (m, 1H); 5.07-5.06 (br. d, 1H); 4.87-4.86 (br. d, 1H); 4.74-4.72 (d, J=7.7 Hz, 1H); 4.62 (br. s, 1H); 4.55-4.53 (br. d, 1H); 3.71-3.64 (m, 1H); 3.55 (br. s, 3H); 3.47-3.39 (m, 2H).
¹³C-NMR [DMSO-d₆]: 199.56, 138.04, 137.03, 135.44, 133.60, 132.77, 129.38, 128.54, 128.33, 126.96, 123.77, 118.55, 116.27, 113.05, 110.39, 103.72, 75.57, 73.44, 70.32, 68.06, 60.27, 28.50.

1-(2-Acetyl-5-methoxyphenyl)-6-chloro-1H-indol-3-yl-beta-D-galactopyranoside (I18a)

Yield: 1.6 g (65%); TLC [toluene/ethanol (4:1)]: $R_f$ 0.36.
FT-IR: 3459m, 2964w, 2927w, 2867w, 1665s, 1601s, 1569m, 1497m, 1471s, 1451s, 1372s, 1267s, 1220s, 1140s, 1081s, 1053s, 1020s, 975m, 945m, 880m, 800m, 735m, 696m.
¹H-NMR [DMSO-d₆]: 7.80 (d, J=8.7, 1 arom. H); 7.71 (d, J=8.5, 1 arom. H); 7.28 (s, 1 arom. H); 7.17-7.11 (m, 2 arom. H); 7.07 (d, J=2.5, 1 arom. H); 7.06 (d, J=1.7, 1 arom. H); 5.30 (d, J=5.0, OH); 4.87 (d, J=5.8, OH); 4.68 (d, J=7.8, H—C(1)$_{Gal}$); 4.64 (t, J=5.2, OH); 4.52 (d, J=4.7, OH); 3.88 (s, OCH₃); 3.70 (t, J=4.0, H—C(4)$_{Gal}$); 3.65 (m$_c$, 1H—C$_{Gal}$); 3.58-3.51 (m, 3H—C$_{Gal}$); 3.48-3.39 (m, 1H—C$_{Gal}$); 1.86 (s, CH₃).
¹³C-NMR [DMSO-d₆]: 197.86 (s, C=O); 162.54 (s, C—OCH₃); 138.79, 138.18, 134.01 (3 s); 131.68 (d); 129.00 (s); 128.82, 128.12 (2 d); 127.85 (s); 125.23, 120.01, 119.66 (3 d); 119.53 (s); 115.67, 113.92, 113.27, 109.44 (4 d); 104.22 (d, C(1)$_{Gal}$); 75.68, 73.22, 70.36, 68.11 (4 d, C(2-5)$_{Gal}$); 60.38 (t, C(6)$_{Gal}$); 55.90 (q, OCH₃); 28.03 (q, CH₃—C=O).

1-(2-Benzoylphenyl)-1H-indol-3-yl-beta-D-galactopyranoside (I19a)

Yield: 1.09 g (46%); TLC [toluene/ethanol (5:3)]: $R_f$ 0.41.
¹H-NMR [DMSO-d₆]: 7.82-7.81 (m, 1H); 7.80-7.79 (m, 1H); 7.78-7.77 (m, 2H); 7.70-7.69 (m, 1H); 7.68-7.67 (m, 3H); 7.64-7.13 (m, 4H); 7.03 (s, 1H); 6.99-6.95 (m, 1H); 5.23-5.22 (br. d, 1H); 4.85-4.83 (br. d, 1H); 4.68-4.65 (br. s, 1H); 4.51-4.50 (br. d, 1H); 4.29-4.27 (d, J=7.7 Hz, 1H); 3.72-3.70 (m, 1H); 3.63-3.52 (m, 3H); 3.42-3.32 (m, 2H).
¹³C-NMR [DMSO-d₆]: 195.54, 138.83, 136.97, 135.68, 135.48, 133.41, 132.92, 132.21, 129.92, 128.30, 128.14, 127.86, 127.48, 127.18, 125.24, 122.63, 120.61, 119.38, 117.80, 115.27, 109.87, 104.49, 75.40, 73.19, 70.31, 67.91, 60.17.

1-(2-Benzoylphenyl)-4-chloro-1H-indol-3-yl-beta-D-galactopyranoside (I20a)

Yield: 0.87 g (34%); TLC [toluene/ethanol (5:3)]: $R_f$ 0.52.
¹H-NMR [DMSO-d₆]: 7.82-7.78 (m, 1H); 7.70-7.60 (m, 3H); 7.45-7.41 (m, 3H); 7.26-7.22 (m, 2H); 7.10 (s, 1H); 7.05-6.94 (m, 3H); 4.89-4.87 (d, 1H); 4.83-4.81 (d, 1H); 4.66-4.64 (br. s, 1H); 4.53-4.52 (d, J=4.7 Hz, 1H); 4.43-4.41 (br. s, 1H); 3.72-3.70 (m, 1H); 3.61-3.51 (m, 3H); 3.48-3.41 (m, 2H).
¹³C-NMR [DMSO-d₆]: 195.25, 138.20, 136.41, 135.87, 135.58, 134.70, 133.14, 132.23, 129.84, 128.48, 128.02, 127.62, 123.76, 123.15, 120.19, 117.01, 115.40, 108.94, 103.68, 75.36, 73.46, 70.26, 67.91, 60.10.

1-(2-Benzoylphenyl)-6-chloro-1H-indol-3-yl-beta-D-galactopyranoside (I21a)

Yield: 1.30 g (51%); TLC [toluene/ethanol (5:3)]: $R_f$ 0.21.
¹H-NMR [DMSO-d₆]: 7.83-7.79 (m, 1H); 7.71-7.64 (m, 3H); 7.48-7.46 (m, 1H); 7.41-7.37 (m, 3H); 7.26-7.13 (m, 3H); 7.07 (s, 1H); 7.01-6.98 (m, 1H); 5.24-5.23 (br. d, 1H); 4.86-4.84 (br. d, 1H); 4.68-4.65 (br. s, 1H); 4.52-4.50 (br. d, 1H); 4.29-4.27 (d, J=7.5 Hz, 1H); 3.71-3.69 (m, 1H); 3.59-3.53 (m, 3H); 3.44-3.33 (m, 2H).
¹³C-NMR [DMSO-d₆]: 195.45, 138.60, 136.32, 135.66, 135.63, 133.66, 133.04, 132.35, 129.93, 128.82, 128.41, 128.12, 127.96, 127.49, 127.34, 125.23, 119.78, 119.35, 119.28, 116.30, 109.69, 104.49, 75.46, 73.13, 70.26, 67.91, 60.18.

1-(2-Benzoylphenyl)-6-chloro-1H-indol-3-yl-alpha-D-glucopyranoside (I21e)

Yield: 1.57 g (61%); TLC [toluene/ethanol (5:3)]: $R_f$ 0.28.

$^1$H-NMR [DMSO-$d_6$]: 7.83-7.79 (m, 1H); 7.72-7.62 (m, 3H); 7.46-7.44 (m, 1H); 7.39 (s, 1H); 7.38-7.35 (m, 2H); 7.21-7.17 (m, 3H); 7.12 (m, 1H); 7.00-6.98 (m, 1H); 5.08-5.06 (d, 1H); 5.00-4.99 (d, 1H); 4.96-4.95 (d, 1H); 4.91-4.90 (d, J=2.2 Hz, 1H); 4.59-4.57 (m, 1H); 3.68-3.58 (m, 2H); 3.54-3.31 (m, 3H); 3.21-3.15 (m, 1H).

$^{13}$C-NMR [DMSO-$d_6$]: 195.53, 137.91, 136.42, 135.63, 135.45, 133.59, 133.00, 132.45, 130.06, 128.34, 127.97, 127.88, 127.56, 127.32, 119.70, 119.36, 119.20, 115.82, 109.70, 100.63, 73.53, 73.00, 71.70, 70.01, 60.83.

1-(2-Benzoylphenyl)-6-chloro-1H-indol-3-yl-beta-D-glucuronide sodium salt (I21f)

Yield: 1.79 g (69%); TLC [toluene/ethanol (5:3)]: $R_f$ 0.07.

$^1$H-NMR [DMSO-$d_6$]: 7.82-7.79 (m, 1H); 7.69-7.63 (m, 3H); 7.57-7.54 (m, 1H); 7.40-7.38 (m, 3H); 7.24-7.20 (m, 2H); 7.11 (m, 2H); 6.99-6.97 (m, 1H); 6.66 (br. s, 1H); 5.45 (br. s, 1H); 5.21 (br. s, 1H); 4.30 (br. s, 1H); 3.47-3.40 (m, 1H); 3.27-3.22 (m, 3H).

$^{13}$C-NMR [DMSO-$d_6$]: 195.39, 172.84, 138.69, 136.30, 135.61, 133.73, 133.09, 132.41, 129.94, 128.43, 128.02, 127.45, 127.40, 119.79, 119.62, 119.38, 118.31, 116.62, 116.57, 109.64, 103.96, 76.43, 73.93, 73.04, 71.92.

1-(2-Benzoylphenyl)-6-chloro-1H-indol-3-yl-N-acetyl-beta-D-galactosaminide (I21g)

Yield: 1.46 g (53%); TLC [toluene/ethanol (5:3)]: $R_f$ 0.28.

$^1$H-NMR [DMSO-$d_6$]: 7.82-7.74 (m, 2H); 7.70-7.64 (m, 2H); 7.62 (d, NH); 7.43-7.35 (m, 3H); 7.24-7.17 (m, 3H); 7.09 (d, 1H); 7.02 (s, 1H); 6.98 (dd, 1H); 4.73 (d, 1H); 4.63 (t, 1H); 4.60 (d, 1H); 4.42 (d, 1H); 3.93 (q, 1H); 3.70 (t, 1H); 3.60-3.48 (m, 3H); 3.40-3.32 (m, 1H); 1.83 (s, 3H).

$^{13}$C-NMR [DMSO-$d_6$]: 195.5, 169.6, 162.3, 138.7, 136.34, 135.72, 133.70, 133.15, 132.45, 129.95, 128.5, 128.0, 127.55, 127.5, 120.0, 119.3, 118.8, 116.2, 109.8, 103.0, 75.55, 70.8, 67.3, 60.25, 52.0, 23.2.

1-(2-Benzoylphenyl)-5-bromo-4-chloro-1H-indol-3-yl-beta-D-galactopyranoside (I22a)

Yield: 1.14 g (39%); TLC [toluene/ethanol (5:3)]: $R_f$ 0.48.

$^1$H-NMR [DMSO-$d_6$]: 7.83-7.79 (m, 1H); 7.71-7.61 (m, 3H); 7.46-7.42 (m, 3H); 7.34-7.32 (m, 1H); 7.28-7.24 (m, 2H); 7.16 (s, 1H); 7.00-6.98 (m, 1H); 4.96-4.95 (br. d, 1H); 4.84-4.82 (br. d, 1H); 4.66-4.65 (br. s, 1H); 4.53-4.52 (d, J=4.7 Hz, 1H); 4.38-4.35 (br. s, 1H); 3.72-3.70 (m, 1H); 3.61-3.54 (m, 3H); 3.48-3.43 (m, 2H).

$^{13}$C-NMR [DMSO-$d_6$]: 195.12, 137.81, 135.92, 135.55, 133.32, 133.23, 132.30, 129.88, 128.51, 128.35, 128.08, 127.69, 126.55, 123.38, 118.34, 116.70, 112.84, 110.64, 103.89, 75.41, 73.37, 70.18, 67.90, 60.10, 55.98.

1-(2-Benzoyl-5-chlorophenyl)-6-chloro-1H-indol-3-yl-beta-D-galactopyranoside (I23a)

Yield: 1.28 g (47%); TLC [toluene/ethanol (5:3)]: $R_f$ 0.49.

$^1$H-NMR [DMSO-$d_6$]: 7.79 (s, 1H); 7.72 (m, 2H); 7.45-7.39 (m, 4H); 7.22-7.17 (m, 3H); 7.12 (s, 1H); 7.02-6.99 (m, 1H); 5.23-5.22 (d, 1H); 4.85-4.84 (d, 1H); 4.68-4.65 (m, 1H); 4.51-4.50 (d, 1H); 4.29 (br. s, 1H); 3.71-3.69 (m, 1H); 3.57-3.52 (m, 3H); 3.44-3.33 (m, 2H).

$^{13}$C-NMR [DMSO-$d_6$]: 194.51, 138.89, 137.74, 136.51, 135.38, 134.28, 133.64, 133.15, 131.65, 128.41, 128.05, 127.93, 127.66, 127.32, 120.05, 119.49, 119.24, 116.06, 109.84, 104.36, 75.49, 73.12, 70.23, 67.90, 60.19.

1-(2-Benzoyl-5-methoxyphenyl)-6-chloro-1H-indol-3-yl-beta-D-galactopyranoside (I24a)

Yield: 2.4 g (76%); TLC [toluene/ethanol (4:1)]: $R_f$ 0.23.

FT-IR: 3367m, 2911w, 2853w, 1654s, 1600s, 1579m, 1499m, 1470m, 1448m, 1365m, 1264s, 1239s, 1118s, 1075s, 1022s, 975m, 923m, 872s, 750m, 703s.

$^1$H-NMR [DMSO-$d_6$]: 7.66 (d, J=8.6, 1 arom. H); 7.44 (d, J=8.5, 1 arom. H); 6.36-7.32 (m, 1 arom. H); 7.34 (s, 1 arom. H); 7.32 (s, 1 arom. H); 7.21-7.14 (m, 6 arom. H); 6.98 (dd, J=8.5, 1.8, 1 arom. H); 5.23 (d, J=4.9, OH); 4.85 (d, J=5.7, OH); 4.69 (t, J=5.5, OH); 4.51 (d, J=4.7, OH); 4.29 (br. s, H—C(1)$_{Gal}$); 3.92 (s, OCH$_3$); 3.71 (t, J=4.0, H—C(4)$_{Gal}$); 3.60-3.53 (m, 3H—C$_{Gal}$); 3.46 (t, J=6.2, 1H—C$_{Gal}$); 3.39-3.34 (m, 1H—C$_{Gal}$).

$^{13}$C-NMR [DMSO-$d_6$]: 194.80 (s, C=O); 162.32 (s, C—OCH$_3$); 138.58, 138.49, 136.35, 133.58 (4 s); 132.46, 132.14, 128.16, 127.67 (4 d); 127.48, 127.44 (2 s); 119.73 (d); 119.46 (s); 119.21, 116.35, 113.68, 112.35, 109.75 (5 d); 104.42 (d, C(1)$_{Gal}$); 75.56, 73.17, 70.28, 68.00 (4 d, C(2-5)$_{Gal}$); 60.32 (t, C(6)$_{Gal}$); 55.87 (q, OCH$_3$).

1-[2-(2,4-Dimethoxybenzoyl)phenyl]-1H-indol-3-yl-beta-D-galactopyranoside (I25a)

Yield: 1.28 g (48%); TLC [toluene/ethanol (5:3)]: $R_f$ 0.45.

$^1$H-NMR [DMSO-$d_6$]: 7.70-7.65 (m, 1H); 7.55-7.47 (m, 4H); 7.09-6.95 (m, 5H); 6.26-6.23 (m, 2H); 5.25-5.23 (d, 1H); 4.86-4.84 (d, 1H); 4.69-4.66 (br. s, 1H); 4.51-4.50 (d, 1H); 4.33-4.31 (d, J=7.7 Hz, 1H); 3.69 (s, 3H); 3.61-3.54 (m, 4H); 3.44 (s, 3H); 3.48-3.41 (m, 1H); 3.39-3.34 (m, 1H).

$^{13}$C-NMR [DMSO-$d_6$]: 193.05, 163.77, 159.66, 138.91, 138.70, 136.42, 133.78, 131.89, 131.33, 128.95, 127.21, 126.78, 122.30, 120.45, 119.50, 119.02, 117.73, 115.10, 109.65, 105.23, 104.75, 97.55, 75.50, 73.18, 70.35, 68.01, 60.32, 55.41, 55.38.

1-[2-(2,4-Dimethoxybenzoyl)phenyl]-1H-indol-3-yl choline phosphate (I25d)

Yield: 0.92 g (68%); TLC [ethyl acetate/pyridine/acetic acid/water (30:25:5:15)]: $R_f$ 0.46.

$^1$H-NMR [DMSO-$d_6$]: 7.68-7.62 (m, 1H); 7.48 (m, 2H); 7.43 (2 d, 2H); 7.20 (d, 1H); 7.10 (s, 1H); 7.05 (t, 1H); 7.02 (t, 1H); 6.94 (t, 1H); 6.35 (d, 1H); 6.32 (dd, 1H); 4.05 (m, 2H); 3.72 (s, 3H); 3.53 (s, 3H); 3.46 (t, $^3$J[H,P]=4.6 Hz, 2H); 3.03 (s, 9H).

$^{13}$C-NMR [DMSO-$d_6$]: 193.0, 164.1, 160.0, 157.0, 138.8, 136.7, 134.0 (d, J[C,P]=7.4 Hz), 133.6, 132.3, 131.3, 129.0, 127.0 (J[C,P]=2.4 Hz), 122.0, 121.6 (J[C,P]=6.3 Hz), 119.5, 118.9, 117.6, 116.1, 109.7, 105.7, 97.9, 65.4 (J[C,P]=4.8 Hz), 59.0 (J[C,P]=5.36 Hz), 55.5 (2 OCH$_3$), 53.0.

4-Chloro-1-[2-(2,4-dimethoxybenzoyl)phenyl]-1H-indol-3-yl-beta-D-galactopyranoside (I26a)

Yield: 1.76 g (62%); TLC [toluene/ethanol (5:3)]: $R_f$ 0.54.

$^1$H-NMR [DMSO-$d_6$]: 7.70-7.66 (m, 1H); 7.58-7.53 (m, 2H); 7.49-7.47 (m, 1H); 7.12-7.10 (m, 1H); 7.02 (s, 1H); 7.01-6.99 (m, 1H); 6.96-6.93 (m, 2H); 6.34-6.29 (m, 2H); 4.85-4.83 (br. s, 2H); 4.67-4.64 (br. s, 1H); 4.53-4.52 (d, 1H); 4.48-4.46 (d, J=5.9 Hz, 1H); 3.73 (s, 3H); 3.72-3.70 (m, 1H); 3.64-3.55 (m, 3H); 3.48 (s, 3H); 3.46-3.38 (m, 2H).

$^{13}$C-NMR [DMSO-$d_6$]: 192.84, 163.99, 159.72, 139.25, 138.17, 135.77, 135.07, 131.92, 131.33, 128.91, 127.18, 123.74, 122.88, 119.84, 119.36, 116.86, 115.14, 108.77, 105.40, 103.94, 97.59, 75.50, 73.44, 70.32, 68.00, 60.24, 55.48, 55.40.

6-Chloro-1-[2-(2,4-dimethoxybenzoyl)phenyl]-1H-indol-3-yl-beta-D-galactopyranoside (I27a)

Yield: 1.88 g (66%); TLC [toluene/ethanol (5:3)]: $R_f$ 0.45.

$^1$H-NMR [DMSO-$d_6$]: 7.72-7.67 (m, 1H); 7.57-7.56 (m, 2H); 7.52-7.50 (m, 2H); 7.12-7.10 (m, 1H); 7.02 (s, 1H); 7.00-6.98 (m, 2H); 6.31-6.26 (m, 2H); 5.27-5.26 (d, 1H); 4.87-4.86 (d, 1H); 4.69-4.66 (br. s, 1H); 4.52-4.51 (d, J=4.6 Hz, 1H); 4.38-4.35 (br. s, 1H); 3.71 (s, 3H); 3.70-3.68 (m, 1H); 3.60-3.55 (m, 3H); 3.48 (s, 3H); 3.48-3.43 (m, 2H).

13C-NMR [DMSO-d6]: 192.89, 163.89, 159.54, 138.89, 138.52, 135.69, 133.98, 131.92, 131.54, 129.06, 127.77, 127.21, 127.03, 119.36, 119.21, 119.18, 116.09, 109.42, 105.38, 104.68, 97.41, 75.59, 73.13, 70.30, 68.03, 60.36, 55.44, 55.32.

5-Bromo-4-chloro-1-[2-(2,4-dimethoxybenzoyl)phenyl]-1H-indol-3-yl-beta-D-galactopyranoside (I28a)

Yield: 2.17 g (67%); TLC [toluene/ethanol (5:3)]: $R_f$ 0.58.

$^1$H-NMR [DMSO-$d_6$]: 7.72-7.67 (m, 1H); 7.61-7.49 (m, 3H); 7.34-7.31 (m, 1H); 7.12-7.10 (m, 1H); 7.06 (s, 1H); 6.88-6.86 (m, 1H); 6.34-6.31 (m, 1H); 6.28-6.27 (m, 1H); 4.95-4.94 (d, 1H); 4.85-4.84 (d, 1H); 4.67-4.64 (br. s, 1H); 4.53-4.52 (d, J=4.6 Hz, 1H); 4.45 (br. s, 1H); 3.73 (s, 3H); 3.72-3.70 (m, 1H); 3.64-3.51 (m, 3H); 3.47 (s, 3H); 3.46-3.37 (m, 2H).

$^{13}$C-NMR [DMSO-$d_6$]: 192.76, 163.98, 159.63, 139.30, 137.84, 135.27, 133.68, 131.82, 131.42, 128.97, 128.14, 127.24, 126.32, 123.33, 119.28, 118.17, 116.38, 112.51, 110.45, 105.40, 104.06, 97.48, 75.53, 73.36, 70.24, 67.99, 60.24, 55.48, 55.39.

1-[2-(5-Carboxylfuranoyl)phenyl]-6-chloro-1H-indol-3-yl-beta-D-galactopyranoside (I29a)

Yield: 0.99 g (36%); TLC [toluene/ethanol (5:3)]: $R_f$ 0.

$^1$H-NMR [CD$_3$COOD]: 7.82-7.74 (m, 2H); 7.69-7.67 (m, 1H); 7.63-7.59 (m, 1H); 7.55-7.49 (m, 1H); 7.33-7.32 (m, 1H); 7.12 (s, 1H); 7.04-7.02 (m, 1H); 6.97-6.96 (d, 1H); 6.88-6.87 (d, 1H); 4.69-4.67 (d, J=7.2 Hz, 1H); 4.14-4.13 (d, 1H); 4.04-3.94 (m, 3H); 3.86-3.82 (m, 2H).

$^{13}$C-NMR [CD$_3$COOD]: 184.9, 154.0, 147.7, 139.6, 138.2, 135.2, 135.1, 133.6, 130.9, 129.8, 128.4, 127.8, 121.3, 120.6, 119.8, 119.5, 119.1, 116.6, 110.9, 104.3, 75.5, 73.9, 71.9, 69.8, 62.1.

6-Chloro-1-(2-furanoylphenyl)-1H-indol-3-yl-beta-D-galactopyranoside (I30a)

Yield: 1.65 g (66%); TLC [toluene/ethanol (5:3)]: $R_f$ 0.38.

$^1$H-NMR [DMSO-$d_6$]: 7.84 (m, 1H), 7.80-7.76 (m, 1H); 7.72-7.70 (m, 1H); 7.64-7.57 (m, 3H); 7.18 (s, 1H); 7.10-7.03 (m, 3H); 6.54-6.53 (m, 1H); 5.28-5.27 (d, 1H); 4.87-4.85 (d, 1H); 4.66-4.63 (m, 1H); 4.52-4.51 (d, 1H); 4.47-4.45 (d, J=7.7 Hz, 1H); 3.71-3.69 (m, 1H); 3.63-3.53 (m, 3H); 3.48-3.41 (m, 2H).

$^{13}$C-NMR [DMSO-$d_6$]: 181.55, 151.01, 148.81, 138.58, 136.06, 135.24, 133.78, 132.32, 129.62, 127.83, 127.62, 127.56, 120.83, 119.85, 119.48, 119.42, 116.24, 112.61, 109.64, 104.50, 75.54, 73.16, 70.32, 68.00, 60.27.

6-Chloro-1-[2-(N-methylpyrrole-2-carbonyl)phenyl]-1H-indol-3-yl-beta-D-galactopyranoside (I31a)

Yield: 1.76 g (69%); TLC [toluene/ethanol (5:3)]: $R_f$ 0.36.

$^1$H-NMR [DMSO-$d_6$]: 7.95 (m, 1H); 7.73-7.69 (m, 1H); 7.63-7.55 (m, 3H); 7.17 (m, 1H); 7.10 (s, 1H); 7.05-7.02 (m, 2H); 6.35-6.34 (m, 1H); 5.91-5.90 (m, 1H); 5.27-5.26 (d, 1H); 4.86-4.84 (d, 1H); 4.63-4.60 (br. s, 1H); 4.51-4.50 (d, 1H); 4.45-4.43 (d, J=7.7 Hz, 1H); 3.71-3.68 (m, 1H); 3.61-3.33 (m, 5H); 2.88 (s, 3H).

$^{13}$C-NMR [DMSO-$d_6$]: 183.78, 162.23, 138.49, 137.27, 135.67, 133.72, 132.73, 131.16, 129.86, 129.41, 127.44, 127.34, 127.18, 121.99, 119.62, 119.34, 116.07, 109.87, 108.05, 104.62, 75.42, 73.14, 70.29, 67.86, 60.08, 36.40.

Example 2

Preparation of I19c and I25c by N-arylation of I1c (Table Ia)

5.0 mMol aryliodide, 1.31 g (7.48 mMol) I1c and 0.67 g (5.47 mMol) copper(I) acetate in 25 ml dry dimethylacetamide were heated to 150° C. for two hours under a nitrogen atmosphere. The product mixture was cooled to room temperature and diluted with 25 ml ethyl acetate. The suspension was poured onto 50 ml saturated aqueous ammoniumchloride solution and stirred for 30 minutes. The organic phase was washed with brine, dried with sodium sulfate, filtered and evaporated to dryness. The resulting oil was purified by column chromatography on silica gel [toluene; toluene/acetone (10:1)].

1-(2-Benzoylphenyl)-1H-indol-3-yl acetate (I19c)

Yield: 590 mg (33%); TLC (toluene): $R_f$ 0.15.

$^1$H-NMR [DMSO-$d_6$]: 7.83-7.79 (m, 1H); 7.71-7.64 (m, 3H); 7.42-7.36 (m, 3H); 7.32-7.30 (m, 1H); 7.26-7.25 (m, 1H); 7.23-7.11 (m, 4H); 7.05-7.01 (m, 1H); 2.27 (s, 3H).

$^{13}$C-NMR [DMSO-$d_6$]: 195.27, 168.03, 136.36, 135.78, 135.63, 133.41, 133.08, 132.23, 130.69, 129.91, 128.49, 128.11, 127.94, 127.61, 122.89, 120.24, 120.04, 118.37, 117.35, 110.27, 20.46.

1-[2-(2,4-Dimethoxybenzoyl)phenyl]-1H-indol-3-yl acetate (I25c)

Yield: 1.23 g (59%); TLC [toluene/acetone (10:1)]: $R_f$ 0.66.

$^1$H-NMR [DMSO-$d_6$]: 7.71-7.67 (m, 1H); 7.56-7.52 (m, 3H); 7.37-7.35 (m, 1H); 7.31 (s, 1H); 7.18-7.16 (m, 1H); 7.14-7.10 (m, 3H); 7.06-7.02 (m, 1H); 6.30 (s, 1H); 3.70 (s, 3H); 3.49 (s, 3H); 2.30 (s, 3H).

$^{13}$C-NMR [DMSO-d$_6$]: 192.77, 167.99, 163.99, 139.07, 135.72, 133.60, 131.92, 131.31, 130.42, 128.92, 128.79, 128.09, 127.65, 127.13, 125.21, 122.64, 119.75, 118.24, 117.16, 110.09, 105.52, 97.58, 55.38, 55.33, 20.51.

Example 3

Preparation of I32 by N-arylation of I6 (Table Ia)

1-(2-Benzoylphenyl)-1H-indol-3-yl ethyl carbamate (I32)

1.30 g (4.22 mMol) 2-iodobenzophenone, 1.29 g (6.32 mMol) 3-aminoindol-3-ethylcarbamate and 0.57 g (4.65 mMol) copper(I) acetate in 25 ml dry dimethylacetamide were heated to 150° C. for two hours under a nitrogen atmosphere. The product mixture was cooled to room temperature and diluted with 25 ml ethyl acetate. The suspension was poured onto 50 ml saturated aqueous ammoniumchloride solution and stirred for 30 minutes. The organic phase was washed with brine, dried with sodium sulfate, filtered and evaporated to dryness. The resulting oil was purified by column chromatography on silica gel [toluene; toluene/acetone (10:1)].

Yield: 100 mg (6%); TLC [toluene]: R$_f$ 0.10.

$^1$H-NMR [DMSO-d$_6$]: 9.50 (s, NH); 7.81-7.77 (m, 1H); 7.71-7.60 (m, 4H); 7.41-7.36 (m, 4H); 7.20-7.16 (m, 3H); 7.11-7.07 (m, 1H); 6.99-6.95 (m, 1H); 4.13 (q, 2H); 1.24 (t, 3H).

$^{13}$C-NMR [DMSO-d$_6$]: 195.42, 153.57, 136.98, 135.73, 135.43, 133.92, 132.95, 132.15, 129.89, 128.42, 127.86, 127.43, 127.13, 122.59, 121.06, 119.21, 118.44, 117.53, 117.08, 109.78, 60.15, 14.53.

Example 4

Preparation of bis[1-(2-acetylphenyl)-1H-indol-3-yl]-disulfane (I33, Table Ia)

1-(2-Acetylphenyl)-1H-indol-3-yl-isothiuronium iodide 1.80 g (7.65 mMol) 1-(2-acetylphenyl)-1H-indole (prepared by the method of Example 1) and 1.17 g thiourea (15.4 mMol) were dissolved in a mixture of 35 ml methanol (35 ml) and 4 ml water. 3.90 g iodine (15.4 mMol) was dissolved in a solution of potassium iodide (3.82 g, 23 mMol) in water (7.7 ml). This iodine solution was added dropwise to the solution above at ambient temperature during an hour and warmed to 35° C. for three hours. Solvents were removed by evaporation. The residual oil was dissolved in ethyl acetate (40 ml). The solution was extracted three times with water (3×10 ml). The organic layer was dried and treated with charcoal (1 g). The crude product was obtained after evaporation of the filtrate and purified by column chromatography on silica gel (100 g, ethyl acetate).

Yield: 1.27 g (38%).

$^1$H-NMR [DMSO-d$_6$]: 9.06 (s, NH$_2$); 8.62 (s, NH$_2$); 8.18 (s, 1H); 7.98 (d, 1H); 7.84 (t, 1H); 7.70 (2 t, 2×1H); 7.61 (m, 1H); 7.30 (m, 2H); 7.12 (m, 1H); 2.18 (s, 3H).

$^{13}$C-NMR [DMSO-d$_6$]: 199.4, 170.2, 139.3, 137.8, 136.2, 135.0, 133.1, 129.9, 129.3, 129.0, 128.5, 123.9, 122.0, 118.2, 111.0, 92.6, 29.0

Bis[1-(2-acetylphenyl)-1H-indol-3-yl]-disulfane (I33)

1-(2-Acetylphenyl)-1H-indol-3-yl-isothiuronium iodide (0.47 g, 1.07 mMol) was dissolved in a mixture of degassed dioxane (2.7 ml) and degassed water (1.57 ml) under a nitrogen atmosphere.

A degassed 5% aqueous solution of sodium hydroxide (0.8 ml, 1.22 mMol) was added dropwise at ambient temperature, whereby the solution turned dark-brown. The solution was stirred for 48 hours at 45° C. The product mixture was evaporated, dissolved in water (5 ml) and extracted with ethyl acetate. The organic layers were dried over sodium sulfate and evaporated leaving the crude product as viscous oil which was purified by silica gel flash chromatography.

Yield: 70 mg (24%).

$^1$H-NMR [DMSO-d$_6$]: 7.84 (dd, 1H); 7.66 (dt, 1H); 7.62 (dt, 1H); 7.60 (d, 1H); 7.55 (s, 1H); 7.38 (d, 1H); 7.19 (2 t, 2×1H); 7.03 (d, 1H); 1.94 (s, 3H).

$^{13}$C-NMR [DMSO-d$_6$]: 199.1, 137.5, 136.4, 135.3, 132.8, 129.6, 128.8, 128.7, 128.5, 123.5, 121.3, 119.3, 110.4, 108.0, 28.4.

Example 5

Preparation of 10H-indolo[1,2-a]indoles (Table Ic)

Enzymatic reactions were performed in 100 mM Na$_2$PO$_4$ buffer, pH 7.3 containing 1 mM MgCl$_2$ and 670 mg/l enzyme substrate. E. coli beta-galactosidase or K. lactis lactase were added to a final concentration of 1000 U/l or 1500 U/l, respectively. 30 ml reaction volumes were incubated for 5-18 hours at 37° C. with gentle shaking. The reaction product was collected by centrifugation (4400 g, 15 min), pellets were washed with 10 ml H$_2$O and centrifuged again (4400 g, 15 min).

11-Hydroxy-10H-indolo[1,2-a]indol-10-one (IO10)

$^1$H-NMR [DMSO-d$_6$]: 7.73 (d, J=8.2 Hz, 2 arom. H); 7.69 (d, J=7.7 Hz, 2 arom. H); 7.50 (t, J=7.3 Hz, 2 arom. H); 7.07 (t, J=7.5 Hz, 2 arom. H); 5.79 (br. s).

$^{13}$C-NMR [DMSO-d$_6$]: 160.75 (s, C=O); 138.32 (s, arom. C); 132.10 (d, arom. C—H); 127.15 (s, arom. C); 123.27, 121.52 (2 d, arom. C—H); 118.65 (s, C(10a); 111.72 (d, arom. C—H).

Note: IO10 turns to be readily water-soluble above a pH of 5.

10H-Indolo[1,2-a]indol-10-one (IO13)

$^1$H-NMR [DMSO-d$_6$]: 7.94 (m, 1H); 7.84 (m, 1H); 7.74 (m, 1H); 7.67 (m, 1H); 7.62 (m, 1H); 7.48 (m, 1H); 7.35 (m, 1H); 7.18 (m, 1H); 7.17 (m, 1H).

$^{13}$C-NMR [DMSO-d$_6$]: 180.7, 144.8, 136.3, 135.0, 133.7, 132.0, 128.5, 128.4, 124.9, 124.7, 124.3, 122.2, 112.2, 112.0, 108.1.

MS (CI): 220.2 ([M+H]$^+$).

11-Methyl-10H-indolo[1,2-a]indol-10-one (IO14)

$^1$H-NMR [DMSO-d$_6$]: 7.85 (m, 1H); 7.77 (m, 1H); 7.71 (m, 1H); 7.62 (m, 1H); 7.59 (m, 1H); 7.47 (m, 1H); 7.16 (m, 1H); 7.13 (m, 1H); 2.50 (s, 3H).

$^{13}$C-NMR [DMSO-d$_6$]: 180.8, 144.0, 135.8, 133.3, 132.6, 131.7, 128.6, 128.5, 124.1, 123.4, 122.8, 121.5, 121.3, 111.7, 111.6, 8.8.

UV: $\lambda_{max}$=255, 355, 435 nm.

9-Chloro-11-methyl-10H-indolo[1,2-a]indol-10-one (IO15)

$^1$H-NMR [DMSO-d$_6$]: 7.88-7.86 (m, 1H); 7.76-7.72 (m, 2H); 7.60-7.56 (m, 1H); 7.51-7.47 (m, 1H); 7.21-7.17 (m, 1H); 7.12-7.10 (m, 1H); 2.49 (s, 3H).
$^{13}$C-NMR [DMSO-d$_6$]: 178.3, 145.6, 136.8, 133.2, 133.0, 132.3, 130.8, 128.8, 124.8, 124.3, 123.0, 122.2, 121.9, 112.0, 110.8, 8.9.
UV: $\lambda_{max}$=245, 365, 440 nm.

7-Chloro-11-methyl-10H-indolo[1,2-a]indol-10-one (IO16)

$^1$H-NMR [DMSO-d$_6$]: 8.00-7.98 (m, 1H); 7.92 (m, 1H); 7.73-7.71 (m, 1H); 7.58-7.56 (m, 1H); 7.50-7.46 (m, 1H); 7.20-7.15 (m, 2H); 2.48 (s, 3H).
$^{13}$C-NMR [DMSO-d$_6$]: 179.9, 144.8, 140.4, 133.4, 132.9, 132.1, 128.9, 127.7, 125.6, 123.5, 123.0, 122.6, 122.0, 112.24, 112.21, 9.00.
UV: $\lambda_{max}$=245, 360, 430 nm.

8-Bromo-9-chloro-11-methyl-10H-indolo[1,2-a]indol-10-one (IO17)

$^1$H-NMR [DMSO-d$_6$]: 7.96-7.94 (m, 1H); 7.90-7.87 (m, 1H); 7.76-7.72 (m, 2H); 7.53-7.48 (m, 1H); 7.22-7.18 (m, 1H); 2.50 (s, 3H).
$^{13}$C-NMR [DMSO-d$_6$]: 177.3, 144.6, 139.5, 133.2, 132.9, 131.9, 130.7, 129.2, 126.0, 123.2, 123.1, 122.2, 116.9, 112.2, 112.1, 9.0.
UV: $\lambda_{max}$=245, 365, 450 nm.

7-Chloro-3-methoxy-11-methyl-10H-indolo[1,2-a]indol-10-one (IO18)

$^1$H-NMR [DMSO-d$_6$]: 8.07 (d, J=1.6, 1 H); 7.61 (d, J=8.8, 1 H); 7.56 (d, J=8.0, 1H); 7.39 (d, J=2.1, 1 H); 7.17 (dd, J=8.0, 1.6, 1 H); 6.80 (dd, J=8.8, 2.2, 1 H); 3.94 (s, OCH$_3$); 2.46 (s, CH$_3$).

11-Phenyl-10H-indolo[1,2-a]indol-10-one (IO19)

$^1$H-NMR [DMSO-d$_6$]: 8.04-8.02 (m, 1H); 7.99-7.92 (m, 4H); 7.71-7.65 (m, 2H); 7.59-7.55 (m, 3H); 7.51-7.47 (m, 1H); 7.29-7.19 (m, 2H).
$^{13}$C-NMR [DMSO-d$_6$]: 180.1, 144.0, 136.0, 133.9, 130.7, 130.2, 128.9, 128.8, 124.6, 124.5, 124.3, 123.7, 122.7, 112.4, 112.3.
UV: $\lambda_{max}$=245, 370, 460 nm.

9-Chloro-11-phenyl-10H-indolo[1,2-a]indol-10-one (IO20)

$^1$H-NMR [DMSO-d$_6$]: 8.05-8.03 (m, 1H); 7.97-7.90 (m, 4H); 7.67-7.63 (m, 1H); 7.59-7.55 (m, 3H); 7.51-7.49 (m, 1H); 7.31-7.27 (m, 1H); 7.20-7.18 (m, 1H).
$^{13}$C-NMR [DMSO-d$_6$]: 145.5, 137.0, 133.7, 131.0, 130.5, 129.0, 128.8, 125.4, 124.9, 124.4, 123.8, 123.1, 112.6, 111.1.

8-Bromo-9-chloro-11-phenyl-10H-indolo[1,2-a]indol-10-one (IO22)

$^1$H-NMR [DMSO-d$_6$]: 8.04-8.00 (m, 2H); 7.98-7.92 (m, 3H); 7.89-7.86 (m, 1H); 7.60-7.48 (m, 4H); 7.31-7.28 (m, 1H).
$^{13}$C-NMR [DMSO-d$_6$]: 144.3, 139.5, 133.7, 131.0, 130.4, 130.2, 129.0, 128.9, 128.7, 126.2, 125.4, 123.9, 123.1, 117.5, 112.6, 112.5.

7-Chloro-3-methoxy-11-phenyl-10H-indolo[1,2-a]indol-10-one (IO24)

$^1$H-NMR [DMSO-d$_6$]: 8.13 (d, J=1.6, 1 H); 7.94, 7.92 (2 br. s, 2H); 7.77 (d, J=9.0, 1 H); 7.59 (d, J=8.0, 1 H); 7.54 (br. t, J=8.0, 2 H); 7.48-7.44 (m, 2H); 7.21 (dd, J=8.0, 1.6, 1 H); 6.87 (dd, J=9.0, 2.2, 1 H); 3.37 (s, OCH$_3$).

11-(5-Carboxyfuran-2-yl)-7-chloro-10H-indolo[1,2-a]indol-10-one (IO29)

$^1$H-NMR [DMSO-d$_6$]: 8.57-8.54 (m, 1H); 8.08-8.06 (m, 1H); 8.00 (m, 1H); 7.84 (m, 1H); 7.71-7.69 (m, 1H); 7.61-7.57 (m, 1H); 7.36-7.33 (m, 1H); 7.26-7.24 (m, 1H); 6.85-6.84 (m, 1H).

7-Chloro-11-(furan-2-yl)-10H-indolo[1,2-a]indol-10-one (IO30)

$^1$H-NMR [DMSO-d$_6$]: 8.33-8.30 (m, 1H); 8.16-8.14 (m, 1H); 8.09 (m, 1H); 8.03 (m, 1H); 7.86-7.83 (m, 1H); 7.70-7.68 (m, 1H); 7.60-7.56 (m, 1H); 7.34-7.31 (m, 1H); 7.27-7.25 (m, 1H); 6.82-6.81 (m, 1H).
$^{13}$C-NMR [DMSO-d$_6$]: 177.7, 148.0, 145.0, 144.2, 140.2, 133.9, 129.4, 128.3, 127.4, 125.8, 125.2, 124.0, 123.1, 114.0, 113.2, 112.7, 112.6, 112.4.

Conclusion: IO stains are produced efficiently from corresponding indicators subjected to enzymatic external stimuli (eS).

Example 6

Optical Absorption of 10H-indolo[1,2-a]indoles (FIG. 1)

Dried 10H-Indolo[1,2-a]indole pellets obtained from procedures of example 5 were dissolved in ethanol/DMF (1:1) at 2.5 mM. This stock solution was diluted to 0.22 mM in 100% EtOH and a spectral scan was recorded on a Spectramax M5 (Molecular Devices). The spectra of the corresponding indicators were recorded for comparison. Data are shown in FIG. 1.

Absorption spectra of Indicators and corresponding IO stains are substantially different in the visible band.

Conclusion: IO staining produces strong and readily detectable signals.

Example 7

In-vitro Indication of Fluoride and Hydroxide Ions with Indicator Systems I4b/MDAB and I4c/MDAB I4b (0.4 g, 1.11 mMol) and MDAB (0.25 g, 1.39 mMol) were dissolved in ethanol (8 ml). The resulting indicator solution was kept under an atmosphere of nitrogen gas. A 1 mM solution of tetrabutylammonium fluoride in THF (1.6 ml) was added to the indicator solution at room temperature. After 10 minutes BI4 precipitated as intensely violet heavy solid which was collected and dried (0.19 g, 42%). Similarly, BI4 was obtained by exposing I4c/MDAB to aqueous base.
$^1$H-NMR [DMSO-d$_6$]: 9.84 (s, H1); 7.68 (d, J=8.6 Hz, H6); 7.61 (d, J=8.8 Hz, H6'); 7.07 (s, =CH—); 7.02 (d, J=8.6 Hz, H7); 6.38 (dd, J=8.8 Hz, H5'); 6.24 (d, H3'); 3.88 (s, OCH$_3$); 3.02 (s, N(CH$_3$)$_2$).

$^{13}$C-NMR [DMSO-d$_6$]: 181.0 (C=O), 160.0, 152.8, 152.5, 138.3, 130.74, 130.71, 129.9, 118.3, 113.0, 111.4, 110.0, 109.1, 104.9, 94.6 (OCH$_3$), 55.5 (N(CH$_3$)$_2$).

Note: There are two possible stereoisomers of BI4, (E)-5-bromo-4-chloro-2-(4-dimethylamino-2-methoxybenzylidene)indolin-3-one and (Z)-5-bromo-4-chloro-2-(4-dimethylamino-2-methoxybenzylidene)indolin-3-one. NOE NMR measurements indicate that only (Z)-BI4 was formed in the process.

Conclusion: (1) indicator system I4b/MDAB is potentially useful for the anaerobic detection of fluoride ions and (2) indicator system I4c/MDAB is potentially useful for the irreversible detection of transient alkaline pH conditions (common pH indicators allow reversible detection only).

Example 8

Reaction of MDAB with indol-3-amine (aS6) and indol-3-thiole (aS7)

Exposure of active signalogen aS6 (prepared by reduction of the corresponding nitroso compound) to atmospheric oxygen yielded a polymeric brown precipitate rather than the bis-imino-indigo derivative. In the presence of MDAB and in the absence of oxygen aS6 produced yellow color probably the Schiff base which, however, escaped isolation. Formation of the expected hetero aldol product was not observed.

Exposure of active signalogen aS7 (obtained in analogy to I33) to oxygen yields the corresponding disulfane rather than the bis-thion-indigo analogue. In the presence of MDAB and in the absence of oxygen the expected violet color appeared only under strongly acidic conditions.

Conclusion: MDAB staining may not be suitable for indicators derived of indol-3-amines or indol-3-thiols.

Example 9a

MDAB Staining of Bacterial Colonies with Indicators I4a and I5a (Table III, Entries 1-25)

Tryptic Soy Agar (TSA) with yeast extract (0.6%) was used as the base plating medium. The media were autoclaved at 121° C. for 15 minutes and placed in a 50° C. water bath to cool. Indicators were added to the basal medium at a final concentration of 40 mg/100 ml (from 80 mg/ml stock solutions in DMF). Over night cultures of enteric bacterial cells in Brain Heart Infusion Broth were streaked onto the plates and incubated at 35° C. for 24 hours under aerobic and anaerobic conditions. After incubation, the colonial morphologies on the plates were recorded (Table III).

Under anaerobic conditions and in the absence of MDAB indicators tested failed to stain bacterial colonies producing suitable external stimulus (beta-D-galactosidase). Weak staining was observed occasionally due to residual oxygen (micro-anaerobic conditions). Under aerobic conditions indigo (IN-stains) generally dominated the effects of MDAB staining. For example indicator system I4a/MDAB stained colonies violet under anaerobic but indigo blue under aerobic conditions.

Conclusion: MDAB staining is a potentially valuable method for detection and isolation of microbial species especially under anaerobic conditions.

Note: 4-(N,N-Dimethyl)aminobenzaldehyde (DAB) and a large number of other potentially suitable Adol acceptors selected from the group of aromatic carbonyl compounds did not produce any BI-stains under all conditions tested when used to replace MDAB.

Example 9b

MDAB Staining of Bacterial Colonies with Indicators I9a, I10a, I11a and I12a (Table III, Entries 26-37)

Indicators were tested with live cultures on Nutrient Agar plates. Nutrient Agar (5 g/l peptone, 5 g/l NaCl, 2 g/l yeast extract, 1 g/l beef extract, 13 g/l agar, pH 7.4) was autoclaved and allowed to cool to 50° C. Then substrates were added to final concentrations of 150 mg/l (from a 20 mg/ml stock solution in DMF). Optionally MDAB was added to a concentration of 1 mM (from a 200 mM stock solution in DMF) and plates were poured. Agar plates were inoculated with cultures of *Eschericha coli* (NM1) or *Salmonella enteritidis* (RKI 05/07992) (pre-grown on nutrient broth for 8-18 hours) and aerobically incubated at 37° C. Results were recorded after 48 h of incubation and are shown in Table III.

Conclusion: Indicators I9a, I11a and I12a are potentially useful for MDAB staining under aerobic conditions.

Example 10

10H-Indolo[1,2-a]indole (10) Staining of Bacterial Colonies (Table IVa-c)

Nutrient Agar (5 g/l peptone, 5 g/l NaCl, 2 g/l yeast extract, 1 g/l beef extract, 13 g/l agar, pH 7.4) was autoclaved and allowed to cool to 50° C. Then indicators were added to final concentrations of 150 mg/l (from a 20 mg/ml stock solution in DMF).

Optionally IPTG was added to 100 mg/l (from a 100 mg/ml stock solution in H$_2$O) and plates were poured. Agar plates were inoculated with cultures of beta-galactosidase positive *Eschericha coli* (NM1) or beta-galactosidase negative *Salmonella enteritidis* (RKI 05/07992) (pre-grown on nutrient broth for 8-18 hours) and incubated at 37° C. Plates were inspected at 16, 20, 24 and 48 hours and pictures were recorded at 18, 24, and 48 hours with a Digistore 2 Image documentation system (CAMAG) under white light. Data are shown in Tables IVa, IVb and IVc.

A considerable number of indicators molecules (Table IVa, IVb) and a selection of labile groups (Table IVc) were tested with various microbial species producing different biomarker enzymes (external stimuli, eS). The color of stains ranges from yellow to red. Some stains tested show excellent localization of external stimuli (enzyme activity) while others were significantly soluble in the medium and may be of use for solution based assay (Table IVa). Staining is accompanied by fluorescence while green fluorescence was observed to be of transient nature, (caused by fluorescence of the active Signalogen) 10H-indolo[1,2-a]indoles fluorescence at longer wavelength (yellow-red) was stable.

Conclusion: IO staining is a potentially valuable method for detection and isolation of microbial species providing a new color scheme, long wave fluorescence and complete independence of auxiliary reagents (aR) potentially interfering with the assay.

Example 11

Indigo (IN) and 10H-indolo[1,2-a]indole (10) Concurrent Staining (Table IVd)

Nutrient Agar containing 150 mg/l 1-(2-benzoylphenyl)-6-chloro-1H-indol-3-yl-beta-D-galactopyranoside (I21a), 100 mg/l IPTG and 75 mg/l 5-bromo-4-chloro-1H-indol-3- yl-beta-D-glucopyranoside (I4h) was inoculated with *Escherichia coli, Klebsiella pneumoniae, Enterococcus faecalis* and *Enterobacter aerogenes*. Data collected after 24 h of incubation at 37° C. are given in Table IVd. Microbial colonies producing both beta-D-galactosidase and beta-D-glucosidase appeared green due to parallel formation of blue IN and the yellow IO stains.

Conclusion: The combination of complementary IN and IO staining is potentially useful to extend the currently available color scheme.

Example 12

IN and IO Staining of Bacterial Colonies under Anaerobic Conditions (Table IVe)

Nutrient Agar plates containing 150 mg/l of various substrates and 100 mg/l IPTG were inoculated with *Escherichia coli*. Plates were put in an anaerobic jar (Anaerojar, Oxoid), an AnaeroGen sachet (Oxoid) was added, the jar was closed and incubated for 24 hours at 37° C. Data were recorded and are shown in Table IVe.

IN staining cannot be used under anaerobic conditions. While due to slower colonial growth diffusion of some IO stains increases under anaerobic conditions other stains such as IO22 produced from indicator I22a provide perfect localization.

Conclusion: IO staining is a potentially valuable technique for use under micro-aerobic or anaerobic conditions.

Example 13

IO Staining of Bacterial Colonies on Blood Agar Plates (Table IVf)

Standard commercially available Blood Agar plates were impregnated with 150 mg/l 1-(2-benzoylphenyl)-6-chloro-1H-indol-3-yl-beta-D-galactopyranoside (I21a) and 100 mg/l IPTG. The plate was inoculated with *Klebsiella pneumoniae*. Results after incubation at 37° C. for 24 hours are given in Table IVf.

IO stain contrasts very well with the agar plate. Further, despite the quenching effect of blood IO fluorescence is fully maintained and readily detectable.

Conclusion: IO staining is potentially valuable for use in microbial blood culture.

Example 14

IO Staining of Fungal Colonies (Table IVg)

Agar base (6 g/l soytone, 1.5 g/l yeast extract, 1 g/l glucose, 10 mM sodium phosphate buffer, 13 g/l agar, pH 7.0) was autoclaved and allowed to cool to 50° C. Then 1 mM $MnSO_4$, 1 g/l N-Acetyl-D-galactosamine and: 1-(2-benzoylphenyl)-6-chloro-1H-indol-3-yl-N-acetyl-beta-D-galactosaminide (I21g) were added to final concentrations of 0.64 mM (from a 50 mM stock solution in DMF) and plates poured. Plates were inoculated with *Candida albicans, Candida krusei* and *Saccharomyces cerevisiae* and incubated at 37° C. for 48 hours. Results were recorded and are shown in Table IVg.

Example 15

Fluorescence of 10H-indolo[1,2-a]indoles Stained Microbial Cells (FIG. 2)

Plating media from Example 10 were examined under 366 nm UV irradiation at 16, 20, 24 and 48 hours for fluorescence by means of Digistore 2 Image documentation system (CA-MAG). Data are shown in Tables IVa, IVb and IVc. Loops of bacterial cells, grown for 48 hours on Nutrient Agar plates containing 150 mg/l beta-D-galactosidase indicator and 100 mg/l IPTG, were directly streaked into wells of black clear bottom microtiter plates. Fluorescence scans were recorded on a Spectramax M5 (Molecular Devices). Data are shown in FIG. 2. Stained cells were shown to be detectable under a standard fluorescence microscope.

IO staining is accompanied by significant fluorescence. While green fluorescence observed appeared to be of transient nature, (caused by fluorescence of the active 1H-indol-3-yl signalogen) IO fluorescence at longer wavelengths (yellow-red) was found to be persistent.

Conclusion: IO staining represents a potentially valuable method for detection and isolation of microbial species providing a means of long wave fluorescence staining of live microbial colonies and a novel simple tool for fluorescence labeling of individual cells.

Example 16

Indication of Carbamate Hydrolysis

When 1-(2-benzoylphenyl)-1H-indol-3-yl ethyl carbamate (I32) was subjected to short treatment with 1N aqueous NaOH solution or prolonged exposure to pig liver esterase a yellow precipitate was produced which was identified as 11-phenyl-10H-indolo[1,2-a]indol-10-one (IO19) by TLC comparison with reference samples.

Apparently, 11-phenyl-10H-indolo[1,2-a]indol-10-imine (IO32), which is expected to yield from the aldol condensation is rapidly hydrolyzed to IO19.

Conclusion: The concept of IO staining can be expanded to include indicators producing 1-(2-benzoylphenyl)-1H-indol-3-amine (aS32) or similar active signalogens hence providing the potential design for long sought precipitating indicators for amino-peptidase enzymes.

Example 17

Indication of Disulfide Reduction

Bis[1-(2-acetylphenyl)-1H-indol-3-yl]-disulfane (I33, 2 mg) was dissolved in methanol (0.5 ml). Tris(2-carboxyethyl) phosphine hydrochloride (TCEP, 20 mg) was added to the almost colorless solution. Upon subsequent addition of 1 N aqueous sodium hydroxide solution the solution turned yellow.

Conclusion: (1) IO staining/indication is potentially useful for detection reducing environments and (2) the concept of IO staining can potentially be expanded to include indicators producing 1-(2-acetylphenyl)-1H-indol-3-thiol (aS33) or similar active signalogens.

TABLE Ia

List of 1H-Indol-3-yl Indicators

| | | | | | Chemical Structure of Indicator ($R_4$ = H) | | | | | | | | | | |
|---|---|---|---|---|---|---|---|---|---|---|---|---|---|---|---|
| Entry | Code | Indicator | LG | aS | $R_1$ | $R_2$ | $R_3$ | $R_5$ | X | $R_6$ | $R_7$ | $R_8$ | $R_9$ | $R_{10}$ |
| 1 | I1a | 1H-Indol-3-yl-beta-D-galactopyranoside | a | 1 | H | H | H | H | O | — | — | — | — | — |
| 2 | I1c | 1H-Indol-3-yl acetate | c | 1 | H | H | H | H | O | — | — | — | — | — |
| 3 | I2a | 4-Chloro-1H-indol-3-yl-beta-D-galactopyranoside | a | 2 | Cl | H | H | H | O | — | — | — | — | — |
| 4 | I3a | 6-Chloro-1H-indol-3-yl-beta-D-galactopyranoside | a | 3 | H | H | Cl | H | O | — | — | — | — | — |
| 5 | I3e | 6-Chloro-1H-indol-3-yl-alpha-D-glucopyranoside | e | 3 | H | H | Cl | H | O | — | — | — | — | — |
| 6 | I3f | 6-Chloro-1H-indol-3-yl-beta-D-glucuronide sodium salt | f | 3 | H | H | Cl | H | O | — | — | — | — | — |
| 7 | I3g | 6-Chloro-1H-indol-3-yl-N-acetyl-beta-D-galactosaminide | g | 3 | H | H | Cl | H | O | — | — | — | — | — |
| 8 | I4a | 5-Bromo-4-chloro-1H-indol-3-yl-beta-D-galactopyranoside | a | 4 | Cl | Br | H | H | O | — | — | — | — | — |
| 9 | I4b | 5-Bromo-3-(tert-butyldimethylsilyloxy)-4-chloro-1H-indole | b | 4 | Cl | Br | H | H | O | — | — | — | — | — |
| 10 | I4c | 5-Bromo-4-chloro-1H-indol-3-yl acetate | c | 4 | Cl | Br | H | H | O | — | — | — | — | — |
| 11 | I4d | 5-Bromo-4-chloro-1H-indol-3-yl choline phosphate | d | 4 | Cl | Br | H | H | O | — | — | — | — | — |
| 12 | I4h | 5-Bromo-4-chloro-1H-indol-3-yl-beta-D-glucopyranoside | h | 4 | Cl | Br | H | H | O | — | — | — | — | — |
| 13 | I5a | 5-Bromo-6-chloro-1H-indol-3-yl-beta-D-galactopyranoside | a | 5 | H | Br | Cl | H | O | — | — | — | — | — |
| 14 | I6- | 1H-Indol-3-yl-ethyl carbamate | 1) | 6 | H | H | H | H | N | — | — | — | — | — |
| 15 | I8a | 1-Phenyl-1H-indol-3-yl-beta-D-galactopyranoside | a | 8 | H | H | H | $R_{11}$ | O | H | H | H | H | H |
| 16 | I9a | 6-Chloro-1-phenyl-1H-indol-3-yl-beta-D-galactopyranoside | a | 9 | H | H | Cl | $R_{11}$ | O | H | H | H | H | H |
| 17 | I10a | 1-[2-(Methoxy-carbonyl)phenyl]-1H-indol-3-yl-beta-D-galactopyranoside | a | 10 | H | H | H | $R_{12}$ | O | H | H | H | H | OMe |
| 18 | I11a | 6-Chloro-1-[2-(methoxy-carbonyl)phenyl]-1H-indol-3-yl-beta-D-galactopyranoside | a | 11 | H | H | Cl | $R_{12}$ | O | H | H | H | H | OMe |
| 19 | I12a | 5-Bromo-4-chloro-1-[2-(methoxycarbonyl)phenyl]-1H-indol-3-yl-beta-D-galactopyranoside | a | 12 | Cl | Br | H | $R_{12}$ | O | H | H | H | H | OMe |
| 20 | I13a | 1-(2-Formylphenyl)-1H-indol-3-yl-beta-D-galactopyranoside | a | 13 | H | H | H | $R_{12}$ | O | H | H | H | H | H |
| 21 | I14a | 1-(2-Acetylphenyl)-1H-indol-3-yl-beta-D-galactopyranoside | a | 14 | H | H | H | $R_{12}$ | O | H | H | H | H | Me |
| 22 | I15a | 1-(2-Acetylphenyl)-4-chloro-1H-indol-3-yl-beta-D-galactopyranoside | a | 15 | Cl | H | H | $R_{12}$ | O | H | H | H | H | Me |
| 23 | I16a | 1-(2-Acetylphenyl)-6-chloro-1H-indol-3-yl-beta-D-galactopyranoside | a | 16 | H | H | Cl | $R_{12}$ | O | H | H | H | H | Me |
| 24 | I17a | 1-(2-Acetylphenyl)-5-bromo-4-chloro-1H-indol-3-yl-beta-D-galactopyranoside | a | 17 | Cl | Br | H | $R_{12}$ | O | H | H | H | H | Me |
| 25 | I18a | 1-(2-Acetyl-5-methoxy-phenyl)-6-chloro-1H-indol-3-yl-beta-D-galactopyranoside | a | 18 | H | H | Cl | $R_{12}$ | O | H | OMe | H | H | Me |
| 26 | I19a | 1-(2-Benzoylphenyl)-1H-indol-3-yl-beta-D-galactopyranoside | a | 19 | H | H | H | $R_{12}$ | O | H | H | H | H | Phe |
| 27 | I19c | 1-(2-Benzoylphenyl)-1H-indol-3-yl acetate | c | 19 | H | H | H | $R_{12}$ | O | H | H | H | H | Phe |
| 28 | I20a | 1-(2-Benzoylphenyl)-4-chloro-1H-indol-3-yl-beta-D-galactopyranoside | a | 20 | Cl | H | H | $R_{12}$ | O | H | H | H | H | Phe |
| 29 | I21a | 1-(2-Benzoylphenyl)-6-chloro-1H-indol-3-yl-beta-D-galactopyranoside | a | 21 | H | H | Cl | $R_{12}$ | O | H | H | H | H | Phe |

TABLE Ia-continued

List of 1H-Indol-3-yl Indicators

| | | | | | | Chemical Structure of Indicator ($R_4$ = H) | | | | | | | | | |
|---|---|---|---|---|---|---|---|---|---|---|---|---|---|---|---|
| Entry | Code | Indicator | LG | aS | $R_1$ | $R_2$ | $R_3$ | $R_5$ | X | $R_6$ | $R_7$ | $R_8$ | $R_9$ | $R_{10}$ |
| 30 | I21e | 1-(2-Benzoylphenyl)-6-chloro-1H-indol-3-yl-alpha-D-glucopyranoside | e | 21 | H | H | Cl | $R_{12}$ | O | H | H | H | H | Phe |
| 31 | I21f | 1-(2-Benzoylphenyl)-6-chloro-1H-indol-3-yl-beta-D-glucuronide sodium salt | f | 21 | H | H | Cl | $R_{12}$ | O | H | H | H | H | Phe |
| 32 | I21g | 1-(2-Benzoylphenyl)-6-chloro-1H-indol-3-yl-N-acetyl-beta-D-galactosaminide | g | 21 | H | H | Cl | $R_{12}$ | O | H | H | H | H | Phe |
| 33 | I22a | 1-(2-Benzoylphenyl)-5-bromo-4-chloro-1H-indol-3-yl-beta-D-galactopyranoside | a | 22 | Cl | Br | H | $R_{12}$ | O | H | H | H | H | Phe |
| 34 | I23a | 1-(2-Benzoyl-5-chlorphenyl)-6-chloro-1H-indol-3-yl-beta-D-galactopyranoside | a | 23 | H | H | Cl | $R_{12}$ | O | H | Cl | H | H | Phe |
| 35 | I24a | 1-(2-Benzoyl-5-methoxy-phenyl)-6-chloro-1H-indol-3-yl-beta-D-galactopyranoside | a | 24 | H | H | Cl | $R_{12}$ | O | H | OMe | H | H | Phe |
| 36 | I25a | 1-[2-(2,4-Dimethoxy-benzoyl)phenyl]-1H-indol-3-yl-beta-D-galactopyranoside | a | 25 | H | H | H | $R_{12}$ | O | H | H | H | H | DMP |
| 37 | I25c | 1-[2-(2,4-Dimethoxy-benzoyl)phenyl]-1H-indol-3-yl acetate | c | 25 | H | H | H | $R_{12}$ | O | H | H | H | H | DMP |
| 38 | I25d | 1-[2-(2,4-Dimethoxy-benzoyl)phenyl]-1H-indol-3-yl choline phosphate | d | 25 | H | H | H | $R_{12}$ | O | H | H | H | H | DMP |
| 39 | I26a | 1-[2-(2,4-Dimethoxy-benzoyl)phenyl]-4-chloro-1H-indol-3-yl-beta-D-galactopyranoside | a | 26 | Cl | H | H | $R_{12}$ | O | H | H | H | H | DMP |
| 40 | I27a | 6-Chloro 1-[2-(2,4-dimethoxy-benzoyl)phenyl]-1H-indol-3-yl-beta-D-galactopyranoside | a | 27 | H | H | Cl | $R_{12}$ | O | H | H | H | H | DMP |
| 41 | I28a | 5-Bromo-4-chloro-1-[2-(2,4-dimethoxybenzoyl)phenyl]-1H-indol-3-yl-beta-D-galactopyranoside | a | 28 | Cl | Br | H | $R_{12}$ | O | H | H | H | H | DMP |
| 42 | I29a | 1-[2-(5-Carboxylfuranoyl)-phenyl]-6-chloro-1H-indol-3-yl-beta-D-galactopyranoside | a | 29 | H | H | Cl | $R_{12}$ | O | H | H | H | H | CFur |
| 43 | I30a | 6-Chloro-1-(2-furanoyl-phenyl)-1H-indol-3-yl-beta-D-galactopyranoside | a | 30 | H | H | Cl | $R_{12}$ | O | H | H | H | H | Fur |
| 44 | I31a | 6-Chloro-1-[2-(N-methyl-pyrrole-2-carbonyl)phenyl]-1H-indol-3-yl-beta-D-galactopyranoside | a | 31 | H | H | Cl | $R_{12}$ | O | H | H | H | H | NPyr |
| 45 | I32- | 1-(2-Benzoylphenyl)-1H-indol-3-yl ethyl carbamate | 1) | 32 | H | H | H | $R_{12}$ | N | H | H | H | H | Phe |
| 46 | I33- | Bis[1-(2-acetylphenyl)-1H-indol-3-yl]-disulfane | 2) | 33 | H | H | H | $R_{12}$ | S | H | H | H | H | Me |

1) LG: —N=C=O-Ethyl (ethylcarbamate)
2) LG: —S—S— (disulfane) or isothiuronium iodide

TABLE Ib

List of 1H-Indol-3-yl Active Signalogens

| | | | Chemical Structure of Active Signalogen | | | | | | | | | | |
|---|---|---|---|---|---|---|---|---|---|---|---|---|---|
| Entry | Code | Active Signalogen | $R_1$ | $R_2$ | $R_3$ | $R_4$ | $R_5$ | X | $R_6$ | $R_7$ | $R_8$ | $R_9$ | $R_{10}$ |
| 1 | aS1 | 1H-Indol-3-ol | H | H | H | H | H | O | — | — | — | — | — |
| 2 | aS2 | 4-Chloro-1H-indol-3-ol | Cl | H | H | H | H | O | — | — | — | — | — |
| 3 | aS3 | 6-Chloro-1H-indol-3-ol | H | H | Cl | H | H | O | — | — | — | — | — |
| 4 | aS4 | 5-Bromo-4-chloro-1H-indol-3-ol | Cl | Br | H | H | H | O | — | — | — | — | — |
| 5 | aS5 | 5-Bromo-6-chloro-1H-indol-3-ol | H | Br | Cl | H | H | O | — | — | — | — | — |
| 6 | aS6 | 1H-Indol-3-amine | H | H | H | H | H | N | — | — | — | — | — |

TABLE Ib-continued

List of 1H-Indol-3-yl Active Signalogens

| | | | Chemical Structure of Active Signalogen | | | | | | | | | | |
|---|---|---|---|---|---|---|---|---|---|---|---|---|---|
| Entry | Code | Active Signalogen | $R_1$ | $R_2$ | $R_3$ | $R_4$ | $R_5$ | X | $R_6$ | $R_7$ | $R_8$ | $R_9$ | $R_{10}$ |
| 7 | aS7 | 1H-Indol-3-thiol | H | H | H | H | H | S | — | — | — | — | — |
| 8 | aS8 | 1-Phenyl-1H-indol-3-ol | H | H | H | H | $R_{11}$ | O | H | H | H | H | H |
| 9 | aS9 | 6-Chloro-1-phenyl-1H-indol-3-ol | H | H | Cl | H | $R_{11}$ | O | H | H | H | H | H |
| 10 | aS10 | 1-[2-(Methoxy-carbonyl)phenyl]-1H-indol-3-ol | H | H | H | H | $R_{12}$ | O | H | H | H | H | OMe |
| 11 | aS11 | 1-[2-(Methoxy-carbonyl)phenyl]-6-chloro-1H-indol-3-ol | H | H | Cl | H | $R_{12}$ | O | H | H | H | H | OMe |
| 12 | aS12 | 5-Bromo-4-chloro-1-[2-(methoxycarbonyl)phenyl)-1H-indol-3-ol | Cl | Br | H | H | $R_{12}$ | O | H | H | H | H | OMe |
| 13 | aS13 | 1-(2-Formylphenyl)-1H-indol-3-ol | H | H | H | H | $R_{12}$ | O | H | H | H | H | H |
| 14 | aS14 | 1-(2-Acetylphenyl)-1H-indol-3-ol | H | H | H | H | $R_{12}$ | O | H | H | H | H | Me |
| 15 | aS15 | 1-(2-Acetylphenyl)-4-chloro-1H-indol-3-ol | Cl | H | H | H | $R_{12}$ | O | H | H | H | H | Me |
| 16 | aS16 | 1-(2-Acetylphenyl)-6-chloro-1H-indol-3-ol | H | H | Cl | H | $R_{12}$ | O | H | H | H | H | Me |
| 17 | aS17 | 1-(2-Acetylphenyl)-5-bromo-4-chloro-1H-indol-3-ol | Cl | Br | H | H | $R_{12}$ | O | H | H | H | H | Me |
| 18 | aS18 | 1-(2-Acetyl-5-methoxyphenyl)-6-chloro-1H-indol-3-ol | H | H | Cl | H | $R_{12}$ | O | H | OMe | H | H | Me |
| 19 | aS19 | 1-(2-Benzoylphenyl)-1H-indol-3-ol | H | H | H | H | $R_{12}$ | O | H | H | H | H | Phe |
| 20 | aS20 | 1-(2-Benzoylphenyl)-4-chloro-1H-indol-3-ol | Cl | H | H | H | $R_{12}$ | O | H | H | H | H | Phe |
| 21 | aS21 | 1-(2-Benzoylphenyl)-6-chloro-1H-indol-3-ol | H | H | Cl | H | $R_{12}$ | O | H | H | H | H | Phe |
| 22 | aS22 | 1-(2-Benzoylphenyl)-5-bromo-4-chloro-1H-indol-3-ol | Cl | Br | H | H | $R_{12}$ | O | H | H | H | H | Phe |
| 23 | aS23 | 1-(2-Benzoyl-5-chlorphenyl)-6-chloro-1H-indol-3-ol | H | H | Cl | H | $R_{12}$ | O | H | Cl | H | H | Phe |
| 24 | aS24 | 1-(2-Benzoyl-5-methoxy-phenyl)-6-chloro-1H-indol-3-ol | H | H | Cl | H | $R_{12}$ | O | H | OMe | H | H | Phe |
| 25 | aS25 | 1-[2-(2,4-Dimethoxy-benzoyl)phenyl]-1H-indol-3-ol | H | H | H | H | $R_{12}$ | O | H | H | H | H | DMP |
| 26 | aS26 | 4-Chloro-1-[2-(2,4-dimethoxy-benzoyl)phenyl]-1H-indol-3-ol | Cl | H | H | H | $R_{12}$ | O | H | H | H | H | DMP |
| 27 | aS27 | 6-Chloro-1-[2-(2,4-dimethoxy-benzoyl)phenyl]-1H-indol-3-ol | H | H | Cl | H | $R_{12}$ | O | H | H | H | H | DMP |
| 28 | aS28 | 5-Bromo-4-chloro-1-[2-(2,4-dimethoxybenzoyl)phenyl]-1H-indol-3-ol | Cl | Br | H | H | $R_{12}$ | O | H | H | H | H | DMP |
| 29 | aS29 | 6-Chloro-1-[2-(5-carboxyl-furanoyl)phenyl]-1H-indol-3-ol | H | H | Cl | H | $R_{12}$ | O | H | H | H | H | CFur |
| 30 | aS30 | 6-Chloro-1-(2-furanoylphenyl)-1H-indol-3-ol | H | H | Cl | H | $R_{12}$ | O | H | H | H | H | Fur |
| 31 | aS31 | 6-Chloro-1-[2-(N-methyl-pyrrole-2-carbonyl)phenyl]-1H-indol-3-ol | H | H | Cl | H | $R_{12}$ | O | H | H | H | H | NPyr |
| 32 | aS32 | 1-(2-Benzoylphenyl)-1H-indol-3-amine | H | H | H | H | $R_{12}$ | N | H | H | H | H | Phe |
| 33 | aS33 | 1-(2-Acetylphenyl)-1H-indol-3-thiol | H | H | H | H | $R_{12}$ | S | H | H | H | H | Me |

TABLE Ic

List of Signalophores produced by 1H-indol-3-yl Indicator Systems

| | | | | | | Chemical Structure of Signalophore ($R_{13} = R_{10}$, OH) | | | | | | | | | | |
|---|---|---|---|---|---|---|---|---|---|---|---|---|---|---|---|---|
| Entry | Code | Type | Signalophore | aS | aR | $R_1$ | $R_2$ | $R_3$ | $R_4$ | $R_5$ | X | $R_6$ | $R_7$ | $R_8$ | $R_9$ | $R_{13}$ |
| 1 | IN1 | IN | Indigo | 1 | Air | H | H | H | H | H | O | — | — | — | — | — |
| 2 | IN2 | IN | 4,4'-Dichloroindigo | 2 | Air | Cl | H | H | H | H | O | — | — | — | — | — |
| 3 | IN3 | IN | 6,6'-Dichloroindigo | 3 | Air | H | H | Cl | H | H | O | — | — | — | — | — |
| 4 | IN4 | IN | 5,5'-Dibromo-4,4'-dichloroindigo | 4 | Air | Cl | Br | H | H | H | O | — | — | — | — | — |

TABLE Ic-continued

List of Signalophores produced by 1H-indol-3-yl Indicator Systems

Chemical Structure of Signalophore ($R_{13} = R_{10}$, OH)

| Entry | Code | Type | Signalophore | aS | aR | $R_1$ | $R_2$ | $R_3$ | $R_4$ | $R_5$ | X | $R_6$ | $R_7$ | $R_8$ | $R_9$ | $R_{13}$ |
|---|---|---|---|---|---|---|---|---|---|---|---|---|---|---|---|---|
| 5 | IN5 | IN | 5,5'-Dibromo-6,6'-dichloroindigo | 5 | Air | H | Br | Cl | H | H | O | — | — | — | — | — |
| 6 | IN8 | IN | 1,1'-Diphenylindigo | 8 | Air | H | H | H | H | $R_{11}$ | O | H | H | H | H | H |
| 7 | IN9 | IN | 6,6'-Dichloro-1,1-diphenylindigo | 9 | Air | H | H | Cl | H | $R_{11}$ | O | H | H | H | H | H |
| 8 | IN10 | IN | 1,1'-Di[2-(methoxycarbonyl)phenyl]indigo | 10 | Air | H | H | H | H | $R_{12}$ | O | H | H | H | H | OMe |
| 9 | IN11 | IN | 1,1'-Di[2-(methoxycarbonyl)phenyl]-6,6'-dichloroindigo | 11 | Air | H | H | Cl | H | $R_{12}$ | O | H | H | H | H | OMe |
| 10 | IN12 | IN | 1,1'-Di[2-(methoxycarbonyl)phenyl]-5,5'-dibromo-4,4'-dichloroindigo | 12 | Air | Cl | Br | H | H | $R_{12}$ | O | H | H | H | H | OMe |
| 11 | BI1 | BI | 2-(4-Dimethylamino-2-methoxybenzylidene)indolin-3-one | 1 | MDAB | H | H | H | H | H | O | — | — | — | — | — |
| 12 | BI2 | BI | 4-Chloro-2-(4-dimethylamino-2-methoxybenzylidene)indolin-3-one | 2 | MDAB | Cl | H | H | H | H | O | — | — | — | — | — |
| 13 | BI3 | BI | 6-Chloro-2-(4-dimethylamino-2-methoxybenzylidene)indolin-3-one | 3 | MDAB | H | H | Cl | H | H | O | — | — | — | — | — |
| 14 | BI4 | BI | 5-Bromo-4-chloro-2-(4-dimethylamino-2-methoxybenzylidene)indolin-3-one | 4 | MDAB | Cl | Br | H | H | H | O | — | — | — | — | — |
| 15 | BI5 | BI | 5-Bromo-6-chloro-2-(4-dimethylamino-2-methoxybenzylidene)indolin-3-one | 5 | MDAB | H | Br | Cl | H | H | O | — | — | — | — | — |
| 16 | BI8 | BI | 2-(4-Dimethylamino-2-methoxybenzylidene)-1-phenylindolin-3-one | 8 | MDAB | H | H | H | H | $R_{11}$ | O | H | H | H | H | H |
| 17 | BI9 | BI | 6-Chloro-2-(4-dimethylamino-2-methoxybenzylidene)-1-phenylindolin-3-one | 9 | MDAB | H | H | Cl | H | $R_{11}$ | O | H | H | H | H | H |
| 18 | BI10 | BI | 2-(4-Dimethylamino-2-methoxybenzylidene)-1-(2-(methoxycarbonyl)phenyl)indolin-3-one | 10 | MDAB | H | H | H | H | $R_{12}$ | O | H | H | H | H | OMe |
| 19 | BI11 | BI | 6-Chloro-2-(4-dimethylamino-2-methoxybenzylidene)-1-[2-(methoxycarbonyl)-phenyl]indolin-3-one | 11 | MDAB | H | H | Cl | H | $R_{12}$ | O | H | H | H | H | OMe |
| 20 | BI12 | BI | 5-Bromo-4-chloro-2-(4-dimethylamino-2-methoxybenzylidene)-1-[2-(methoxycarbonyl)-phenyl]indolin-3-one | 12 | MDAB | Cl | Br | H | H | $R_{12}$ | O | H | H | H | H | OMe |
| 21 | BI6 | BI | 2-(4-Dimethylamino-2-methoxybenzylidene)indolin-3-imine | 6 | MDAB | H | H | H | H | H | N | — | — | — | — | — |
| 22 | BI7 | BI | 2-(4-Dimethylamino-2-methoxybenzylidene)indolin-3-thione | 7 | MDAB | H | H | H | H | H | S | — | — | — | — | — |
| 23 | IO10 | IO | 11-Hydroxy-10H-indolo[1,2-a]indol-10-one | 10 | — | H | H | H | H | NA | O | H | H | H | H | OH |
| 24 | IO11 | IO | 7-Chloro-11-hydroxy-10H-indolo[1,2-a]indol-10-one | 11 | — | H | H | Cl | H | NA | O | H | H | H | H | OH |
| 25 | IO12 | IO | 8-Bromo-9-chloro-11-hydroxy-10H-indolo[1,2-a]indol-10-one | 12 | — | Cl | Br | H | H | NA | O | H | H | H | H | OH |
| 26 | IO13 | IO | 10H-Indolo[1,2-a]indol-10-one | 13 | — | H | H | H | H | NA | O | H | H | H | H | H |

TABLE Ic-continued

List of Signalophores produced by 1H-indol-3-yl Indicator Systems

Chemical Structure of Signalophore ($R_{13} = R_{10}$, OH)

| Entry | Code | Type | Signalophore | aS | aR | $R_1$ | $R_2$ | $R_3$ | $R_4$ | $R_5$ | X | $R_6$ | $R_7$ | $R_8$ | $R_9$ | $R_{13}$ |
|---|---|---|---|---|---|---|---|---|---|---|---|---|---|---|---|---|
| 27 | IO14 | IO | 11-Methyl-10H-indolo-[1,2-a]indol-10-one | 14 | — | H | H | H | H | NA | O | H | H | H | H | Me |
| 28 | IO15 | IO | 9-Chloro-11-methyl-10H-indolo[1,2-a]indol-10-one | 15 | — | Cl | H | H | H | NA | O | H | H | H | H | Me |
| 29 | IO16 | IO | 7-Chloro-11-methyl-10H-indolo[1,2-a]indol-10-one | 16 | — | H | H | Cl | H | NA | O | H | H | H | H | Me |
| 30 | IO17 | IO | 8-Bromo-9-chloro-11-methyl-10H-indolo[1,2-a]indol-10-one | 17 | — | Cl | Br | H | H | NA | O | H | H | H | H | Me |
| 31 | IO18 | IO | 7-Chloro-11-methyl-3-methoxy-10H-indolo-[1,2-a]indol-10-one | 18 | — | H | H | Cl | H | NA | O | H | OMe | H | H | Me |
| 32 | IO19 | IO | 11-Phenyl-10H-indolo-[1,2-a]indol-10-one | 19 | — | H | H | H | H | NA | O | H | H | H | H | Phe |
| 33 | IO20 | IO | 9-Chloro-11-phenyl-10H-indolo[1,2-a]indol-10-one | 20 | — | Cl | H | H | H | NA | O | H | H | H | H | Phe |
| 34 | IO21 | IO | 7-Chloro-11-phenyl-10H-indolo[1,2-a]indol-10-one | 21 | — | H | H | Cl | H | NA | O | H | H | H | H | Phe |
| 35 | IO22 | IO | 8-Bromo-9-chloro-11-phenyl-10H-indolo[1,2-a]indol-10-one | 22 | — | Cl | Br | H | H | NA | O | H | H | H | H | Phe |
| 36 | IO23 | IO | 3,7-Dichloro-11-phenyl-10H-indolo[1,2-a]indol-10-one | 23 | — | H | H | Cl | H | NA | O | H | Cl | H | H | Phe |
| 37 | IO24 | IO | 7-Chloro-3-methoxy-11-phenyl-10H-indolo-[1,2-a]indol-10-one | 24 | — | H | H | Cl | H | NA | O | H | OMe | H | H | Phe |
| 38 | IO25 | IO | 11-(2,4-Dimethoxy)-phenyl-10H-indolo-[1,2-a]indol-10-one | 25 | — | H | H | H | H | NA | O | H | H | H | H | DMP |
| 39 | IO27 | IO | 7-Chloro-11-(2,4-dimethoxy)phenyl-10H-indolo[1,2-a]indol-10-one | 27 | — | H | H | Cl | H | NA | O | H | H | H | H | DMP |
| 40 | IO26 | IO | 9-Chloro-11-(2,4-dimethoxy)phenyl-10H-indolo[1,2-a]indol-10-one | 26 | — | Cl | H | H | H | NA | O | H | H | H | H | DMP |
| 41 | IO28 | IO | 8-Bromo-9-chloro-11-(2,4-dimethoxy)phenyl-10H-indolo[1,2-a]indol-10-one | 28 | — | Cl | Br | H | H | NA | O | H | H | H | H | DMP |
| 42 | IO29 | IO | 7-Chloro-11-(5-carboxyfuran-2-yl)-10H-indolo[1,2-a]indol-10-one | 29 | — | H | H | Cl | H | NA | O | H | H | H | H | CFur |
| 43 | IO30 | IO | 7-Chloro-11-(furan-2-yl)-10H-indolo[1,2-a]indol-10-one | 30 | — | H | H | Cl | H | NA | O | H | H | H | H | Fur |
| 44 | IO32 | IO | 11-Phenyl-10H-indolo[1,2-a]indol-10-imine | 32 | — | H | H | H | H | NA | N | H | H | H | H | Phe |
| 45 | IO33 | IO | 11-Metyl-10H-indolo-[1,2-a]indol-10-thione | 33 | — | H | H | H | H | NA | S | H | H | H | H | Me |
| 46 | IO31 | IO | 7-Chloro-11-(N-methylpyrrol-2-yl)-10H-indolo[1,2-a]indol-10-one | 31 | — | H | H | Cl | H | NA | O | H | H | H | H | NPyr |

TABLE IIa

List of Aerobic 1H-Indol-3-yl Indicator Systems (no MDAB)

| Entry | Indicator/Active Signalogen | Code | aS | aR | LG | External Stimulus | Signalophore BI | IO | IN |
|---|---|---|---|---|---|---|---|---|---|
| 1 | 1H-Indol-3-yl-beta-D-galactopyranoside | I1a | 1 | Air | a | Enzyme: beta-D-galactosidase | NA | NA | 1 |
| 2 | 1H-Indol-3-yl acetate | I1c | 1 | Air | c | Enzyme: Esterase; Ion: Hydroxide | NA | NA | 1 |
| 3 | 4-Chloro-1H-indol-3-yl-beta-D-galactopyranoside | I2a | 2 | Air | a | Enzyme: beta-D-galactosidase | NA | NA | 2 |
| 4 | 6-Chloro-1H-indol-3-yl-beta-D-galactopyranoside | I3a | 3 | Air | a | Enzyme: beta-D-galactosidase | NA | NA | 3 |
| 5 | 6-Chloro-1H-indol-3-yl-alpha-D-glucopyranoside | I3e | 3 | Air | e | Enzyme: alpha-glucosidase | NA | NA | 3 |
| 6 | 6-Chloro-1H-indol-3-yl-beta-D-glucuronide sodium salt | I3f | 3 | Air | f | Enzyme: beta-D-glucuronidase | NA | NA | 3 |
| 7 | 6-Chloro-1H-indol-3-yl-N-acetyl-beta-D-galactosaminide | I3g | 3 | Air | g | Enzyme: Galactosamidase | NA | NA | 3 |
| 8 | 5-Bromo-4-chloro-1H-indol-3-yl-beta-D-galactopyranoside | I4a | 4 | Air | a | Enzyme: beta-D-galactosidase | NA | NA | 4 |
| 9 | 5-Bromo-3-(tert-butyldimethylsilyloxy)-4-chloro-1H-indole | I4b | 4 | Air | b | Ion: Fluoride | NA | NA | 4 |
| 10 | 5-Bromo-4-chloro-1H-indol-3-yl acetate | I4c | 4 | Air | c | Enzyme: Esterase; Ion: Hydroxide | NA | NA | 4 |
| 11 | 5-Bromo-4-chloro-1H-indol-3-yl choline phosphate | I4d | 4 | Air | d | Enzyme: Phospholipase c | NA | NA | 4 |
| 12 | 5-Bromo-4-chloro-1H-indol-3-yl-beta-D-glucopyranoside | I4h | 4 | Air | h | Enzyme: beta-D-glucosidase | NA | NA | 4 |
| 13 | 5-Bromo-6-chloro-1H-indol-3-yl-beta-D-galactopyranoside | I5a | 5 | Air | a | Enzyme: beta-D-galactosidase | NA | NA | 4 |
| 14 | 1H-Indol-3-yl-ethyl carbamate | I6 | 6 | Air | 1) | Enzyme: Esterase; Ion: Hydroxide | NA | NA | * |
| 15 | (1H-Indol-3-thiol) | NA | 7 | Air | 2) | — | NA | NA | — |
| 16 | 1-Phenyl-1H-indol-3-yl-beta-D-galactopyranoside | I8a | 8 | Air | a | Enzyme: beta-D-galactosidase | NA | NA | 8 |
| 17 | 6-Chloro-1-phenyl-1H-indol-3-yl-beta-D-galactopyranoside | I9a | 9 | Air | a | Enzyme: beta-D-galactosidase | NA | NA | 9 |
| 18 | 1-[2-(Methoxy-carbonyl)phenyl]-1H-indol-3-yl-beta-D-galactopyranoside | I10a | 10 | Air | a | Enzyme: beta-D-galactosidase | NA | 10 | (10) |
| 19 | 6-Chloro-1-[2-(methoxy-carbonyl)phenyl]-1H-indol-3-yl-beta-D-galactopyranoside | I11a | 11 | Air | a | Enzyme: beta-D-galactosidase | NA | 11 | (11) |
| 20 | 5-Bromo-4-chloro-1-[2-(methoxycarbonyl)phenyl]-1H-indol-3-yl-beta-D-galactopyranoside | I12a | 12 | Air | a | Enzyme: beta-D-galactosidase | NA | 12 | (12) |
| 21 | 1-(2-Formylphenyl)-1H-indol-3-yl-beta-D-galactopyranoside | I13a | 13 | Air | a | Enzyme: beta-D-galactosidase | NA | 13 | — |
| 22 | 1-(2-Acetylphenyl)-1H-indol-3-yl-beta-D-galactopyranoside | I14a | 14 | Air | a | Enzyme: beta-D-galactosidase | NA | 14 | — |
| 23 | 1-(2-Acetylphenyl)-4-chloro-1H-indol-3-yl-beta-D-galactopyranoside | I15a | 15 | Air | a | Enzyme: beta-D-galactosidase | NA | 15 | — |
| 24 | 1-(2-Acetylphenyl)-6-chloro-1H-indol-3-yl-beta-D-galactopyranoside | I16a | 16 | Air | a | Enzyme: beta-D-galactosidase | NA | 16 | — |
| 25 | 1-(2-Acetylphenyl)-5-bromo-4-chloro-1H-indol-3-yl-beta-D-galactopyranoside | I17a | 17 | Air | a | Enzyme: beta-D-galactosidase | NA | 17 | — |
| 26 | 1-(2-Acetyl-5-methoxyphenyl)-6-chloro-1H-indol-3-yl-beta-D-galactopyranoside | I18a | 18 | Air | a | Enzyme: beta-D-galactosidase | NA | 18 | — |
| 27 | 1-(2-Benzoylphenyl)-1H-indol-3-yl-beta-D-galactopyranoside | I19a | 19 | Air | a | Enzyme: beta-D-galactosidase | NA | 19 | — |
| 28 | 1-(2-Benzoylphenyl)-1H-indol-3-yl acetate | I19c | 19 | Air | c | Enzyme: Esterase; Ion: Hydroxide | NA | 19 | — |
| 29 | 1-(2-Benzoylphenyl)-4-chloro-1H-indol-3-yl-beta-D-galactopyranoside | I20a | 20 | Air | a | Enzyme: beta-D-galactosidase | NA | 20 | — |

TABLE IIa-continued

List of Aerobic 1H-Indol-3-yl Indicator Systems (no MDAB)

| Entry | Indicator/Active Signalogen | Code | aS | aR | LG | External Stimulus | Signalophore BI | Signalophore IO | Signalophore IN |
|---|---|---|---|---|---|---|---|---|---|
| 30 | 1-(2-Benzoylphenyl)-6-chloro-1H-indol-3-yl-beta-D-galactopyranoside | I21a | 21 | Air | a | Enzyme: beta-D-galactosidase | NA | 21 | — |
| 31 | 1-(2-Benzoylphenyl)-6-chloro-1H-indol-3-yl-alpha-D-glucopyranoside | I21e | 21 | Air | e | Enzyme: alpha-glucosidase | NA | 21 | — |
| 32 | 1-(2-Benzoylphenyl)-6-chloro-1H-indol-3-yl-beta-D-glucuronide sodium salt | I21f | 21 | Air | f | Enzyme: beta-D-glucuronidase | NA | 21 | — |
| 33 | 1-(2-Benzoylphenyl)-6-chloro-1H-indol-3-yl-N-acetyl-beta-D-galactosaminide | I21g | 21 | Air | g | Enzyme: Galactosamidase | NA | 21 | — |
| 34 | 1-(2-Benzoylphenyl)-5-bromo-4-chloro-1H-indol-3-yl-beta-D-galactopyranoside | I22a | 22 | Air | a | Enzyme: beta-D-galactosidase | NA | 22 | — |
| 35 | 1-(2-Benzoyl-5-chlorphenyl)-6-chloro-1H-indol-3-yl-beta-D-galactopyranoside | I23a | 23 | Air | a | Enzyme: beta-D-galactosidase | NA | 23 | — |
| 36 | 1-(2-Benzoyl-5-methoxy-phenyl)-6-chloro-1H-indol-3-yl-beta-D-galactopyranoside | I24a | 24 | Air | a | Enzyme: beta-D-galactosidase | NA | 24 | — |
| 37 | 1-[2-(2,4-Dimethoxy-benzoyl)lphenyl]-1H-indol-3-yl-beta-D-galactopyranoside | I25a | 25 | Air | a | Enzyme: beta-D-galactosidase | NA | 25 | — |
| 38 | 1-[2-(2,4-Dimethoxy-benzoyl)phenyl]-1H-indol-3-yl acetate | I25c | 25 | Air | c | Enzyme: Esterase; Ion: Hydroxide | NA | 25 | — |
| 39 | 1-[2-(2,4-Dimethoxy-benzoyl)phenyl]-1H-indol-3-yl choline phosphate | I25d | 25 | Air | d | Enzyme: Phospholipase c | NA | 25 | — |
| 40 | 6-Chloro-1-[2-(2,4-dimethoxy-benzoyl)phenyl]-1H-indol-3-yl-beta-D-galactopyranoside | I27a | 26 | Air | a | Enzyme: beta-D-galactosidase | NA | 26 | — |
| 41 | 4-Chloro-1-[2-(2,4-dimethoxy-benzoyl)phenyl]-1H-indol-3-yl-beta-D-galactopyranoside | I26a | 27 | Air | a | Enzyme: beta-D-galactosidase | NA | 27 | — |
| 42 | 5-Bromo-4-chloro-1-[2-(2,4-dimethoxybenzoyl)phenyl]-1H-indol-3-yl-beta-D-galactopyranoside | I28a | 28 | Air | a | Enzyme: beta-D-galactosidase | NA | 28 | — |
| 43 | 1-[2-(5-Carboxyl-furanoyl)phenyl]-6-chloro-1H-indol-3-yl-beta-D-galactopyranoside | I29a | 29 | Air | a | Enzyme: beta-D-galactosidase | NA | 29 | — |
| 44 | 6-Chloro-1-(2-furanoyl-phenyl)-1H-indol-3-yl-beta-D-galactopyranoside | I30a | 30 | Air | a | Enzyme: beta-D-galactosidase | NA | 30 | — |
| 45 | 6-Chloro-1-[2-(N-methyl-pyrrole-2-carbonyl)phenyl]-1H-indol-3-yl-beta-D-galactopyranoside | I31a | 31 | Air | a | Enzyme: beta-D-galactosidase | NA | 31 | — |
| 46 | 1-(2-Benzoylphenyl)-1H-indol-3-yl ethyl carbamate | I32 | 32 | Air | 1) | Enzyme: Esterase; Ion: Hydroxide | NA | 32 | — |
| 47 | Bis[1-(2-acetylphenyl)-1H-indol-3-yl]-disulfane | I33 | 33 | Air | 2) | Reducing Agent: TCEP | NA | 33 | — |

NP: Not Performed
NA: Not Applicable
*: dark precipitate
1) LG: —N═C═O-Ethyl (ethylcarbamate)
2) LG: —S—S-(disulfane) or isothiuronium iodide

TABLE IIb

List of Aerobic 1H-Indol-3-yl/MDAB Indicator Systems

| Entry | Indicator/Active Signalogen | Code | aS | aR | LG | External Stimulus | Signalophore BI | Signalophore IO | Signalophore IN |
|---|---|---|---|---|---|---|---|---|---|
| 1 | 1H-Indol-3-yl-beta-D-galactopyranoside | I1a | 1 | Air/MDAB | a | Enzyme: beta-D-galactosidase | (1) | NA | 1 |

TABLE IIb-continued

List of Aerobic 1H-Indol-3-yl/MDAB Indicator Systems

| Entry | Indicator/Active Signalogen | Code | aS | aR | LG | External Stimulus | Signalophore BI | IO | IN |
|---|---|---|---|---|---|---|---|---|---|
| 2 | 1H-Indol-3-yl acetate | I1c | 1 | Air/MDAB | c | Enzyme: Esterase; Ion: Hydroxide | NP | NA | NP |
| 3 | 4-Chloro-1H-indol-3-yl-beta-D-galactopyranoside | I2a | 2 | Air/MDAB | a | Enzyme: beta-D-galactosidase | (2) | NA | 2 |
| 4 | 6-Chloro-1H-indol-3-yl-beta-D-galactopyranoside | I3a | 3 | Air/MDAB | a | Enzyme: beta-D-galactosidase | (3) | NA | 3 |
| 5 | 6-Chloro-1H-indol-3-yl-alpha-D-glucopyranoside | I3e | 3 | Air/MDAB | e | Enzyme: alpha-glucosidase | NP | NA | NP |
| 6 | 6-Chloro-1H-indol-3-yl-beta-D-glucuronide sodium salt | I3f | 3 | Air/MDAB | f | Enzyme: beta-D-glucuronidase | NP | NA | NP |
| 7 | 6-Chloro-1H-indol-3-yl-N-acetyl-beta-D-galactosaminide | I3g | 3 | Air/MDAB | g | Enzyme: Galactosamidase | NP | NA | NP |
| 8 | 5-Bromo-4-chloro-1H-indol-3-yl-beta-D-galactopyranoside | I4a | 4 | Air/MDAB | a | Enzyme: beta-D-galactosidase | (4) | NA | 4 |
| 9 | 5-Bromo-3-(tert-butyldimethylsilyloxy)-4-chloro-1H-indole | I4b | 4 | Air/MDAB | b | Ion: Fluoride | (4) | NA | 4 |
| 10 | 5-Bromo-4-chloro-1H-indol-3-yl acetate | I4c | 4 | Air/MDAB | c | Enzyme: Esterase; Ion: Hydroxide | (4) | NA | 4 |
| 11 | 5-Bromo-4-chloro-1H-indol-3-yl choline phosphate | I4d | 4 | Air/MDAB | d | Enzyme: Phospholipase c | NP | NP | NP |
| 12 | 5-Bromo-4-chloro-1H-indol-3-yl-beta-D-glucopyranoside | I4h | 4 | Air/MDAB | h | Enzyme: beta-D-glucosidase | NP | NP | NP |
| 13 | 5-Bromo-6-chloro-1H-indol-3-yl-beta-D-galactopyranoside | I5a | 5 | Air/MDAB | a | Enzyme: beta-D-galactosidase | (4) | NA | 4 |
| 14 | 1H-Indol-3-yl-ethyl carbamate | I6 | 6 | Air/MDAB | 1) | Enzyme: Esterase; Ion: Hydroxide | * | NA | — |
| 15 | (1H-Indol-3-thiol) | NA | 7 | Air/MDAB | 2) | Ion: Hydroxyde | (6) | NA | — |
| 16 | 1-Phenyl-1H-indol-3-yl-beta-D-galactopyranoside | I8a | 8 | Air/MDAB | a | Enzyme: beta-D-galactosidase | NP | NP | NP |
| 17 | 6-Chloro-1-phenyl-1H-indol-3-yl-beta-D-galactopyranoside | I9a | 9 | Air/MDAB | a | Enzyme: beta-D-galactosidase | 9 | NA | (9) |
| 18 | 1-[2-(Methoxy-carbonyl)phenyl]-1H-indol-3-yl-beta-D-galactopyranoside | I10a | 10 | Air/MDAB | a | Enzyme: beta-D-galactosidase | — | 10 | — |
| 19 | 6-Chloro-1-[2-(methoxy-carbonyl)phenyl]-1H-indol-3-yl-beta-D-galactopyranoside | I11a | 11 | Air/MDAB | a | Enzyme: beta-D-galactosidase | 11 | (10) | — |
| 20 | 5-Bromo-4-chloro-1-[2-(methoxycarbonyl)phenyl]-1H-indol-3-yl-beta-D-galactopyranoside | I12a | 12 | Air/MDAB | a | Enzyme: beta-D-galactosidase | — | 12 | (12) |
| 21 | 1-(2-Formylphenyl)-1H-indol-3-yl-beta-D-galactopyranoside | I13a | 13 | Air/MDAB | a | Enzyme: beta-D-galactosidase | — | 13 | (13) |
| 22 | 1-(2-Acetylphenyl)-1H-indol-3-yl-beta-D-galactopyranoside | I14a | 14 | Air/MDAB | a | Enzyme: beta-D-galactosidase | — | 14 | — |
| 23 | 1-(2-Acetylphenyl)-4-chloro-1H-indol-3-yl-beta-D-galactopyranoside | I15a | 15 | Air/MDAB | a | Enzyme: beta-D-galactosidase | — | 15 | — |
| 24 | 1-(2-Acetylphenyl)-6-chloro-1H-indol-3-yl-beta-D-galactopyranoside | I16a | 16 | Air/MDAB | a | Enzyme: beta-D-galactosidase | — | 16 | — |
| 25 | 1-(2-Acetylphenyl)-5-bromo-4-chloro-1H-indol-3-yl-beta-D-galactopyranoside | I17a | 17 | Air/MDAB | a | Enzyme: beta-D-galactosidase | — | 17 | — |
| 26 | 1-(2-Acetyl-5-methoxy-phenyl)-6-chloro-1H-indol-3-yl-beta-D-galactopyranoside | I18a | 18 | Air/MDAB | a | Enzyme: beta-D-galactosidase | — | 18 | — |
| 27 | 1-(2-Benzoylphenyl)-1H-indol-3-yl-beta-D-galactopyranoside | I19a | 19 | Air/MDAB | a | Enzyme: beta-D-galactosidase | — | 19 | — |
| 28 | 1-(2-Benzoylphenyl)-1H-indol-3-yl acetate | I19c | 19 | Air/MDAB | c | Enzyme: Esterase; Ion: Hydroxide | NP | NP | NP |
| 29 | 1-(2-Benzoylphenyl)-4-chloro-1H-indol-3-yl-beta-D-galactopyranoside | I20a | 20 | Air/MDAB | a | Enzyme: beta-D-galactosidase | — | 20 | — |
| 30 | 1-(2-Benzoylphenyl)-6-chloro-1H-indol-3-yl-beta-D-galactopyranoside | I21a | 21 | Air/MDAB | a | Enzyme: beta-D-galactosidase | — | 21 | — |
| 31 | 1-(2-Benzoylphenyl)-6-chloro-1H-indol-3-yl-alpha-D-glucopyranoside | I21e | 21 | Air/MDAB | e | Enzyme: alpha-glucosidase | NP | NP | NP |

TABLE IIb-continued

List of Aerobic 1H-Indol-3-yl/MDAB Indicator Systems

| Entry | Indicator/Active Signalogen | Code | aS | aR | LG | External Stimulus | Signalophore BI | Signalophore IO | Signalophore IN |
|---|---|---|---|---|---|---|---|---|---|
| 32 | 1-(2-Benzoylphenyl)-6-chloro-1H-indol-3-yl-beta-D-glucuronide sodium salt | I21f | 21 | Air/MDAB | f | Enzyme: beta-D-glucuronidase | NP | NP | NP |
| 33 | 1-(2-Benzoylphenyl)-6-chloro-1H-indol-3-yl-N-acetyl-beta-D-galactosaminide | I21g | 21 | Air/MDAB | g | Enzyme: Galactosamidase | NP | NP | NP |
| 34 | 1-(2-Benzoylphenyl)-5-bromo-4-chloro-1H-indol-3-yl-beta-D-galactopyranoside | I22a | 22 | Air/MDAB | a | Enzyme: beta-D-galactosidase | — | 22 | — |
| 35 | 1-(2-Benzoyl-5-chlorophenyl)-6-chloro-1H-indol-3-yl-beta-D-galactopyranoside | I23a | 23 | Air/MDAB | a | Enzyme: beta-D-galactosidase | — | 23 | — |
| 36 | 1-(2-Benzoyl-5-methoxy-phenyl)-6-chloro-1H-indol-3-yl-beta-D-galactopyranoside | I24a | 24 | Air/MDAB | a | Enzyme: beta-D-galactosidase | — | 24 | — |
| 37 | 1-[2-(2,4-Dimethoxy-benzoyl)phenyl]-1H-indol-3-yl-beta-D-galactopyranoside | I25a | 25 | Air/MDAB | a | Enzyme: beta-D-galactosidase | — | 25 | — |
| 38 | 1-[2-(2,4-Dimethoxy-benzoyl)phenyl]-1H-indol-3-yl acetate | I25c | 25 | Air/MDAB | c | Enzyme: Esterase; Ion: Hydroxide | NP | NP | NP |
| 39 | 1-[2-(2,4-Dimethoxy-benzoyl)phenyl]-1H-indol-3-yl choline phosphate | I25d | 25 | Air/MDAB | d | Enzyme: Phospholipase c | NP | NP | NP |
| 40 | 1-[2-(2,4-Dimethoxy-benzoyl)phenyl]-6-chloro-1H-indol-3-yl-beta-D-galactopyranoside | I27a | 27 | Air/MDAB | a | Enzyme: beta-D-galactosidase | — | 27 | — |
| 41 | 1-[2-(2,4-Dimethoxy-benzoyl)phenyl]-4-chloro-1H-indol-3-yl-beta-D-galactopyranoside | I26a | 26 | Air/MDAB | a | Enzyme: beta-D-galactosidase | — | 26 | — |
| 42 | 5-Bromo-4-chloro-1-[2-(2,4-dimethoxybenzoyl)phenyl]-1H-indol-3-yl-beta-D-galactopyranoside | I28a | 28 | Air/MDAB | a | Enzyme: beta-D-galactosidase | — | 28 | — |
| 43 | 6-Chloro-1-[2-(5-carboxyl-furanoyl)phenyl)-1H-indol-3-yl-beta-D-galactopyranoside | I29a | 29 | Air/MDAB | a | Enzyme: beta-D-galactosidase | — | 29 | — |
| 44 | 6-Chloro-1-(2-furanoyl-phenyl)-1H-indol-3-yl-beta-D-galactopyranoside | I30a | 30 | Air/MDAB | a | Enzyme: beta-D-galactosidase | — | 30 | — |
| 45 | 6-Chloro-1-[2-(N-methyl-pyrrole-2-carbonyl)phenyl]-1H-indol-3-yl-beta-D-galactopyranoside | I31a | 31 | Air/MDAB | a | Enzyme: beta-D-galactosidase | NP | NP | NP |
| 46 | 1-(2-Benzoylphenyl)-1H-indol-3-yl ethyl carbamate | I32 | 32 | Air/MDAB | 1) | Enzyme: Esterase; Ion: Hydroxide | NP | NP | NP |
| 47 | Bis(1-(2-acetylphenyl)-1H-indol-3-yl]-disulfane | I33 | 33 | Air/MDAB | 2) | Reducing Agent: TCEP | NP | NP | NP |

NP: Not Performed
NA: Not Applicable
*: yellow-brown solution
1) LG: —N=C=O-Ethyl (ethylcarbamate)
2) LG: —S—S-(disulfane) or isothiuronium iodide

TABLE IIc

List of Anaerobic 1H-Indol-3-yl/MDAB Indicator Systems

| Entry | Indicator/(active Signalogen) | Code | aS | aR | LG | External Stimulus | Signalophore BI | Signalophore IO | Signalophore IN |
|---|---|---|---|---|---|---|---|---|---|
| 1 | 1H-Indol-3-yl-beta-D-galactopyranoside | I1a | 1 | MDAB | a | Enzyme: beta-D-galactosidase | 1 | NA | — |
| 2 | 1H-Indol-3-yl acetate | I1c | 1 | MDAB | c | Enzyme: Esterase; Ion: Hydroxide | 1 | NA | — |
| 3 | 4-Chloro-1H-indol-3-yl-beta-D-galactopyranoside | I2a | 2 | MDAB | a | Enzyme: beta-D-galactosidase | 2 | NA | — |

TABLE IIc-continued

List of Anaerobic 1H-Indol-3-yl/MDAB Indicator Systems

| Entry | Indicator/(active Signalogen) | Code | aS | aR | LG | External Stimulus | Signalophore BI | IO | IN |
|---|---|---|---|---|---|---|---|---|---|
| 4 | 6-Chloro-1H-indol-3-yl-beta-D-galactopyranoside | I3a | 3 | MDAB | a | Enzyme: beta-D-galactosidase | 3 | NA | — |
| 5 | 6-Chloro-1H-indol-3-yl-alpha-D-glucopyranoside | I3e | 3 | MDAB | e | Enzyme: alpha-glucosidase | NP | NP | NP |
| 6 | 6-Chloro-1H-indol-3-yl-beta-D-glucuronide sodium salt | I3f | 3 | MDAB | f | Enzyme: beta-D-glucuronidase | NP | NP | NP |
| 7 | 6-Chloro-1H-indol-3-yl-N-acetyl-beta-D-galactosaminide | I3g | 3 | Air/MDAB | g | Enzyme: Galactosamidase | NP | NP | NP |
| 8 | 5-Bromo-4-chloro-1H-indol-3-yl-beta-D-galactopyranoside | I4a | 4 | MDAB | a | Enzyme: beta-D-galactosidase | 4 | NA | — |
| 9 | 5-Bromo-3-(tert-butyldimethyl-silyloxy)-4-chloro-1H-indole | I4b | 4 | MDAB | b | Ion: Fluoride | 4 | NA | — |
| 10 | 5-Bromo-4-chloro-1H-indol-3-yl acetate | I4c | 4 | MDAB | c | Enzyme: Esterase | 4 | NA | — |
| 11 | 5-Bromo-4-chloro-1H-indol-3-yl choline phosphate | I4d | 4 | MDAB | d | Enzyme: Phospholipase c | NP | NP | NP |
| 12 | 5-Bromo-4-chloro-1H-indol-3-yl-beta-D-glucopyranoside | I4h | 4 | Air/MDAB | h | Enzyme: beta-D-glucosidase | NP | NP | NP |
| 13 | 5-Bromo-6-chloro-1H-indol-3-yl-beta-D-galactopyranoside | I5a | 5 | MDAB | a | Enzyme: beta-D-galactosidase | 4 | NA | — |
| 14 | 1H-Indol-3-yl-ethyl carbamate | I6 | 6 | MDAB | | — | — | NA | * |
| 15 | (1H-Indol-3-thiol) | NA | 7 | MDAB | | — | 6 | NA | — |
| 16 | 1-Phenyl-1H-indol-3-yl-beta-D-galactopyranoside | I8a | 8 | MDAB | a | Enzyme: beta-D-galactosidase | NP | NP | NP |
| 17 | 6-Chloro-1-phenyl-1H-indol-3-yl-beta-D-galactopyranoside | I9a | 9 | MDAB | a | Enzyme: beta-D-galactosidase | 9 | NA | — |
| 18 | 1-[2-(Methoxycarbonyl)phenyl]-1H-indol-3-yl-beta-D-galactopyranoside | I10a | 10 | MDAB | a | Enzyme: beta-D-galactosidase | — | 10 | — |
| 19 | 6-Chloro-1-[2-(methoxy-carbonyl)phenyl]-1H-indol-3-yl-beta-D-galactopyranoside | I11a | 11 | MDAB | a | Enzyme: beta-D-galactosidase | 11 | 11 | — |
| 20 | 5-Bromo-4-chloro-1-[2-(methoxy-carbonyl)phenyl]-1H-indol-3-yl-beta-D-galactopyranoside | I12a | 12 | MDAB | a | Enzyme: beta-D-galactosidase | — | 12 | — |
| 21 | 1-(2-Formylphenyl)-1H-indol-3-yl-beta-D-galactopyranoside | I13a | 13 | MDAB | a | Enzyme: beta-D-galactosidase | — | 13 | — |
| 22 | 1-(2-Acetylphenyl)-1H-indol-3-yl-beta-D-galactopyranoside | I14a | 14 | MDAB | a | Enzyme: beta-D-galactosidase | — | 14 | — |
| 23 | 1-(2-Acetylphenyl)-4-chloro-1H-indol-3-yl-beta-D-galactopyranoside | I15a | 15 | MDAB | a | Enzyme: beta-D-galactosidase | — | 15 | — |
| 24 | 1-(2-Acetylphenyl)-6-chloro-1H-indol-3-yl-beta-D-galactopyranoside | I16a | 16 | MDAB | a | Enzyme: beta-D-galactosidase | — | 16 | — |
| 25 | 1-(2-Acetylphenyl)-5-bromo-4-chloro-1H-indol-3-yl-beta-D-galactopyranoside | I17a | 17 | MDAB | a | Enzyme: beta-D-galactosidase | — | 17 | — |
| 26 | 1-(2-Acetyl-5-methoxyphenyl)-6-chloro-1H-indol-3-yl-beta-D-galactopyranoside | I18a | 18 | MDAB | a | Enzyme: beta-D-galactosidase | — | 18 | — |
| 27 | 1-(2-Benzoylphenyl)-1H-indol-3-yl-beta-D-galactopyranoside | I19a | 19 | MDAB | a | Enzyme: beta-D-galactosidase | — | 19 | — |
| 28 | 1-(2-Benzoylphenyl)-1H-indol-3-yl acetate | I19c | 19 | MDAB | c | Enzyme: Esterase | NP | NP | NP |
| 29 | 1-(2-Benzoylphenyl)-4-chloro-1H-indol-3-yl-beta-D-galactopyranoside | I20a | 20 | MDAB | a | Enzyme: beta-D-galactosidase | — | 20 | — |
| 30 | 1-(2-Benzoylphenyl)-6-chloro-1H-indol-3-yl-beta-D-galactopyranoside | I21a | 21 | MDAB | a | Enzyme: beta-D-galactosidase | — | 21 | — |
| 31 | 1-(2-Benzoylphenyl)-6-chloro-1H-indol-3-yl-alpha-D-glucopyranoside | I21e | 21 | MDAB | e | Enzyme: alpha-glucosidase | NP | NP | NP |
| 32 | 1-(2-Benzoylphenyl)-6-chloro-1H-indol-3-yl-beta-D-glucuronide sodium salt | I21f | 21 | MDAB | f | Enzyme: beta-D-glucuronidase | NP | NP | NP |
| 33 | 1-(2-Benzoylphenyl)-6-chloro-1H-indol-3-yl-N-acetyl-beta-D-galactosaminide | I21g | 21 | MDAB | g | Enzyme: Galactosamidase | NP | NP | NP |
| 34 | 1-(2-Benzoylphenyl)-5-bromo-4-chloro-1H-indol-3-yl-beta-D-galactopyranoside | I22a | 22 | MDAB | a | Enzyme: beta-D-galactosidase | — | 22 | — |

TABLE IIc-continued

List of Anaerobic 1H-Indol-3-yl/MDAB Indicator Systems

| Entry | Indicator/(active Signalogen) | Code | aS | aR | LG | External Stimulus | Signalophore BI | IO | IN |
|---|---|---|---|---|---|---|---|---|---|
| 35 | 1-(2-Benzoyl-5-chlorophenyl)-6-chloro-1H-indol-3-yl-beta-D-galactopyranoside | I23a | 23 | MDAB | a | Enzyme: beta-D-galactosidase | — | 23 | — |
| 36 | 1-(2-Benzoyl-5-methoxyphenyl)-6-chloro-1H-indol-3-yl-beta-D-galactopyranoside | I24a | 24 | MDAB | a | Enzyme: beta-D-galactosidase | — | 24 | — |
| 37 | 1-[2-(2,4-Dimethoxy-benzoyl)lphenyl]-1H-indol-3-yl-beta-D-galactopyranoside | I25a | 25 | MDAB | a | Enzyme: beta-D galactosidase | — | 25 | — |
| 38 | 1-[2-(2,4-Dimethoxy-benzoyl)phenyl]-1H-indol-3-yl acetate | I25c | 25 | MDAB | c | Enzyme: Esterase | NP | NP | NP |
| 39 | 1-[2-(2,4-Dimethoxy-benzoyl)phenyl]-1H-indol-3-yl choline phosphate | I25d | 25 | MDAB | d | Enzyme: Phospholipase c | NP | NP | NP |
| 40 | 1-[2-(2,4-Dimethoxy-benzoyl)phenyl]-6-chloro-1H-indol-3-yl-beta-D-galactopyranoside | I27a | 27 | MDAB | a | Enzyme: beta-D-galactosidase | — | 27 | — |
| 41 | 1-[2-(2,4-Dimethoxy-benzoyl)phenyl]-4-chloro-1H-indol-3-yl-beta-D-galactopyranoside | I26a | 26 | MDAB | a | Enzyme: beta-D-galactosidase | — | 26 | — |
| 42 | 1-[2-(2,4-Dimethoxy-benzoyl)phenyl]-5-bromo-4-chloro-1H-indol-3-yl-beta-D-galactopyranoside | I28a | 28 | MDAB | a | Enzyme: beta-D-galactosidase | — | 28 | — |
| 43 | 1-[2-(5-Carboxylfuranoyl)phenyl]-6-chloro-1H-indol-3-yl-beta-D-galactopyranoside | I29a | 29 | MDAB | a | Enzyme: beta-D-galactosidase | — | 29 | — |
| 44 | 6-Chloro-1-(2-furanoylphenyl)-1H-indol-3-yl-beta-D-galactopyranoside | I30a | 30 | MDAB | a | Enzyme: beta-D-galactosidase | — | 30 | — |
| 45 | 6-Chloro-1-[2-(N-methylpyrrole-2-carbonyl)phenyl]-1H-indol-3-yl-beta-D-galactopyranoside | I31a | 31 | MDAB | a | Enzyme: beta-D-galactosidase | NP | NP | NP |
| 46 | 1-(2-Benzoylphenyl)-1H-indol-3-yl ethyl carbamate | I32 | 32 | MDAB | | Enzyme: Esterase | NP | NP | NP |
| 47 | Bis(1-(2-acetylphenyl)-1H-indol-3-yl]-disulfane | I33 | 33 | MDAB | | Reducing Agent: TCEP | NP | NP | NP |

NP: Not Performed
NA: Not Applicable
*: yellow-brown solution
1) LG: —N—C=O-Ethyl (ethylcarbamate)
2) LG: —S—S-(disulfane) or isothiuronium iodide

TABLE III

2-Benzylideneindoline (MDAB) staining of colonies of beta-D-galactosidase positive/negative bacteria

| Entry | Indicator | aR | Equivalents | Species | eS | aerobic conditions | microaerobic (anaerobic) conditions |
|---|---|---|---|---|---|---|---|
| | | | | | b-gal | TSAYE with 40 mg/100 ml of indicator | TSAYE with 40 mg/100 ml of indicator |
| 1 | I4a | — | NA | Citrobacter freundii | + | Blue green (dark colored colonies) with no ring | Green (light colored colonies) with no ring |
| 2 | I4a | DAB | 2:1 | Citrobacter freundii | + | Blue green (medium colored colonies) with no ring | Cream colored colonies with no ring |
| 3 | I4a | DAB | 1:1 | Citrobacter freundii | + | Blue green (light colored colonies) with clear ring | Cream colored colonies with no ring |
| 4 | I4a | MDAB | 2:1 | Citrobacter freundii | + | Blue green (dark colored colonies) with light ring | Green (light colored colonies) with no ring |
| 5 | I4a | MDAB | 1:1 | Citrobacter freundii | + | Blue green (light colored colonies) with pale red hue | Pink (light colored colonies) with no ring |
| 6 | I4a | — | NA | Escherichia coli | + | Blue green (very dark colored colonies) with no ring | Green (light colored colonies) with no ring |
| 7 | I4a | DAB | 2:1 | Escherichia coli | + | Blue green (very dark colored colonies) with no ring | Pale green (very light colored colonies) with no ring |

TABLE III-continued

2-Benzylideneindoline (MDAB) staining of colonies of beta-D-galactosidase positive/negative bacteria

| Entry | Indicator | aR | Equivalents | Species | eS | aerobic conditions | microaerobic (anaerobic) conditions |
|---|---|---|---|---|---|---|---|
| 8 | I4a | DAB | 1:1 | Escherichia coli | + | Blue green (very dark colored colonies) with no ring | Cream colored colonies with no ring |
| 9 | I4a | MDAB | 2:1 | Escherichia coli | + | Blue green (very dark colored colonies) with no ring | Green (light colored colonies) with cream ring |
| 10 | I4a | MDAB | 1:1 | Escherichia coli | + | Blue green (very dark colored colonies) with white ring | Pink (medium colored colonies) with cream ring |
| 11 | I4a | MDAB | 1:1 | Salmonella manhattan | − | Cream colored colonies | Cream colored colonies |
| 12 | I4a | MDAB | 1:1 | Salmonella manhattan | − | Cream colored colonies | Cream colored colonies |
| 13 | I5a | — | NA | Citrobacter freundii | + | Violet (dark colored colonies) with a clear ring | Pale violet (light colored colonies) with no ring |
| 14 | I5a | DAB | 2:1 | Citrobacter freundii | + | Violet (medium colored colonies) with a clear ring | Cream colored colonies with no ring |
| 15 | I5a | DAB | 1:1 | Citrobacter freundii | + | Violet (light medium colored colonies) with a white ring | Cream colored colonies with no ring |
| 16 | I5a | MDAB | 2:1 | Citrobacter freundii | + | Violet (dark colored colonies) with a clear ring | Violet (light colored colonies) with a clear ring |
| 17 | I5a | MDAB | 1:1 | Citrobacter freundii | + | Violet (medium colored colonies) with a clear ring | Violet (medium colored colonies) with a clear ring |
| 18 | I5a | — | NA | Salmonella manhattan | − | Cream colored colonies | Cream colored colonies |
| 19 | I5a | — | NA | Escherichia coli | + | Violet (very dark colored colonies) with no ring | Pale violet (light colored colonies) with no ring |
| 20 | I5a | DAB | 2:1 | Escherichia coli | + | Violet (very dark colored colonies) with no ring | Cream colored colonies with no ring |
| 21 | I5a | DAB | 1:1 | Escherichia coli | + | Violet (medium colored colonies) with a clear ring | Cream colored colonies with no ring |
| 22 | I5a | MDAB | 2:1 | Escherichia coli | + | Violet (very dark colored colonies) with no ring | Violet (light colored colonies) with a clear ring |
| 23 | I5a | MDAB | 1:1 | Escherichia coli | + | Violet (very dark colored colonies) with no ring | Violet (medium colored colonies) with a clear ring |
| 24 | I5a | — | NA | Salmonella manhattan | − | Cream colored colonies | Cream colored colonies |
| 25 | I5a | MDAB | 1:1 | Salmonella manhattan | − | Cream colored colonies | Cream colored colonies |
| 26 | I9a | — | NA | Escherichia coli | + | Cream to olive colored colonies | — |
| 27 | I9a | MDAB | 1:1 | Escherichia coli | + | Red colored colonies | — |
| 28 | I9a | MDAB | 1:1 | Salmonella enteritidis | − | Cream colored colonies | — |
| 29 | I10a | — | NA | Escherichia coli | + | Cream to olive colored colonies | — |
| 30 | I10a | MDAB | 1:1 | Escherichia coli | + | Cream to olive colored colonies | — |
| 31 | I10a | MDAB | 1:1 | Salmonella enteritidis | − | Cream colored colonies | — |
| 32 | I11a | — | NA | Escherichia coli | + | Cream to olive colored colonies | — |
| 33 | I11a | MDAB | 1:1 | Escherichia coli | + | Red to brown colored colonies | — |
| 34 | I11a | MDAB | 1:1 | Salmonella enteritidis | − | Cream colored colonies | — |
| 35 | I12a | — | NA | Escherichia coli | + | Cream to olive colored colonies | — |
| 36 | I12a | MDAB | 1:1 | Escherichia coli | + | Brown colored colonies | — |
| 37 | I12a | MDAB | 1:1 | Salmonella enteritidis | − | Cream colored colonies | — |

DAB: 4-(Dimethylamino)benzaldehyde
MDAB: 2-Methoxy-4-(dimethylamino)benzaldehyde
b-gal: beta-D-galactosidase
−: absent
+: present TABLE IVa Color, fluorescence and localization of various IO stains on microbial plating media
Bacterial colonies after 24 h on Nutrient Agar containing
150 mg/l substrate and 100 mg/l IPTG

|  |  |  |  | *E. coli* | *S. enteritidis* |
|---|---|---|---|---|---|
|  |  |  | eS: b-gal | + | − |
| I19a | 1-(2-Benzoylphenyl)-1H-indol-3-yl-β-D-galactopyranoside | C | yellow-orange | + | − |
|  |  | F | yellow | + | − |
|  |  | L |  | + | NA |
|  |  | G |  | + | + |
| I17a | 1-(2-Acetylphenyl)-5-bromo-4-chloro-1H-indol-3-yl-β-D-galactopyranoside | C | yellow-orange | + | − |
|  |  | F | — | − | − |
|  |  | L |  | + | NA |
|  |  | G |  | + | + |
| I20a | 1-(2-Benzoylphenyl)-4-chloro-1H-indol-3-yl-β-D-galactopyranoside | C | orange | +/− | − |
|  |  | F | orange | +/− | − |
|  |  | L |  | cryst. | NA |
|  |  | G |  | + | + |
| I13a | 1-(2-Formylphenyl)-1H-indol-3-yl-β-D-galactopyranoside | C | cream-orange | +/− | − |
|  |  | F | — | − | − |
|  |  | L |  | + |  |
|  |  | G |  | + | + |
| I10a | 1-[2-(Methoxycarbonyl)phenyl]-1H-indol-3-yl-β-D-galactopyranoside | C | yellow-green | + | − |
|  |  | F | green | + | − |
|  |  | L |  | − | NA |
|  |  | G |  | + | + |
| I28a | 5-Bromo-4-chloro-1-[2-(2,4-dimethoxybenzoyl)phenyl]-1H-indol-3-yl-β-D-galactopyranoside | C | orange | + | − |
|  |  | F | (red) | +/− | − |
|  |  | L |  | + | NA |
|  |  | G |  | + | + |
| I26a | 4-Chloro-1-[2-(2,4-dimethoxybenzoyl)phenyl]-1H-indol-3-yl-β-D-galactopyranoside | C | yellow-orange | + | − |
|  |  | F | orange | +/− | − |
|  |  | L |  | + | NA |
|  |  | G |  | + | + |
| I12a | 5-Bromo-4-chloro-1-[2-(methoxycarbonyl)phenyl]-1H-indol-3-yl-β-D-galactopyranoside | C | yellow-green | +/− | − |
|  |  | F | green | +/− | − |
|  |  | L |  | − | NA |
|  |  | G |  | + | + |
| I11a | 6-Chloro-1-[2-(methoxycarbonyl)phenyl]-1H-indol-3-yl-β-D-galactopyranoside | C | yellow-green | + | − |
|  |  | F | green | + | − |
|  |  | L |  | − | NA |
|  |  | G |  | + | + |
| I29a | 6-Chloro-1-[2-(5-carboxyl-furanoyl)phenyl]-1H-indol-3-yl-β-D-galactopyranoside | C | red | + | − |
|  |  | F | — | − | − |
|  |  | L |  | − |  |
|  |  | G |  | + | + |
| I30a | 6-Chloro-1-(2-furanoylphenyl)-1H-indol-3-yl-β-D-galactopyranoside | C | dark orange | ++ | − |
|  |  | F | orange-red | +/− | − |
|  |  | L |  | +/− |  |
|  |  | G |  | + | + |
| I23a | 6-Chloro-1-(2-benzoyl-5-chlorophenyl)-1H-indol-3-yl-β-D-galactopyranoside | C | yellow | + | NA |
|  |  | F | green-yellow | + | NA |
|  |  | L |  | + | NA |
|  |  | G |  | + | NA |
| I18a | 1-(2-Acetyl-5-methoxyphenyl)-1H-indol-3-yl-β-D-galactopyranoside | C | light yellow | + | − |
|  |  | F | green | +/− | − |
|  |  | L |  | +/− | NA |
|  |  | G |  | + | + |
| I24a | 1-(2-Benzoyl-5-methoxyphenyl)-1H-indol-3-yl-β-D-galactopyranoside | C | dark yellow | + | − |
|  |  | F | yellow-green | + | − |
|  |  | L |  | +/− | NA |
|  |  | G |  | + | + |
| I14a | 1-(2-Acetylphenyl)-1H-indol-3-yl-β-D-galactopyranoside | C | light yellow | + | − |
|  |  | F | — | − | − |
|  |  | L |  | + | NA |
|  |  | G |  | + | + |

C: Color of colonies
F: Fluorescence of colonies
G: Growth of colonies
L: Localization of stain on colonies
eS: External stimulus
b-gal: beta-D-galactosidase
NA: not applicable
−: absent
+/−: weak
+: strong
++: very strong TABLE IVb IO staining of colonies of beta-D-galactosidase positive/negative bacteria
Bacterial colonies after 24 h on Nutrient Agar containing
150 mg/l beta-D-galactosidase indicator and 100 mg/l IPTG

| | | | I16a | | | I21a | | | I22a | | | I25a | | |
|---|---|---|---|---|---|---|---|---|---|---|---|---|---|---|
| Species | Strain | eS b-gal | C y | F g | G | C y | F y-g | G | C o | F o | G | C y | F o | G |
| Aeromonas hydrophila | 292 | + | + | + | + | + | + | + | +/− | +/− | + | + | +/− | + |
| Citrobacter freundii | 181 | + | + | + | + | + | + | + | + | +/− | + | + | + | + |
| Enterobacter aerogenes | 242 | + | + | + | + | + | + | + | + | +/− | + | + | + | + |
| Enterobacter cloacae | 245 | + | + | + | + | + | + | + | + | +/− | + | + | ++ | + |
| Escherichia coli (O157:H7) | 60 | + | + | + | + | + | + | + | + | +/− | + | ++ | ++ | + |
| Escherichia coli | 61 | + | + | + | + | + | + | + | + | +/− | + | ++ | ++ | + |
| Escherichia coli | 270 | + | + | + | + | ++ | + | + | + | +/− | + | ++ | ++ | + |
| Klebsiella pneumoniae | 164 | + | + | + | + | + | + | + | + | +/− | + | + | + | + |
| Serratia marcescens | 40 | + | + | + | + | ++ | + | + | + | +/− | + | + | +/− | + |
| Staphylococcus intermedius | 31 | + | +/− | +/− | +/− | +/− | +/− | +/− | − | − | − | +/− | +/− | + |
| Staphylococcus saprophyticus | 273 | + | + | + | + | + | + | + | − | − | − | +/− | +/− | + |
| Salmonella bongori | 81 | + | +/− | +/− | + | +/− | +/− | + | +/− | − | + | +/− | +/− | + |
| Salmonella illa | 73 | + | − | − | + | − | − | + | − | − | + | − | − | + |
| Shigella dysenteriae Serovar 1 | 131 | +/− | − | − | + | − | − | + | − | − | + | − | − | + |
| Shigella sonnei | 133 | +/− | + | + | + | + | + | + | + | +/− | + | + | ++ | + |
| Yersinia enterocolitica | 175 | +/− | − | − | + | − | +/− | + | − | − | + | − | − | + |
| Salmonella enteritidis | 43 | − | − | − | + | − | − | + | − | − | + | − | − | + |
| Bacillus subtilis | 65 | − | − | − | + | − | − | +/− | − | − | − | − | − | + |
| Listeria monocytogenes (4b) | 290 | − | − | − | +/− | − | − | +/− | − | − | − | − | − | +/− |
| Pseudomonas aeruginosa | 168 | − | − | +[1] | + | − | +[1] | + | − | +[1] | + | − | +[1] | + |
| Shigella boydii | 135 | − | − | − | + | − | − | + | − | − | + | − | − | + |
| Staphylococcus aureus | 2 | − | − | − | +/− | − | − | +/− | − | − | − | +/−[2] | − | + |
| Streptococcus agalactiae | 195 | − | − | − | +/− | − | − | +/− | − | − | − | − | − | +/− |

| | | | I28a | | | I27a | | | I31a | | | I4a (Control) | | |
|---|---|---|---|---|---|---|---|---|---|---|---|---|---|---|
| Species | Strain | eS b-gal | C o | F o | G | C y | F o | G | C r | F r | G | C b | F − | G |
| Aeromonas hydrophila | 292 | + | +/− | − | + | + | + | + | + | − | + | + | − | + |
| Citrobacter freundii | 181 | + | + | +/− | + | + | + | + | + | +/− | + | + | − | + |
| Enterobacter aerogenes | 242 | + | + | +/− | + | + | + | + | + | +/− | + | ++ | − | + |
| Enterobacter cloacae | 245 | + | + | +/− | + | ++ | ++ | + | + | +/− | + | ++ | − | + |
| Escherichia coli (O157:H7) | 60 | + | + | +/− | + | ++ | ++ | + | + | +/− | + | ++ | − | + |
| Escherichia coli | 61 | + | + | +/− | + | ++ | ++ | + | + | +/− | + | ++ | − | + |
| Escherichia coli | 270 | + | ++ | +/− | + | ++ | ++ | + | + | +/− | + | ++ | − | + |
| Klebsiella pneumoniae | 164 | + | + | +/− | + | + | + | + | + | +/− | + | ++ | − | + |
| Serratia marcescens | 40 | + | +/− | − | + | + | + | + | + | − | + | + | − | + |
| Staphylococcus intermedius | 31 | + | + | +/− | + | − | − | +/− | + | − | + | + | − | + |
| Staphylococcus saprophyticus | 273 | + | +/− | − | + | +/− | +/− | + | + | − | + | + | − | + |
| Salmonella bongori | 81 | + | +/− | − | + | +/− | +/− | + | +/− | − | + | +/− | − | + |
| Salmonella illa | 73 | + | − | − | + | − | − | + | − | − | + | − | − | + |
| Shigella dysenteriae Serovar 1 | 131 | +/− | − | − | + | − | − | + | − | − | + | − | − | + |
| Shigella sonnei | 133 | +/− | + | +/− | + | + | ++ | + | + | +/− | + | + | − | + |
| Yersinia enterocolitica | 175 | +/− | − | − | + | +/− | − | + | +/− | − | + | − | − | + |
| Salmonella enteritidis | 43 | − | − | − | + | − | − | + | − | − | + | − | − | + |
| Bacillus subtilis | 65 | − | − | − | +/− | − | − | + | − | − | + | − | − | + |
| Listeria monocytogenes (4b) | 290 | − | − | − | +/− | − | − | +/− | − | − | +/− | − | − | +/− |
| Pseudomonas aeruginosa | 168 | − | − | +[1] | + | − | +[1] | + | − | − | + | − | +[1] | + |
| Shigella boydii | 135 | − | − | − | + | − | − | + | − | − | + | − | − | + |
| Staphylococcus aureus | 2 | − | − | − | +/− | − | − | +/− | − | − | + | y[2] | − | + |
| Streptococcus agalactiae | 195 | − | − | − | +/− | − | − | +/− | − | − | +/− | − | − | +/− |

C: Color of colonies
F: Fluorescence of colonies
G: Growth of colonies
y: yellow
g: green
o: orange
r: red
b: blue
p: pink
−: absent
+/−: weak/variable
+: strong
++: very strong
[1] blue autofluorescence
[2] S. aureus natural color

TABLE IVc

IO staining of colonies of bacteria producing various biomarker enzymes

Bacterial colonies after 24 h on Nutrient Agar containing 0.45 mM beta-D-Glucuronidase Indicator

| Species | Strain | eS glucuronidase | I21f C y | I21f F y-o | I21f G | I3f (control) C p | I3f (control) F | I3f (control) G |
|---|---|---|---|---|---|---|---|---|
| Escherichia coli | 61 | + | + | +/− | + | + | − | + |
| Escherichia coli | 62 | + | + | +/− | + | + | − | + |
| Escherichia coli | 270 | + | + | +/− | + | + | − | + |
| Klebsiella pneumoniae | 164 | − | − | − | + | − | − | + |

Bacterial colonies after 24 h on Nutrient Agar containing 150 mg/l alpha-D-Glucosidase Indicator

| Species | Strain | eS a-glucosidase | I21e C y | I21e F y-g | I21e G |
|---|---|---|---|---|---|
| Enterobacter sakazakii | 141 | + | + | +/− | + |
| Enterobacter sakazakii | 142 | + | + | +/− | + |
| Enterobacter aerogenes | 242 | − | − | − | + |
| Enterobacter cloacae | 245 | − | − | − | + |
| Shigella sonnei | 133 | − | − | − | + |
| Escherichia coli | 270 | − | − | − | + |

Bacterial colonies after 24 h on Nutrient Agar containing 0.52 mM C1-Esterase Indicator

| Species | Strain | eS c1-esterase | I19c C y | I19c F y | I19c G | I4c (control) C b | I4c (control) F − | I4c (control) G |
|---|---|---|---|---|---|---|---|---|
| Klebsiella pneumoniae | 164 | + | + | * | + | + | − | + |
| Escherichia coli | 270 | +/− | +/− | * | + | − | − | +/− |
| Bacillus cereus | 289 | ++ | ++ | * | + | − | − | − |

Bacterial colonies after 24 h on Tryptic Soy Agar containing 0.78 mM PC PLC Indicator, 3.2 g/l BSA, 0.05% Tween80 and 5 mM $MnCl_2$

| Species | Strain | eS plc | I25d C y | I25d F y-g | I25d G | I4d (control) C b | I4d (control) F − | I4d (control) G |
|---|---|---|---|---|---|---|---|---|
| Bacillus cereus | 51 | + | + | ++ | + | +/− | − | + |
| Bacillus cereus | 289 | + | + | ++ | + | − | − | + |
| Bacillus cereus | 191 | + | + | ++ | + | +/− | − | + |
| Bacillus cereus | 192 | + | ++ | ++ | + | ++ | − | + |
| Bacillus mycoides | 64 | + | + | ++ | + | + | − | + |
| Bacillus thuringiensis | 66 | + | + | ++ | + | + | − | + |
| Escherichia coli | 61 | +/− | +/− | +/− | + | + | − | + |
| Escherichia coli | 270 | +/− | +/− | +/− | + | +/− | − | + |
| Listeria monocytogenes (4b) | 290 | + | − | − | + | − | − | + |
| Pseudomonas aeruginosa | 168 | + | y-g[1] | b[2] | + | y-g[1] | b[2] | + |

*: diffuse background due to some precipitation of substrate
[1] natural color, same on agar without substrate
[2] natural fluorescence, same on agar without substrate
I21f: 1-(2-Benzoylphenyl)-6-chloro-1H-indol-3-yl-beta-D-glucuronide sodium salt
I3f: 6-Chloro-1H-indol-3-yl-beta-D-glucuronide sodium salt
I21e: 1-(2-Benzoylphenyl)-6-chloro-1H-indol-3-yl-alpha-D-glucopyranoside
I19c: 1-(2-Benzoylphenyl)-1H-indol-3-yl acetate
I4c: 5-Bromo-4-chloro-1H-indol-3-yl acetate
I25d: 1-[2-(2,4-Dimethoxybenzoyl)phenyl]-1H-indol-3-yl choline phosphate
I4d: 5-Bromo-4-chloro-1H-indol-3-yl choline phosphate
eS: External Stimulus
glucuronidase: beta-D-glucuronidase
a-glucosidase: alpha-D-glucosidase
plc: phosphatidyl choline phospholipase c
C: Color of colonies
F: Fluorescence of colonies
G: Growth of colonies
y: yellow
g: green
o: orange
r: red
b: blue
p: pink
−: absent
+/−: weak/variable
+: strong
++: very strong

TABLE IVd

IN and IO concurrent staining of bacterial colonies Nutrient Agar containing beta-D-galactosidase IO indicator I21a and IN indicator I4h

| Species | Strain | eS: b-gal | eS: b-glu | C | G |
|---|---|---|---|---|---|
| Escherichia coli | 270 | + | − | y | + |
| Klebsiella pneumoniae | 164 | + | + | g | + |
| Enterobacter aerogenes | 242 | + | + | g | + |
| Enterococcus faecalis | 210 | − | + | b | + |

I21a: 1-(2-Benzoylphenyl)-6-chloro-1H-indol-3-yl-beta-D-galactopyranoside
I4h: 5-Bromo-4-chloro-1H-indol-3-yl-beta-D-glucopyranoside
IO: 10H-indolo[1,2-a]indole staining
IN: Indigo staining
eS: External Stimulus
b-gal: beta-D-galactosidase
b-glu: beta-D-glucosidase
−: absent
+/−: weak/variable
+: strong
y: yellow
g: green
b: blue

TABLE IVe

IN and IO staining of bacterial colonies under anaerobic conditions
Nutrient Agar plates containing various beta-D-galactosidase indicators anaerobically incubated with E. coli

| Indicator | Type/System | C | I | L | D | S | G |
|---|---|---|---|---|---|---|---|
| I21a | IO | y | + | + | +/− | 0.7 mm | + |
| I22a | IO | o-r | + | ++ | − | 0.5 mm | + |
| I27a | IO | y-o | + | + | +/− | 1 mm | + |
| I31a | IO | o-r | + | +/− | + | 0.8 mm | + |
| I4a | IN | b | +/− | − | ++ | pinpoint | +/− |

IN: Indigo staining
IO: 10H-indolo[1,2-a]indole staining
C: Color of colonies
I: Intensity of color
L: Localization on colonies
D: Diffusion around colonies
S: Size of colonies
G: Growth of colonies
−: absent
+/−: weak/variable
+: strong
++: very strong
I21a: 1-(2-Benzoylphenyl)-6-chloro-1H-indol-3-yl-beta-D-galactopyranoside
I22a: 1-(2-Benzoylphenyl)-5-bromo-4-chloro-1H-indol-3-yl-beta-D-galactopyranoside
I27a: 6-Chloro-1-[2-(2,4-dimethoxybenzoyl)phenyl]-1H-indol-3-yl-beta-D-galactopyranoside

TABLE IVe-continued

IN and IO staining of bacterial colonies under anaerobic conditions
Nutrient Agar plates containing various beta-D-galactosidase indicators anaerobically incubated with *E. coli*

| Indicator | Type/System | C | I | L | D | S | G |
|---|---|---|---|---|---|---|---|

I31a: 6-Chloro-1-[2-(N-methylpyrrole-2-carbonyl)phenyl]-1H-indol-3-yl-beta-D-galacto-pyranoside
I4a: 5-Bromo-4-chloro-1H-indol-3-yl-beta-D-galactopyranoside
y: yellow
r: red
b: blue
o: orange

TABLE IVf

IO staining of bacterial colonies on Blood Agar plates
*Klebsiella pneumoniae* colonies after 24 h on Blood Agar containing 150 mg/l I21a and 100 mg/l IPTG

| Indicator | Color of colonies | Color of colonies | Growth |
|---|---|---|---|
| I21a | white/visible Yellow | UV (366 nm) Yellow-orange on a dark background | + |
| — | Gray | Very weak bluish in front of dark background (hardly visible) | + |

IO: 10H-indolo[1,2-a]indole
I21a: 1-(2-Benzoylphenyl)-6-chloro-1H-indol-3-yl-beta-D-galactopyranoside
−: absent
+: strong

TABLE IVg

IO staining of fungal colonies
Agar plates containing indicator I21g

| Species | Strain | eS: galactosamidase | Color | Growth |
|---|---|---|---|---|
| *Candida albicans* | 304 | + | Yellow | +/− |
| *Candida krusei* | 305 | − | Cream | +/− |
| *Saccharomyces cerevisiae* | 306 | − | Cream | +/− |

IO: 10H-indolo[1,2-a]indole
I21g: 1-(2-Benzoylphenyl)-6-chloro-1H-indol-3-yl-N-acetyl-beta-D-galactosaminide
−: absent
+/−: weak/variable
+: strong

The invention claimed is:

1. An indicator system for detecting an external stimulus, comprising an indicator compound of the general formula

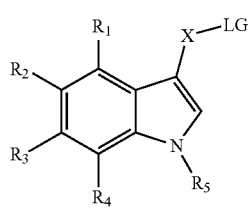

(A)

wherein:
X is O, NH or S;
LG is a labile group with the X-LG moiety being susceptible to conversion by action of said external stimulus;
$R_1$, $R_2$, $R_3$ and $R_4$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl;
$R_5$ is either hydrogen or $R_{12}$, wherein $R_{12}$ is

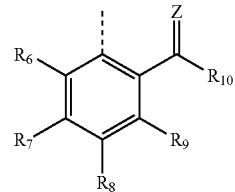

wherein:
Z is O, NH or S;
$R_6$, $R_7$, $R_8$, $R_9$ and $R_{10}$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl;
and wherein, if $R_5$ is hydrogen, the indicator system further comprises an acceptor compound of the general formula

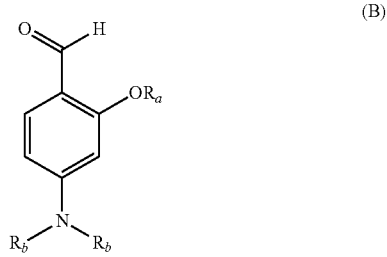

(B)

wherein:
$R_a$ and $R_b$ are independently selected from hydrogen and C1-4 alkyl.

2. The indicator system according to claim 1, wherein $R_5$ is hydrogen and the acceptor compound (B) is 2-methoxy-4-(N,N-dimethylamino)benzaldehyde.

3. The indicator system according to claim 1, wherein LG is selected from the group consisting of beta-D-galactopyranoside, tert-butyldimethylsilyloxy (TBDMS), acetate, choline phosphate, alpha-D-glucopyranoside, beta-D-glucuronide sodium salt, N-acetyl-beta-D-galactosaminide and beta-D-glucopyrano side.

4. The indicator system according to claim 1, wherein $R_{10}$ is selected from the group consisting of hydrogen, methyl, methoxy, phenyl, DMP, CFur, Fur, NPyr, wherein:

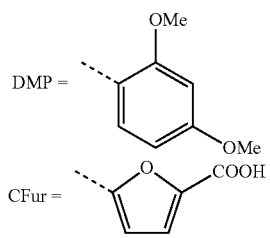

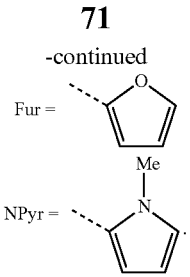

5. A method of detecting an external stimulus in a region of interest, comprising:

providing the region of interest with an indicator system; and monitoring for a signal from a signalophore species formed as a consequence of said external stimulus;

wherein said indicator system is as defined in claim 1 with the X-LG moiety being susceptible to conversion by action of said external stimulus, said conversion leading to formation of a signalogen species comprising an enolic moiety wherein XH is bound to a carbon atom that is bound to a further carbon atom by a double bond; said signalophore species being formed by reaction of said enolic moiety with an acceptor moiety selected from carbonyl, imino and thiocarbonyl.

6. The method according to claim 5, wherein said acceptor moiety is a carbonyl moiety.

7. The method according to claim 6, wherein said carbonyl moiety is provided by adding an acceptor compound of the general formula

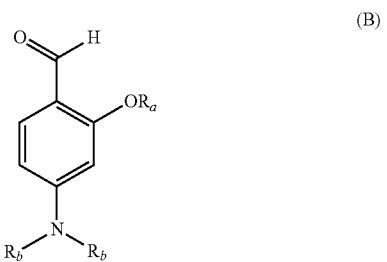

wherein:

$R_a$ and $R_b$ are independently selected from hydrogen and C1-4 alkyl.

8. The method according to claim 7, wherein the acceptor compound (B) is 2-methoxy-4-(N,N-dimethylamino)benzaldehyde.

9. The method according to claim 5, wherein said acceptor moiety is a part of said indicator molecule.

10. The method according to claim 5, wherein, if $R_5$ is hydrogen, the signalophore species is a 2-benzylideneindoline with the structural formula

and wherein, if $R_5$ is $R_{12}$, the signalophore species is a 10H-indolo[1,2-a]indole with the structural formula

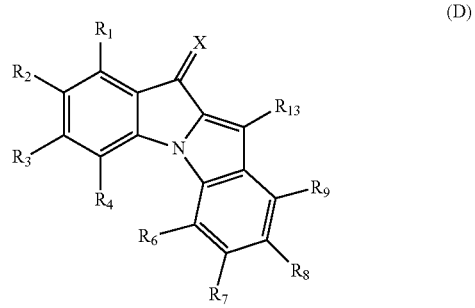

wherein $R_{13}$ is either OH or $R_{10}$.

11. The method according to claim 5, carried out under substantially oxygen-depleted conditions.

12. A method of preparing an indicator compound of the general formula

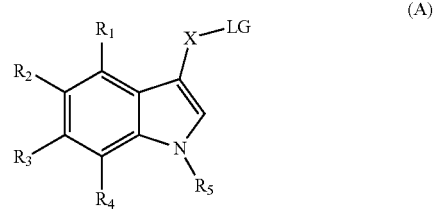

wherein:

X is O, NH or S;

LG is a labile group with the X-LG moiety being susceptible to conversion by action of said external stimulus;

$R_1$, $R_2$, $R_3$ and $R_4$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl;

and R$_5$ is R$_{12}$ which is

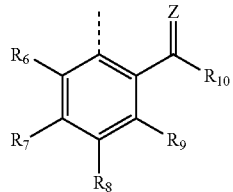

wherein:

Z is O, NH or S;

and wherein R$_6$, R$_7$, R$_8$, R$_9$ and R$_{10}$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl; characterized in that it comprises the step of N-arylation of an indoxyl compound of the general formula

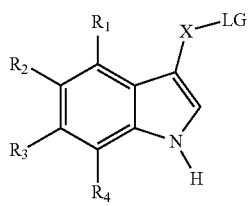

(E)

with a benzene derivative of the general formula

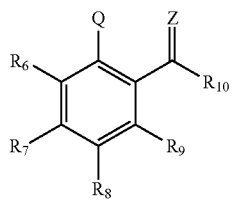

(F)

wherein Q is a leaving group selected from iodo, bromo, triflate and tosylate.

13. A compound of structural formula

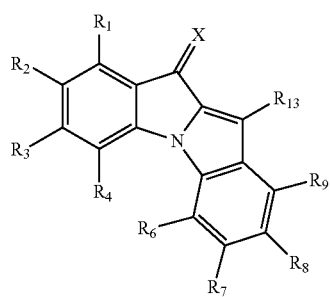

(G)

wherein

X is O, NH or S

R$_1$, R$_2$, R$_3$, R$_4$, R$_6$, R$_7$, R$_8$, R$_9$ and R$_{13}$ are independently selected from the group consisting of hydrogen, C1-4 alkyl; C1-4 alkoxy; fused or linearly connected aryl; fused or linearly connected heteroaryl; halogen; cyano; nitro; formyl; and optionally substituted amino, carboxy, carbonyl, hydroxy and sulfonyl, with the exception of the following compounds

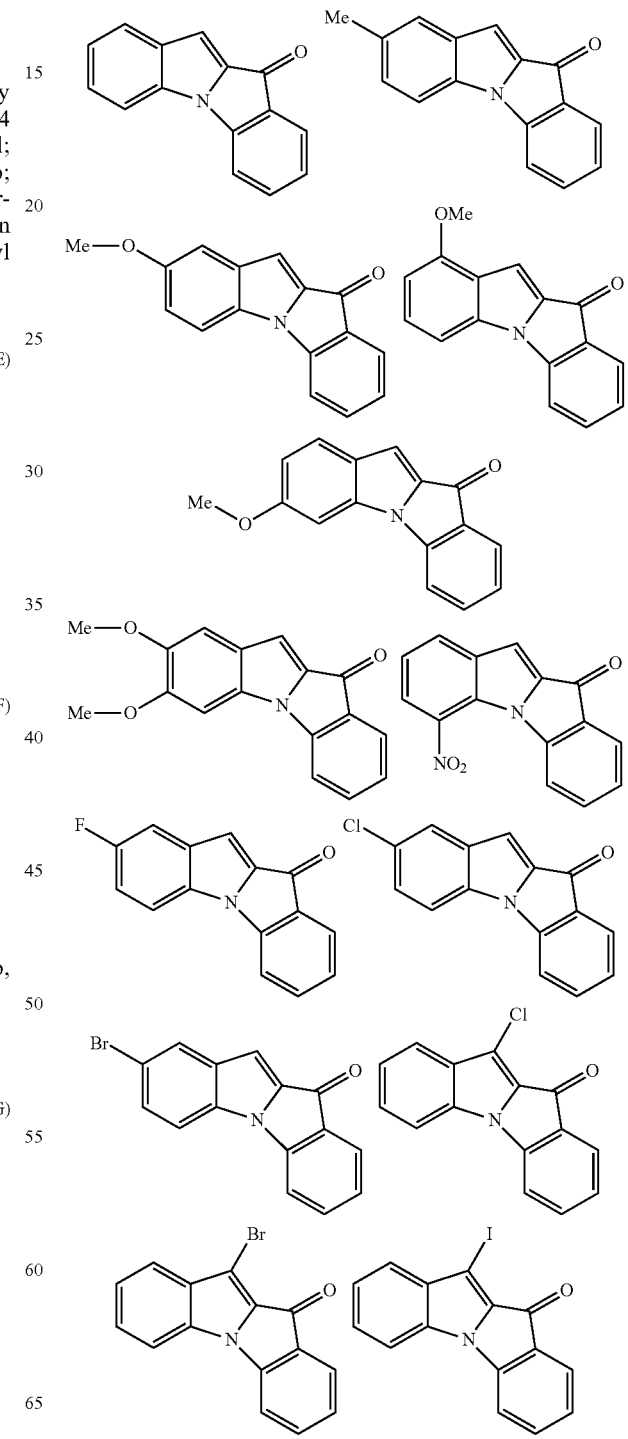

75
-continued
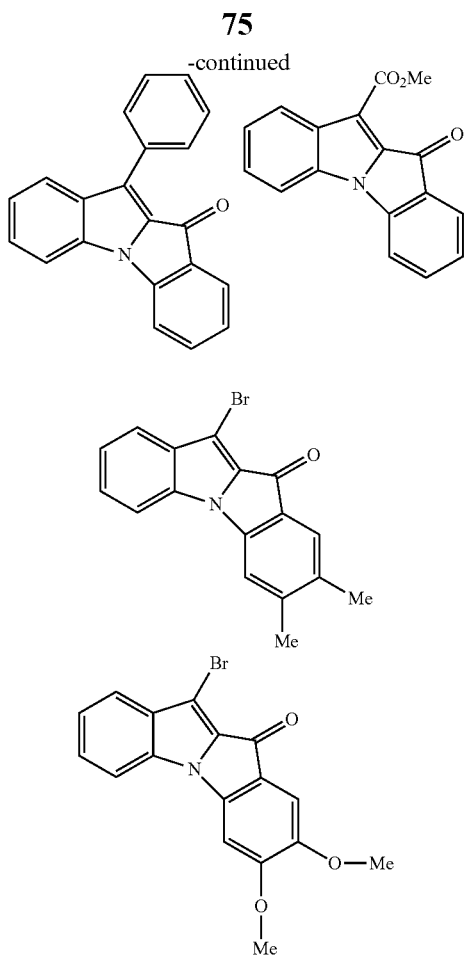
76
-continued
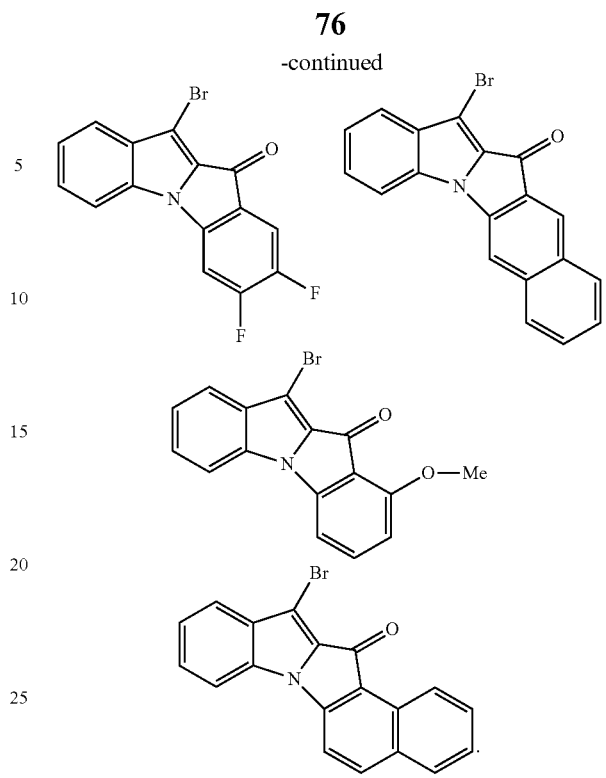
14. A method of administering the compound according to claim 13 in an indicator system for detecting an external stimulus, comprising administering the compound to a region of interest.
15. The method of claim 12, wherein Q is a leaving group selected from iodo or bromo.
* * * * *